United States Patent [19]

Greenlee et al.

[11] Patent Number: 5,025,007
[45] Date of Patent: Jun. 18, 1991

[54] 2-(9-FLUORENONYL)-CARBAPENEM ANTIBACTERIAL AGENTS

[75] Inventors: Mark L. Greenlee, Rahway; Frank P. DiNinno, Old Bridge; Lovji D. Cama, Tenafly; James V. Heck, Scotch Plains, all of N.J.

[73] Assignee: Merck & Co., Inc., Rahway, N.Y.

[21] Appl. No.: 561,541

[22] Filed: Aug. 1, 1990

[51] Int. Cl.$^5$ .................... C07D 487/04; A61K 31/40
[52] U.S. Cl. ..................... 514/210; 540/302
[58] Field of Search ........................ 514/710; 540/302

[56] References Cited

U.S. PATENT DOCUMENTS

| | | | |
|---|---|---|---|
| 4,260,627 | 4/1981 | Christensen et al. | 424/272 |
| 4,465,632 | 8/1984 | Christensen et al. | 260/245.2 |
| 4,543,257 | 9/1985 | Cama et al. | 514/210 |

OTHER PUBLICATIONS

L. D. Cama et al., Total Synthesis of Thienamycin Analgos-III, *Tetrahedron* 39, 2531 (1983).
R. N. Guthikonda, et al., Structure Activity Relationships in the 2-Arylcarbapenem Series, *J. Med. Chem.*, 30, 871 (1987).

*Primary Examiner*—Robert Gerstl
*Attorney, Agent, or Firm*—William H. Nicholson; Hesna J. Pfeiffer; John W. Harbour

[57] ABSTRACT

Carbapenems of the formula

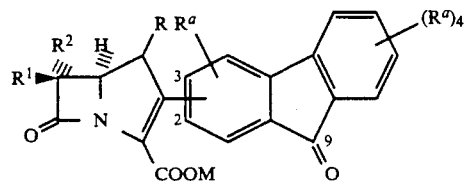

wherein either the 2-fluoren-9-one or 3-fluoren-9-one is attached at the 2-position of the carbapenem are useful antibacterial agents.

19 Claims, No Drawings

2-(9-FLUORENONYL)-CARBAPENEM ANTIBACTERIAL AGENTS

BACKGROUND OF THE INVENTION

The present invention relates to antibacterial agents of the carbapenem class, in which the 2-position sidechain is characterized by a fluoren-9-one moiety, substituted by various anionic and neutral substituents, as described in more detail further below.

Thienamycin was an early carbapenem antibacterial agent having a broad spectrum; it has the following formula:

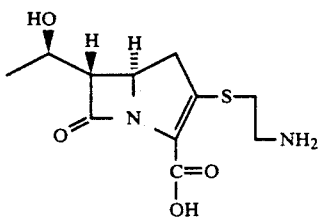

Later, N-formimidoyl thienamycin was discovered; it has the formula:

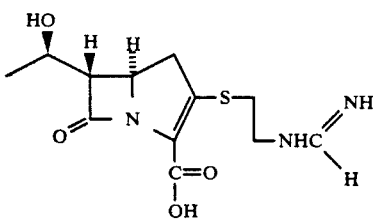

The 2-(9-fluorenonyl)-carbapenems of the present invention are not characterized by a broad antibacterial spectrum such as that of thienamycin or N-formimidoyl thienamycin. Rather, their spectrum of activity is largely limited to gram postive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Morever, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

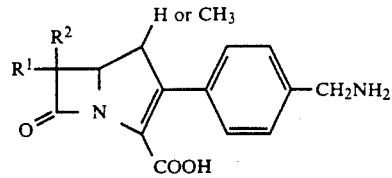

However, there is no description or suggestion of a 9-fluorenonyl 2-substituent such as characterizes the compounds of the present invention, nor is there any suggestion of the surprisingly better anti-MRSA/MRCNS activity of the compounds of the present invention.

EP-A-0277 743 describes a particular class of compounds of the formula:

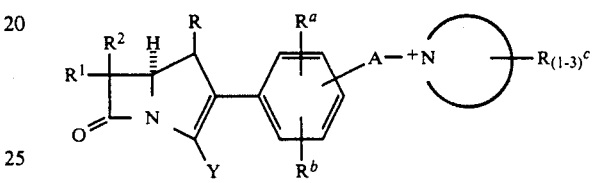

but this limited teaching in no way suggests the totally different compounds of the present invention, nor their surprisingly better anti-MRSA/MRCNS activity.

SUMMARY OF THE INVENTION

The present invention provides novel carbapenem compounds of the formula:

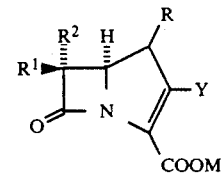

wherein:
Y is:

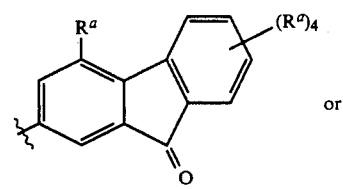

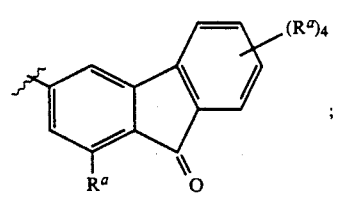

R is H or $CH_3$;
$R^1$ and $R^2$ are independently H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$, or $(CH_3)_3C(F)-$;

$R^a$ are independently selected from the radicals set out below, provided that no more than four $R^a$ substituents are other than hydrogen:

(a) hydrogen;
(b) a trifluoromethyl group: —$CF_3$;
(c) a halogen atom: —Br, —Cl, —F, or —I;
(d) $C_1$–$C_4$ alkoxy radical: —$OC_{1-4}$ alkyl, wherein the alkyl is optionally mono-substituted by $R^q$, where $R^q$ is a member selected from the group consisting of —OH, $OCH_3$—, —CN, —$C(O)NH_2$, —OC(O)$NH_2$, CHO, —OC(O)N($CH_3$)$_2$, —$SO_2NH_2$, —$SO_2N(CH_3)_2$, —$SOCH_3$, —$SO_2CH_3$, —F, —$CF_3$, —$COOM^a$, (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);
(e) a hydroxy group: —OH;
(f) a carbonyloxy radical of formula —O(C=O)$R^s$, where
$R^s$ is $C_1$–$C_4$ alkyl or phenyl, each of which is optionally mono-substituted by $R^q$ as defined above;
(g) a carbamoyloxy radical of formula —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together form a 2- to 4-membered alkylidene radical, interrupted by —O—, —S—, —S(O)— or —S(O)$_2$— to form a ring (where the ring is optionally mono-substituted with $R^q$ as defined above);
(h) a sulfur radical: —S(O)$_n$—$R^s$ where n=0–2, and $R^s$ is defined above;
(i) a sulfamoyl group; —$SO_2N(R^y)R^z$ where $R^y$ and $R^z$ are as defined above;
(j) azido: $N_3$;
(k) a formamido group: —N($R^t$)(C=O)H, where $R^t$ is H or $C_{1-4}$ alkyl, and the alkyl thereof is optionally mono-substituted by $R^q$ as defined above;
(l) a ($C_1$–$C_4$ alkyl)carbonylamino radical: —N($R^t$)(C=O)$C_{1-4}$ alkyl, where $R^t$ is as defined above, and the alkyl group is also optionally mono-substituted by $R^q$ as defined above;
(m) a ($C_1$–$C_4$ alkoxy)carbonylamino radical: —N($R^t$)(C=O)O$C_{1-4}$ alkyl, where $R^t$ is as defined above, and the alkyl group is also optionally mono-substituted by $R^q$ as defined above;
(n) a ureido group: —N($R^t$)(C=O)N($R^y$)$R^z$ where $R^t$, $R^y$ and $R^z$ are as defined above;
(o) a sulfonamido group: —N($R^t$)$SO_2R^s$, where $R^s$ amd $R^t$ are as defined above;
(p) a cyano group: —CN;
(q) a formyl or acetalized formyl radical: —(C=O)H or —CH(OCH$_3$)$_2$;
(r) ($C_1$–$C_4$ alkyl)carbonyl radical wherein the carbonyl is acetalized: —C(OCH$_3$)$_2C_{1-4}$ alkyl, where the alkyl is optionally mono-substituted by $R^q$ as defined above;
(s) carbonyl radical: —(C=O)$R^s$, where $R^s$ is as defined above;
(t) a hydroximinomethyl radical in which the oxygen or carbon atom is optionally substituted by a $C_1$–$C_4$ alkyl group: —(C=NO$R^z$)$R^y$ where $R^y$ and $R^z$ are as defined above, except they may not be joined together to form a ring;
(u) a ($C_1$–$C_4$ alkoxy)carbonyl radical: —(C=O)O$C_{1-4}$ alkyl, where the alkyl is optionally mono-substituted by $R^q$ as defined above;
(v) a carbamyl radical: —(C=O)N($R^y$)$R^z$ where $R^y$ and $R^z$ are defined above;
(w) an N-hydroxycarbamoyl or N($C_{1-4}$ alkoxy)carbamoyl radical in which the nitrogen atom may be additionally substituted by a $C_1$–$C_4$ alkyl group: —(C=O)—N(O$R^y$)$R^z$ where $R^y$ and $R^z$ are as defined above, except they may not be joined together to form a ring;
(x) a thiocarbamoyl group: —(C=S)N($R^y$)$R^z$ where $R^y$ and $R^z$ are as defined above;
(y) carboxyl: —COO$M^b$, where $M^b$ is as defined above;
(z) thiocyanate: —SCN;
(aa) trifluoromethylthio: —$SCF_3$;
(ab) tetrazolyl, where the point of attachment is the carbon atom of the tetrazole ring and one of the nitrogen atoms is mono-substituted by hydrogen, an alkali metal or a $C_1$–$C_4$ alkyl optionally substituted by $R^q$ as defined above;
(ac) an anionic function selected from the group consisting of:
phosphono [P=O(O$M^b$)$_2$];
alkylphosphono {P=O(O$M^b$)—[O($C_1$–$C_4$ alkyl)]};
alkylphosphinyl [P=O(O$M^b$)—($C_1$–$C_4$ alkyl)];
phosphoramido [P=O(O$M^b$)N($R^y$)$R^z$ and P=O(O$M^b$)NH$R^x$];
sulfino (SO$_2M^b$);
sulfo (SO$_3M^b$);
acylsulfonamides selected from the structures CON$M^b$SO$_2R^x$, CON$M^b$SO$_2$N($R^y$)$R^z$, SO$_2$N$M^b$CON($R^y$)$R^z$; and SO$_2$N$M^b$CN, where
$R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;
(ad) $C_5$–$C_7$ cycloalkyl group in which one of the carbon atoms in the ring is replaced by a heteroatom selected from O, S, NH, or N($C_1$–$C_4$ alkyl) and in which one additional carbon may be replaced by NH or N($C_1$–$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;
(ae) $C_2$–$C_4$ alkenyl radical, optionally mono-substituted by one of the substituents (b) to (ad) above and phenyl which is optionally substituted by $R^q$ as defined above;
(af) $C_2$–$C_4$ alkynyl radical, optionally mono-substituted by one of the substituents (b) to (ad) above;
(ag) $C_1$–$C_4$ alkyl radical;
(ah) $C_1$–$C_4$ alkyl mono-substituted by one of the substituents (b)–(ad) above; or (ai) a 2-oxazolidinonyl moiety in which the point of attachment is the nitrogen atom of the oxazolidinone ring, the ring oxygen atom is optionally replaced by a heteroatom selected from S and NR' (where R' is as defined above) and one of the saturated carbon atoms of the oxazolidinone ring is optionally mono-substituted by one of the substituents (b) to (ah) above;

M is:
(i) hydrogen;
(ii) a pharmaceutically acceptable esterifying group or removable carboxyl protecting group; or
(iii) an alkali metal or other pharmaceutically acceptable cation.

DETAILED DESCRIPTION OF THE INVENTION

The manufacture of compounds of Formula I may be carried out in a three-stage synthesis scheme followed by removal of protecting groups. The objective of the first synthesis stage is to produce a base fluoren-9-one compound which may be converted to the two-position substituent of the carbapenem of Formula I. The objective of the second synthesis stage is to substitute the fluoren-9-one with the desired $R^a$. The objective of the third synthesis stage is to attach the base fluoren-9-one to the carbapenem. This third synthesis stage may be performed after the first synthesis stage or after the second synthesis stage according to the nature of the various $R^a$ substituents.

Flow Sheets A, B, C and D demonstrate suggested first stage syntheses. Flow Sheets L and M demonstrate two alternative third stage syntheses. The second stage synthesis varies according to the selected $R^a$ group and suggested methods are shown in Flow Sheets E-K.

The synthesis of the 1-, 5-, 6-, 7- or 8-substituted fluorenones are described in the schemes below (Flow Sheets A, B and C). The general route involves the preparation of a suitably substituted biphenyl which contains the 2-carboxylic acid group needed for the ring closure to generate the desired fluoren-9-one ring system, as well as other functional groups for further elaboration to the desired fluoren-9-one and the functionality needed for coupling to the carbapenem.

Flow Sheet D suggests a route to the preparation of a 1,7-disubstituted fluoren-9-one using similar chemistry. By altering the substitution pattern on D2 and D4 different disubstituted fluorenones can be obtained. The methyl carboxylate of D9 or D10 can be converted to a hydroxymethyl, aldehyde, carboxamide or nitrile substituent, after suitable protection of the hydroxymethyl group, when necessary, to give the desired disubstituted fluoren-9-one which is then coupled to the carbapenem as described in Flow Sheets L and M for the monosubstituted analogs.

FLOW SHEET A

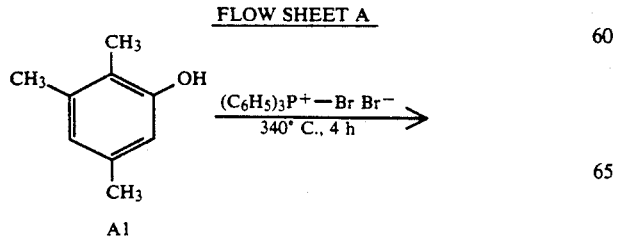

FLOW SHEET A
-continued

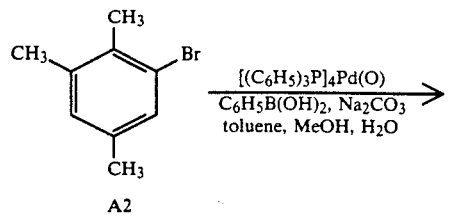

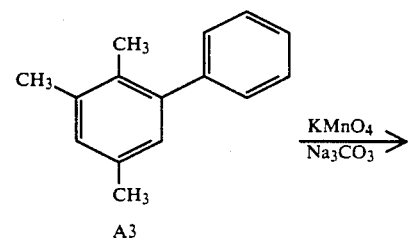

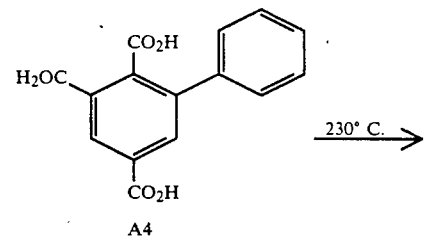

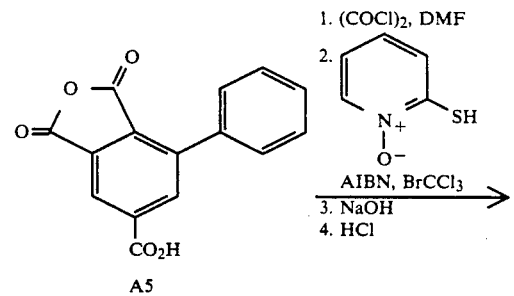

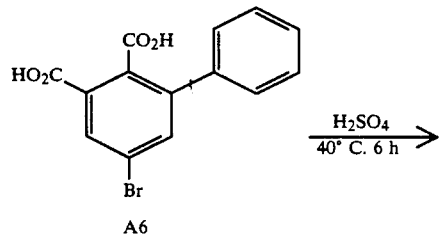

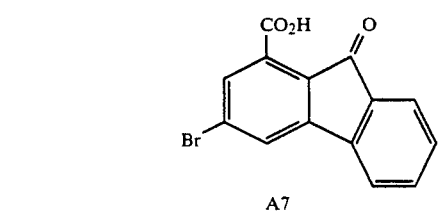

FLOW SHEET B
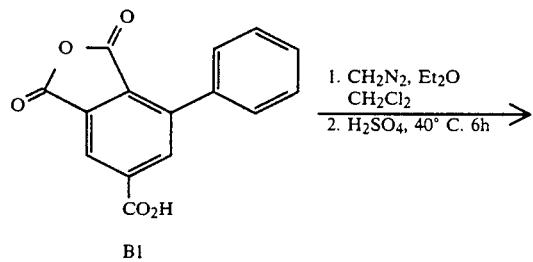
B1
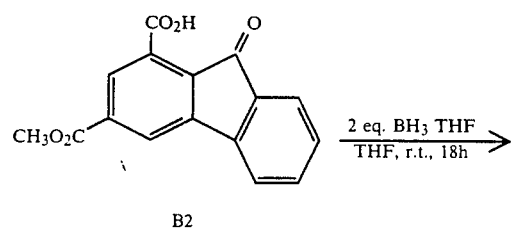
B2
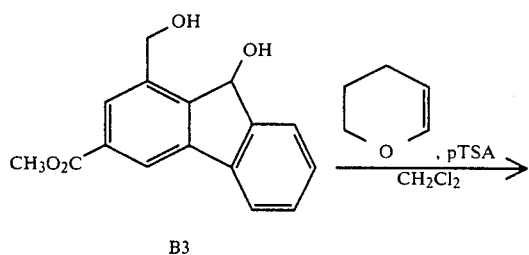
B3
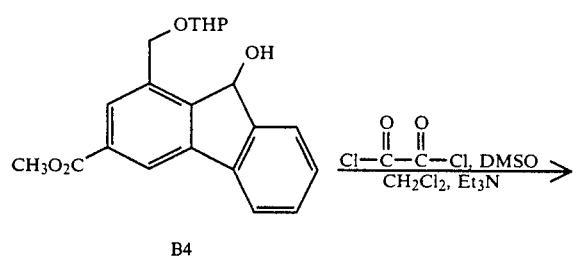
B4
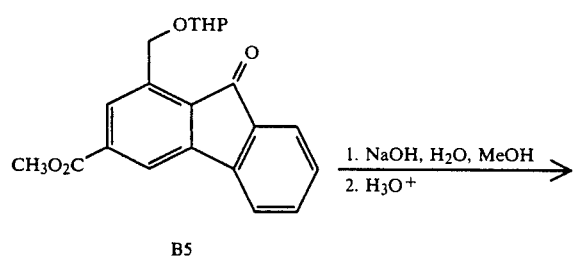
B5
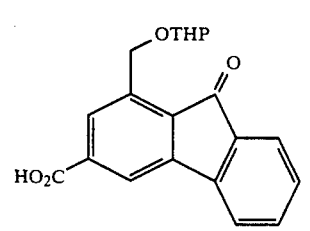
B6
FLOW SHEET C
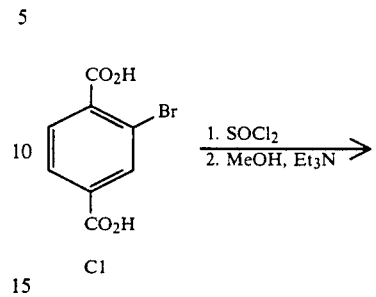
C1
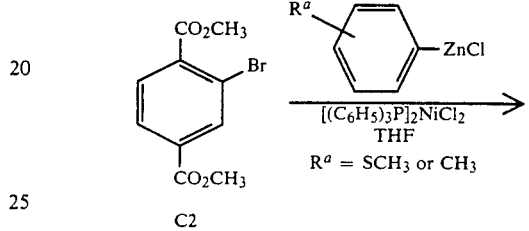
C2
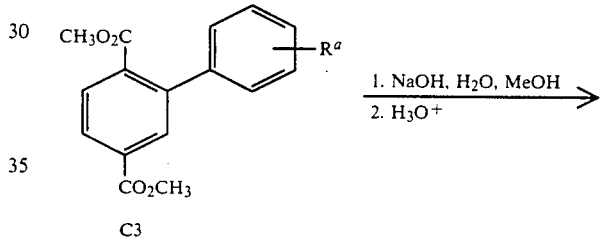
C3
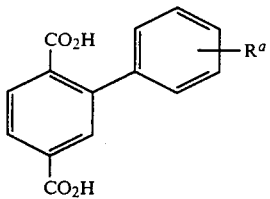
C4
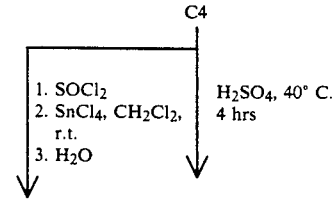
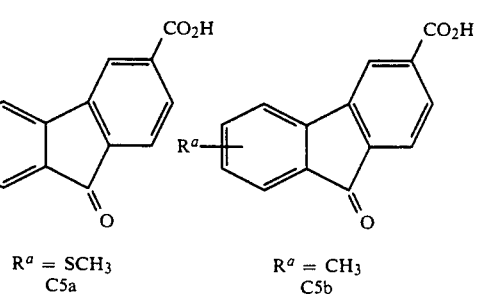
$R^a$ = SCH$_3$
C5a
$R^a$ = CH$_3$
C5b 5,025,007
9
FLOW SHEET D
10
-continued
FLOW SHEET D
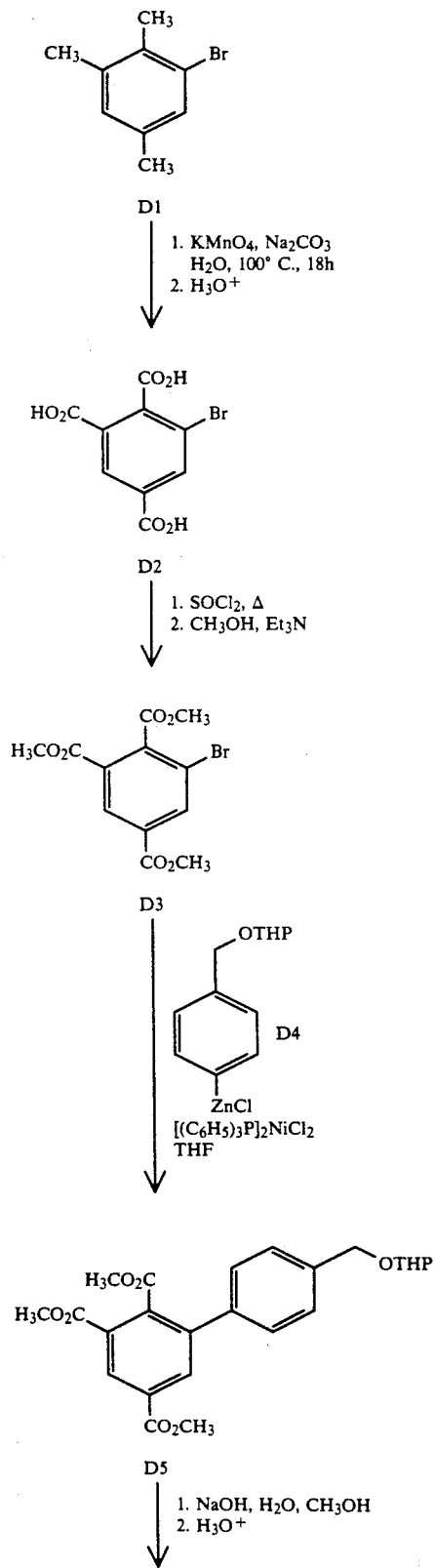
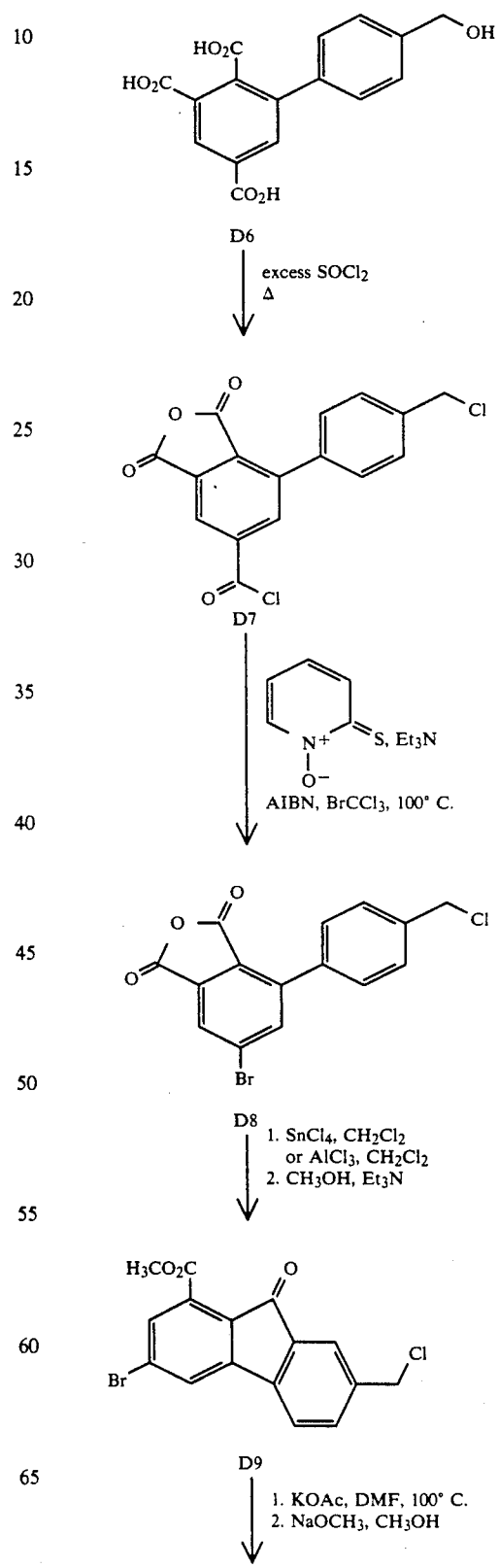

-continued
FLOW SHEET D
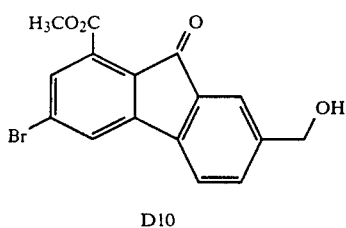
D10
FLOW SHEET E
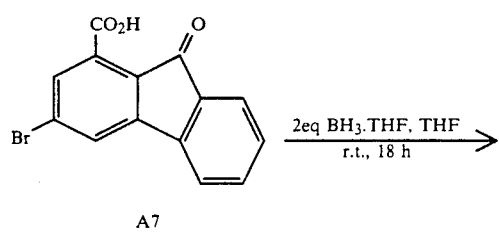
A7
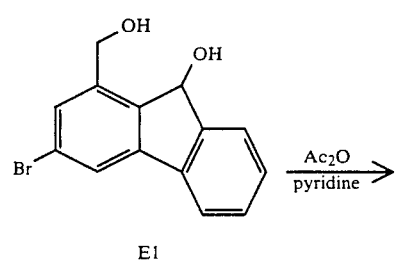
E1
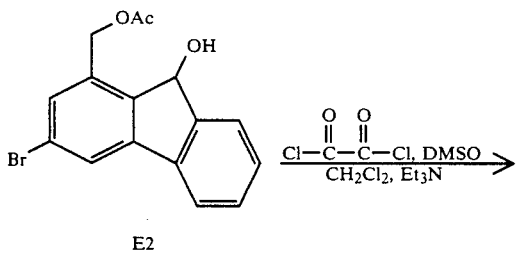
E2
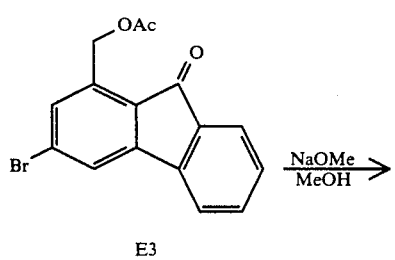
E3
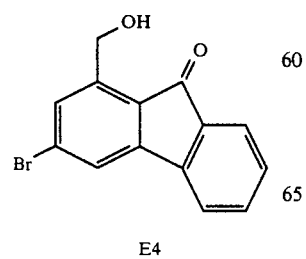
E4
FLOW SHEET F
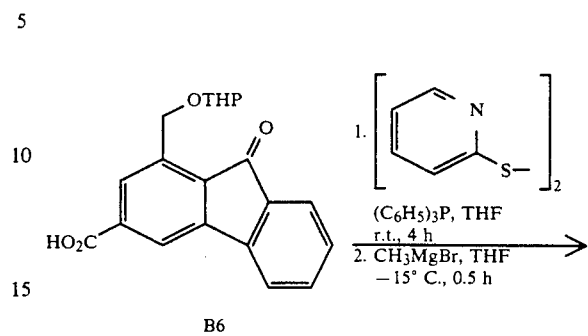
B6
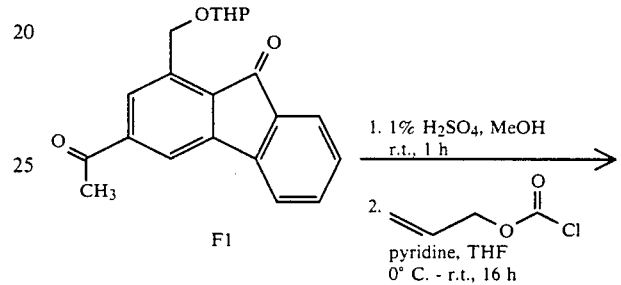
F1
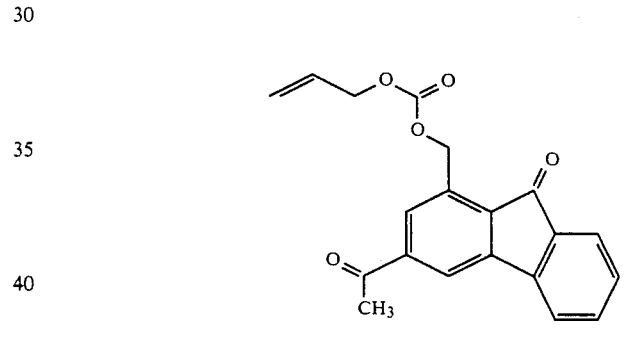
F2a
FLOW SHEET G
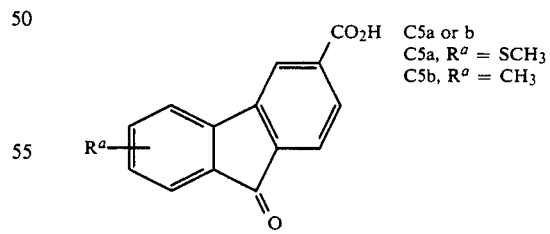
C5a or b
C5a, $R^a$ = SCH$_3$
C5b, $R^a$ = CH$_3$
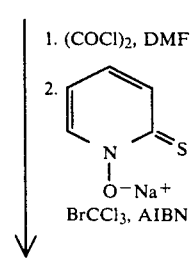

-continued
FLOW SHEET G
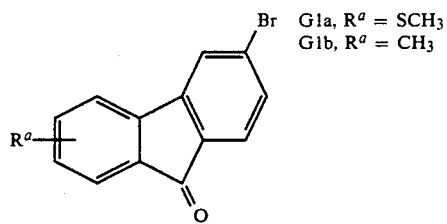
FLOW SHEET H
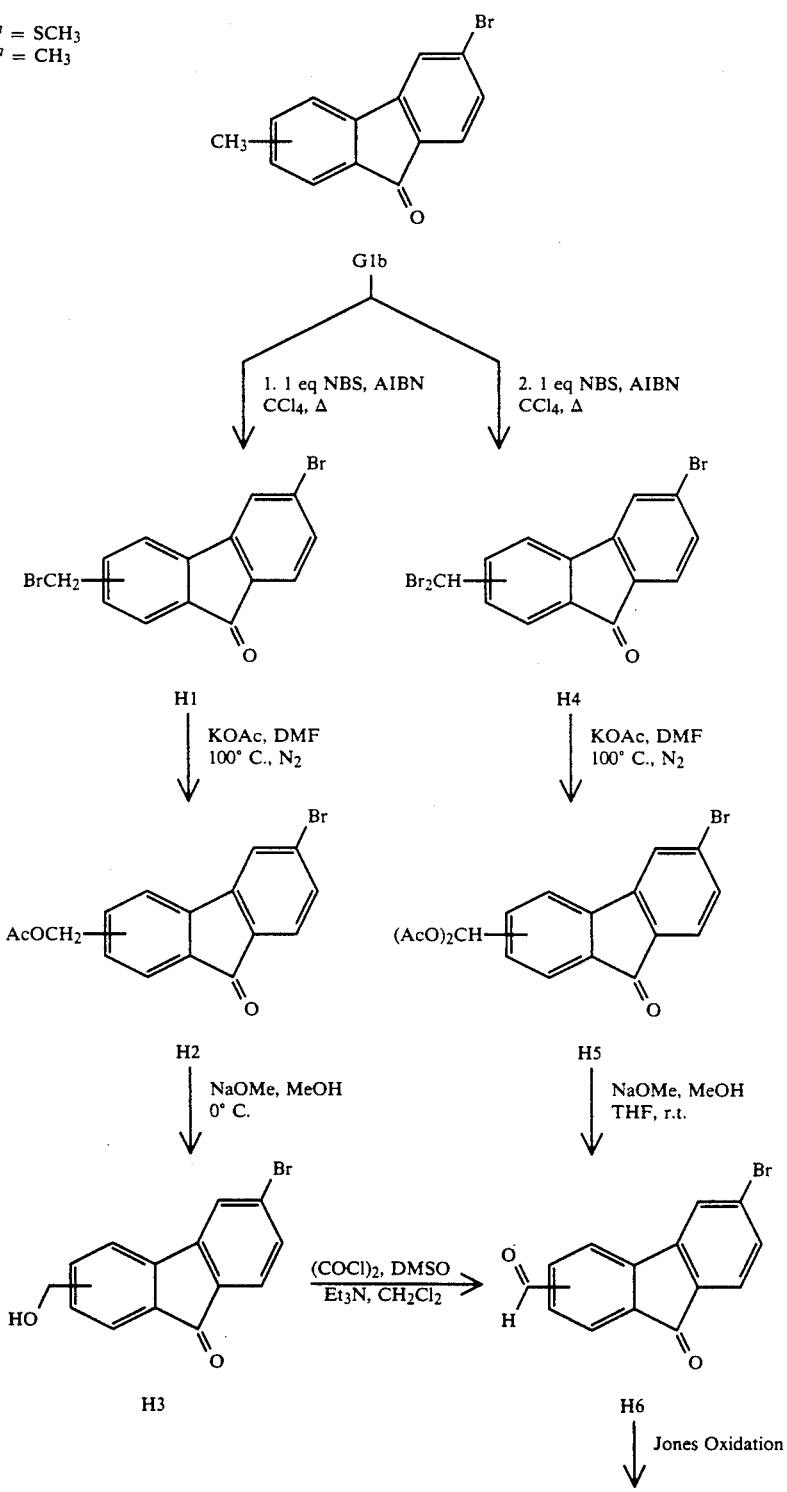

-continued
FLOW SHEET H
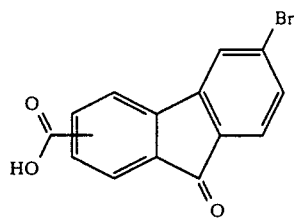
H7
FLOW SHEET I
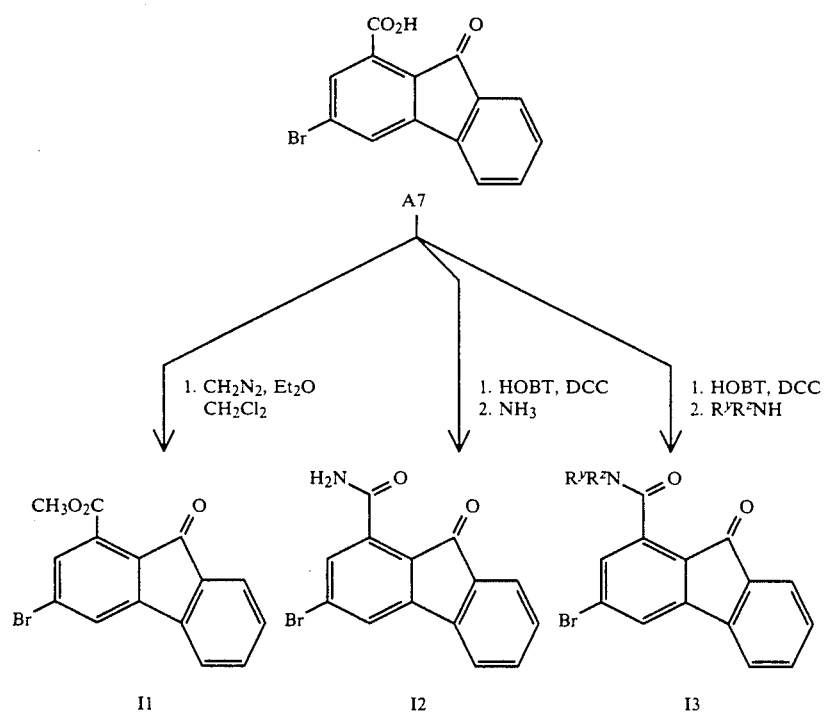
FLOW SHEET J
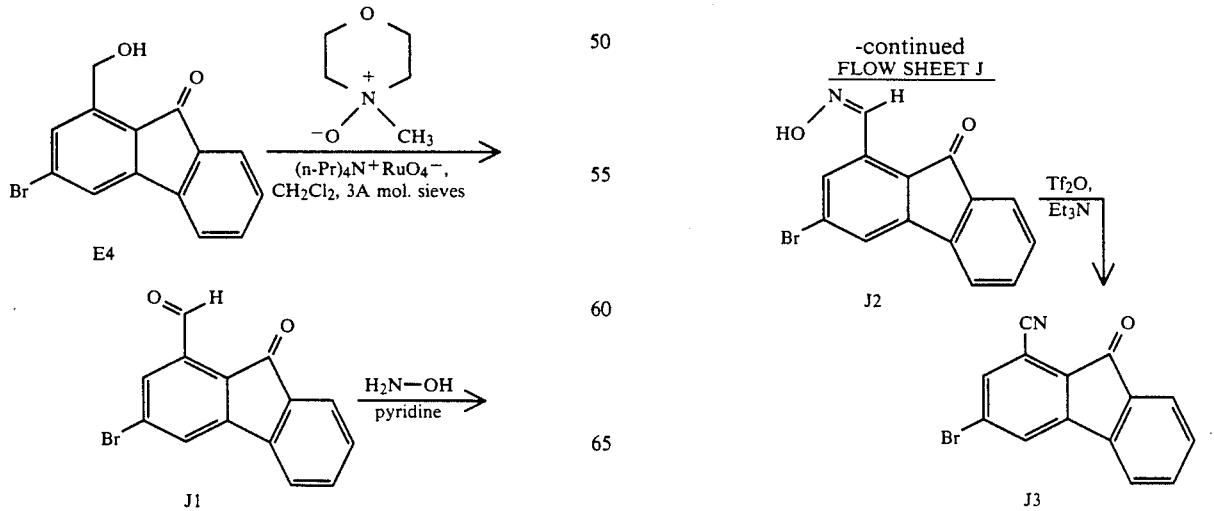

FLOW SHEET K
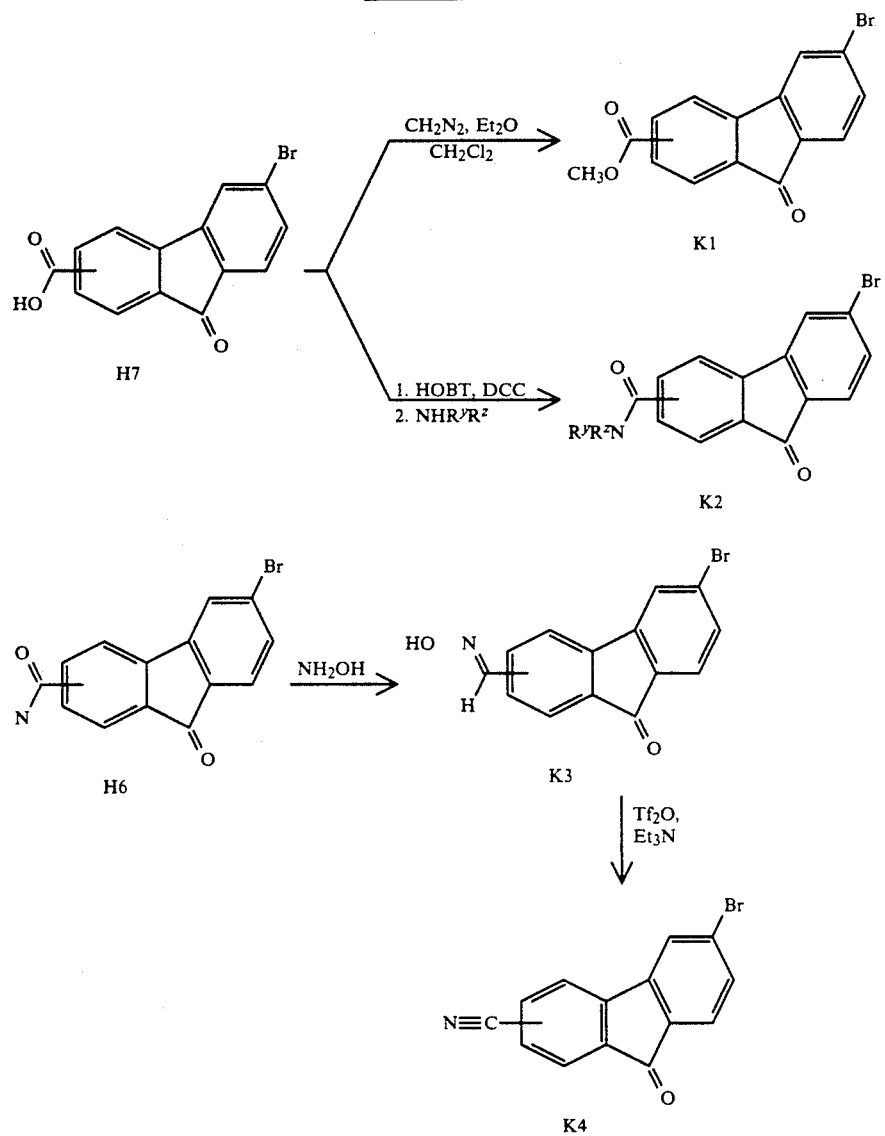
FLOW SHEET L
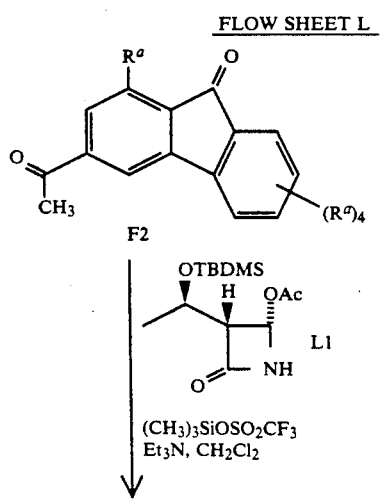
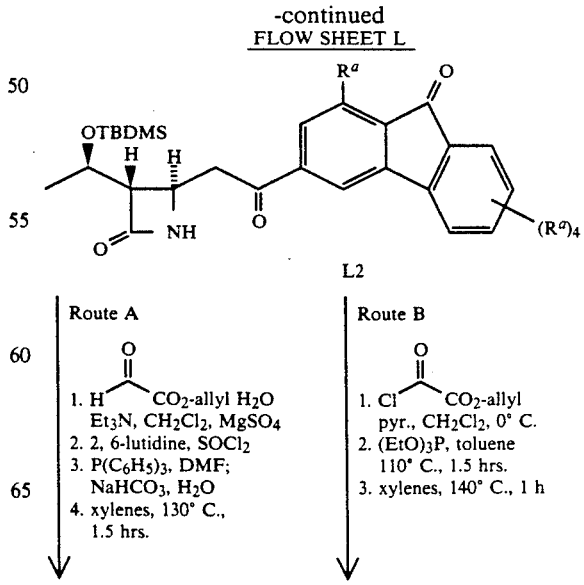

-continued
FLOW SHEET L

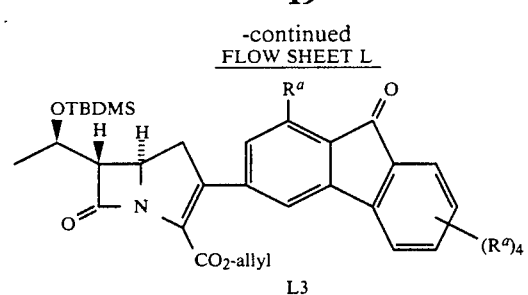

FLOW SHEET M

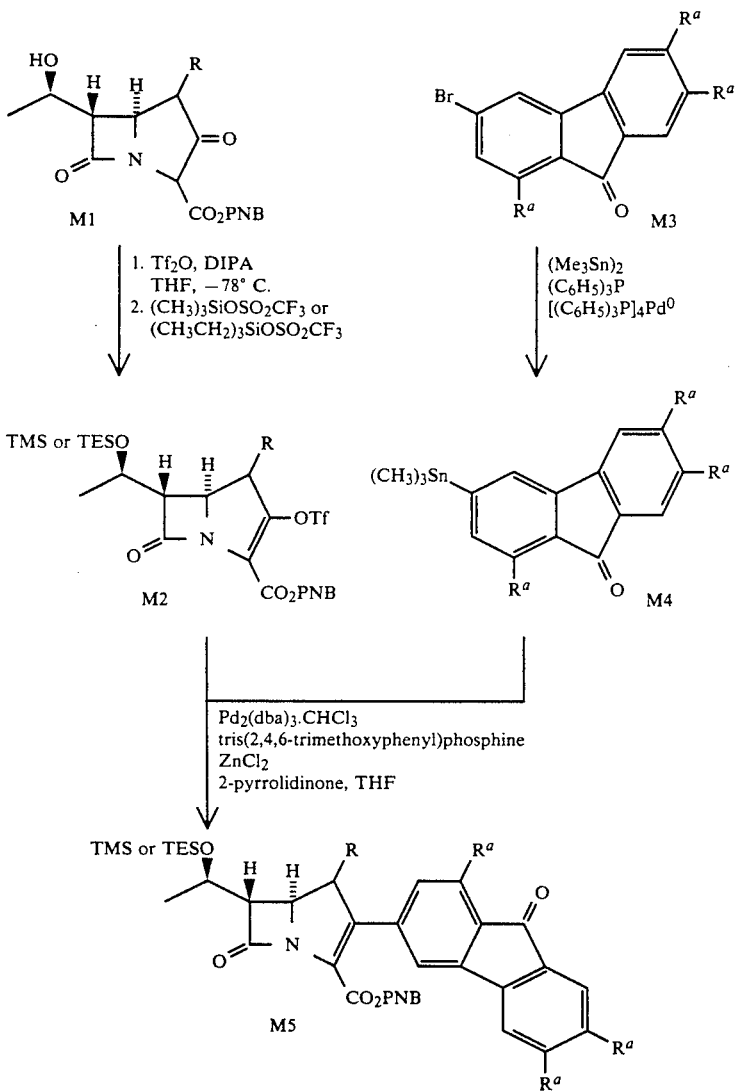

(1982); K. Hirai, Y. Iwano, and K. Fujimoto, *Heterocycles*, 17, 201 (1982)] using Lewis acid catalysis to give the azetidinone intermediate L2. The azetidinone, L2, can be cyclized to a carbapenem, according to Route B, by acylation of the azetidinone nitrogen with allyl oxalyl chloride and reaction of the resulting oxalimide with triethylphosphite to give a ylide intermediate which on heating in xylene at 90° to 140° C. with or without a small amount of hydroquinone, from 1 to 4 hours, gives the carbapenem L3. Alternatively, cyclization can be carried out according to Route A by condensation of L2 with allyl glyoxylate, chlorination of the resulting hemiaminal with thionyl chloride - 2,6-lutidine, reaction with triphenylphosphine followed by sodium bicarbonate and finally cyclization of the ylide intermediate thus produced by heating in xylene at 90° to 140° C. for 1 to 4 hours to give carbapenem L3. It is on an intermediate like L3 that final elaboration of the substituent $R^a$ from a precursor substituent such as hydroxymethyl may be accomplished, if necessary. Removal of the protecting groups then provides the final compound of Formula I. Such final elaboration and deprotection is described in further detail below.

The desired fluorenone, produced in the first or second synthetic stage, is attached to the carbapenem in the third stage using one of two possible routes: (1) coupling to an acetoxyazetidinone intermediate followed by Wittig cyclization to the carbapenem; or (2) direct coupling to a carbapenem triflate. Flow Sheet L describes the first method and Flow Sheet M describes the direct coupling to the carbapenem.

Referring to Flow Sheet L, the silyl enol ether of an appropriately substituted 3-acetylfluoren-9-one such as F2 is coupled to the known azetidinone L1 [P. J. Reider and E. J. Grabowski, *Tetrahedron Letters*, 23, 2293

Use of the isomeric 2-methylcarbonyl F2 in Flow Sheet L provides the corresponding 2-fluorenone derivative of the carbapenem L3, where attachment of the carbapenem is at the 2-position of the fluorenone. The isomeric 2-methylcarbonyl F2 is obtained by the use of the appropriately substituted biphenyl in the steps outlined in Flow Sheets A, B, C, D, E, F, G, H, I, J, and K.

Flow Sheet M shows an alternative third stage synthesis, i.e. attachment of the base fluorenone to the 2-position of the carbapenem. This synthesis involves a palladium catalyzed cross-coupling reaction between a carbapenem triflate and a suitably substituted arylstannane, a process which is described in U.S. patent application Ser. No. 485,096 filed Feb. 26, 1990. In order to apply this synthesis, it is first necessary to modify the bromofluoren-9-one (e.g. M3) to the trimethylstannylfluoren-9-one (e.g. M4). This is accomplished by reacting the bromo compound, hexamethylditin, tetrakis(triphenylphosphine)palladium(0) and triphenylphosphine in toluene at 110° C. Referring to Flow Sheet M, the 2-oxocarbapenam M1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in a polar aprotic solvent, such as tetrahydrofuran. An organic nitrogen base, such as triethylamine and the like, is then added to the reaction solution followed immediately by a silylating agent, such as trimethylsilyl or triethylsilyl trifluoromethanesulfonate to provide the triflate intermediate M2. An aprotic polar coordinating solvent, such as DMF, 1-methyl-2-pyrrolidinone and the like, is added. This is followed by the addition of a palladium compound, such as tris(dibenzylideneacetone)dipalladium-chloroform, palladium acetate and the like, optionally a suitably substituted phenylphosphine, such as tris(4-methoxyphenyl)phosphine, tris(2,4,6-trimethoxyphenyl)phosphine and the like, and the stannane M4. A metal halide, such as lithium chloride, zinc chloride and the like, is added and the reaction solution is warmed to a suitable temperature, such as 0° C. to 50° C., and allowed to stir for a suitable amount of time such as from a few minutes to 48 hours. The carbapenem M5 is obtained by conventional isolation/purification methodology known in the art.

The corresponding 2-fluoren-9-one regioisomer of M5 can be prepared analogously by starting with the 2-bromofluoren-9-one corresponding to M3, which in turn is derived from appropriately substituted biphenyls by following the steps outlined in Flow Sheets A, B, C, D, E, F, G, H, I, J, and K.

Generally speaking, the milder conditions of the synthesis shown in Flow Sheet M allow for a wider range of functional groups $R^a$ to be present when attaching the fluoren-9-one, than the synthesis illustrated in Flow Sheet L. However, in certain cases it is advantageous for the $R^a$ substituent(s) of the stannane M4 to be introduced in a protected or precursory form. Final elaboration of $R^a$ from a precursor substituent, e.g. hydroxymethyl, may be accomplished on carbapenem intermediate M5. Removal of protecting groups then provides the final compound of Formula I. Such final elaboration and deprotection is described further below.

Azetidin-2-one, L1 is a well known compound in the production of carbapenems. Diverse synthetic schemes useful to make L1 may be imagined by the skilled artisan. The steps for preparing this intermediate are analogous to the procedures described in P. J. Reider and E. J. Grabowski, *Tetrahedron Letters*, 23, 2293 (1982) and K. Hirai, Y. Iwano and K. Fujimoto, *Heterocycles*, 17, 201 (1982).

The steps for preparing the 2-oxocarbapenam intermediate, M1, are well known in the art and are explained in ample detail by D. G. Melillo, et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. Nos. 4,269,772, 4,350,631, 4,383,946 and 4,414,155 all assigned to Merck and Co., Inc.

The general synthesis description depicted above in the Flow Sheets shows a protected 1-hydroxyethyl substitution on the 6-position of the carbapenem. After final deprotection, a 1-hydroxyethyl substituent is obtained, which is preferred in most cases. However, it has been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanraku Ocean).

In the compounds of the present invention, the $R^a$ substituents are either neutral or anionic in nature, and are distinguishable from cationic substituents chemically and with respect to the biological properties which they confer. In related compounds, it has been found that the neutral or anionic substituted compounds afford greater water solubility and reduced potential for CNS side effects. Substituents which tend to confer improved water solubility on the overall compound have been found useful, since they are contemplated to thereby improve the transport of the compound involved. Although a substantial number and range of neutral and anionic substituents have been described herein, all of these are contemplated to be a part of the present invention based on the biological performance of substituents related in terms of their medicinal chemistry.

The compounds of the present invention, may contain more than one neutral or anionic substituent, with this substitution pattern there can be a combination of desired attributes in the final overall molecule not attainable with a single substituent, i.e., improved anti-MRSA/MRCNS activity together with enhanced water solubility.

In preferred compounds of Formula I, $R^1$ is hydrogen. More preferably $R^1$ is hydrogen and $R^2$ is (R)—CH$_3$CH(OH)— or (R)—CH$_3$CH(F)—. Most preferably $R^1$ is hydrogen and $R^2$ is (R)—CH$_3$CH(OH)—. While R=hydrogen is usually preferred, there are instances in which R=CH$_3$ may provide improved chemical stability, water solubility, or pharmacokinetic behavior. The substituent R=CH$_3$ may be of either configuration, i.e., the α or β-stereoisomer. Additionally, in preferred compounds of Formula I, in total, up to two $R^a$ substituents in either the 1-, 6-, 7- or 8-positions of the 3-fluoren-9-one or the 4-, 6- or 7-positions of the 2-fluoren-9-one are other than hydrogen. More preferably, Y is b, the 3-fluoren-9-onyl substituent.

Among preferred $R^a$ are (C$_1$-C$_4$)-alkyl mono-substituted with hydroxy, such as, hydroxymethyl; formyl;

carboxy, such as —COOK; carbamoyl, such as, —CONH$_2$; hydroximinomethyl, such as, —CH=NOH or cyano.

In regard to this preferred substitution, the hydroxymethyl may be obtained in the 1-, 6- and 7-positions of the fluoren-9-one as shown in Flow Sheets E and H. The hydroxymethyl may be obtained in positions 5 or 8 of the fluoren-9-one by employing the appropriately substituted starting material G1b in Flow Sheet H. The carboxy-substituted fluorenon-9-one A7 and the isomeric methyl-fluoren-9-ones G1b serve as precursor starting materials in Flow Sheets E and H respectively. Thus, proceeding as shown in Flow Sheets A, C, E, G and H the isomeric hydroxymethyl-substituted fluoren-9-ones may be produced.

Proceeding according to Flow Sheet M, and employing E4 or isomeric H3 as starting material M3, the corresponding hydroxymethyl substituted M5 may be obtained. Alternatively, elaboration of the hydroxymethyl group into another preferred R$^a$ substituent as described below may be carried-out prior to coupling of the fluoren-9-one to the carbapenem. In certain instances, depending on the particular R$^a$ group being sought, such elaboration may also be performed on M5 after attachment of the fluoren-9-one side chain to the carbapenem. As previously described, the corresponding 2-fluoren-9-one regioisomers of M5 may be prepared analogously by starting with the 2-bromofluoren-9-ones corresponding to E4 and isomeric H3, which in turn may be derived by employing the appropriate starting materials in Flow Sheets A and C.

The preferred formyl substitution on the fluoren-9-one may be obtained from the hydroxymethyl substitution just described by a Swern oxidation. For example, E4 or H3 is oxidized in methylene chloride at from −70° C. to room temperature employing oxalyl chloride-dimethyl sulfoxide, followed by triethylamine (Flow Sheet H). Alternatively, this oxidation may be conveniently carried-out with N-methylmorpholine-N-oxide and a catalytic amount of tetra-n-propylammonium perruthenate in methylene chloride at room temperature (Flow Sheet J). Obviously, the position of the resultant formyl substitution will depend upon the position of the hydroxymethyl substitution in E4 or H3.

The preferred —CH=NOH substitution on the fluoren-9-one may be conveniently obtained from the formyl substitution just described. This is accomplished simply by exposing the formyl substituted compound to hydroxylamine in an appropriate solvent at room temperature (Flow Sheets J and K).

The preferred cyano substitution on the fluoren-9-one may be obtained from the —CH=NOH substitution just described. The —CH=NOH substituted compound is dehydrated with triflic anhydride and triethylamine in a solvent at −70° C. (Flow Sheets J and K).

The preferred —COOK substitution on the fluoren-9-one may be obtained from the hydroxymethyl substituted E4 or H3 described above. For example, an isomeric H3 is oxidized with Jones reagent to convert the hydroxymethyl substituent into a carboxylic acid group. The oxidation with Jones reagent may be incompatible with the carbapenem and thus is optimally performed prior to coupling with the carbapenem. An alternative procedure is illustrated in Flow Sheet H and involves the oxidation of a methyl by dibromination, acetolysis, hydrolysis and finally Jones oxidation to the acid, H7. Prior to coupling with the carbapenem, the carboxy is advantageously protected as its p-nitrobenzyl or allyl ester. Protection is carried out by alkylating with p-nitrobenzyl or allyl bromide and triethylamine, in dimethylformamide. Deprotection of the allyl ester following coupling is carried out by palladium catalyzed deallylation in a solution containing potassium 2-ethylhexanoate, while the p-nitrobenzyl ester can be removed by hydrogenation over palladium on carbon in presence of potassium bicarbonate. Deprotection in such a manner yields the desired potassium salt.

The preferred carbamoyl substitution on the fluoren-9-one may be obtained from E4 or H3 by oxidizing the hydroxymethyl with Jones reagent to the corresponding carboxylic acid as described above. This carboxy is converted to —CONH$_2$ by sequentially contacting with 1-ethyl-3-(3-dimethyl-aminopropyl)carbodiimide hydrochloride, 1-hydroxybenzotriazole, and ammonia in an organic solvent at room temperature (Flow Sheets I and K). Alternatively, the carboxylic acid substituent may be reacted with 1,1'-carbonyldiimidazole in an aprotic polar solvent, such as tetrahydrofuran followed by treatment with aqueous ammonia to give the carboxamide. Substituted amides may of course be obtained by replacing ammonia with the corresponding substituted amine.

In addition to or including the above, preferred R$^a$ substituents include:

| | |
|---|---|
| —OCH$_3$ | —OCH$_2$CO$_2$Na |
| —OCH$_2$CH$_2$OH | —CF$_3$ |
| —F | —Cl |
| —Br | —I |
| —OH | —OCOCH$_3$ |
| —OCONH$_2$ | —SCH$_3$ |
| —SOCH$_3$ | —SO$_2$CH$_3$ |
| —SCH$_2$CH$_2$OH | —SOCH$_2$CH$_2$OH |
| —SO$_2$NH$_2$ | —SO$_2$N(CH$_3$)$_2$ |
| —NHCHO | —NHCOCH$_3$ |
| —NHCO$_2$CH$_3$ | —NHSO$_2$CH$_3$ |
| —CN | —CHO |
| —COCH$_3$ | —COCH$_2$OH |
| —CH=NOH | —CH=NOCH$_3$ |
| —CH=NOCH$_2$CO$_2$H | —CH=NOCMe$_2$CO$_2$H |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$H |
| —CONHOH | —CONHCH$_3$ |
| -tetrazolyl | —CO$_2$Na |
| —SCF$_3$ | —PO$_3$NaH |
| —CONHSO$_2$Ph | —CONHSO$_2$NH$_2$ |
| —SO$_3$Na | —SO$_2$NHCN |
| —SO$_2$NHCONH$_2$ | —CH=CHCN |
| —CH=CHCONH$_2$ | —CH=CHCO$_2$Na |
| —C≡C—CONH$_2$ | —C≡C—CN |
| —CH$_2$OH | —CH$_2$N$_3$ |
| —CH$_2$CO$_2$Na | —SO$_2$CH$_2$CH$_2$OH and |
| —CH$_2$I. | |

In the preparation methods described above, the carboxyl group at the 3-position and the hydroxyl group at the 8-position of the carbapenem remain blocked by protecting groups until the final product is prepared. Deblocking may be carried out in a conventional manner. For compounds prepared according to Flow Sheet L, deprotection of the ester at 3-position may be carried out in a palladium catalyzed reaction in a solution containing potassium 2-ethylhexanoate or, alternatively, another suitable nucleophile such as pyrrolidine, while the tert-butyldimethylsilyl group is removed by treatment with tetrabutylammonium fluoride in the presence of acetic acid. Alternatively, for those prepared via Flow Sheet M, deprotection is conducted sequentially.

Thus, compound M5 is exposed initially to aqueous acidic conditions, acetic acid or dilute HCl or the like, in an organic solvent such as tetrahydrofuran at 0° C. to 50° C. for from a few minutes to several hours. The resulting desilylated carbapenem may be isolated by conventional techniques, but is more conveniently taken into the final deprotection process. Thus, addition of an inorganic base such as $NaHCO_3$ or $KHCO_3$ and 10% Pd/C followed by hydrogenation provides for the removal of the p-nitrobenzyl protecting group and the formation of the final compound of Formula I.

The overall molecule must be electronically balanced. It is within the scope of this invention to utilize an anionic substituent, in which case it will be understood that it is necessary to provide a second counterion (cation) for the anionic substituent. However, it is well within the skill of a medicinal chemist, to whom there is available many suitable cationic counterions, to make such choices.

With reference to the above definitions, "alkyl" means a straight or branched chain aliphatic hydrocarbon radical.

The term "heteroatom" means N, S, or O, selected on an independent basis.

The term "heteroaryl" has been defined herein, in relation to the $R^x$ group, to have a specific and limited meaning, being only monocyclic. It is required that the monocyclic heteroaryl have at least one nitrogen atom, and optionally at most only two additional oxygen or sulfur heteroatom may be present. Heteroaryls of this type are pyrrole and pyridine (one N); and oxazole, thiazole or oxazine (one N+one O or one S). While additional nitrogen atoms may be present together with the first nitrogen and oxygen or sulfur, giving, e.g., a thiadiazole (two N's+one S), the preferred heteroaryls are those where *only* nitrogen heteroatoms are present when there is more than one. Typical of these are pyrazole, imidazole, pyrimidine and pyrazine (two N's) and triazine (three N's). The heteroaryl group of $R^x$ is always optionally mono-substituted by $R^q$, defined above, and substitution can be on one of the carbon atoms or one of the heteroatoms, although in the latter case certain substitutent choices may not be appropriate.

Listed in Tables I and II are specific compounds of the instant invention. It is understood that the stereochemistry of $R^2$ substituents which contain a chiral center (1-fluoroethyl or 1-hydroxyethyl) is the (R)-configuration in all of the listed compounds:

TABLE I

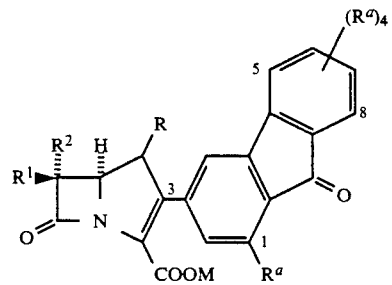

| # | R | $R^1$ | $R^2$ | M | $R^a$ | Ra position |
|---|---|---|---|---|---|---|
| 1 | —H | —H | —CH(OH)CH₃ | K⁺ | —OCH₃ | 1 |
| 2 | —H | —H | —CH(OH)CH₃ | Na⁺ | —OCH₂CO₂Na | 1 |
| 3 | —H | —H | —CH(OH)CH₃ | K⁺ | —OCH₂CH₂OH | 1 |
| 4 | —H | —H | —CH(OH)CH₃ | K⁺ | —CF₃ | 1 |
| 5 | —H | —H | —CH(OH)CH₃ | Na⁺ | —F | 1 |
| 6 | —H | —H | —CH(OH)CH₃ | Na⁺ | —Cl | 6 |
| 7 | —H | —H | —CH(OH)CH₃ | K⁺ | —Br | 7 |
| 8 | —H | —H | —CH₂OH | K⁺ | —I | 1,6 |
| 9 | —H | —H | —CH(OH)CH₃ | K⁺ | —OH | 1,6,7 |
| 10 | —H | —H | —CH(OH)CH₃ | Na⁺ | —OCOCH₃ | 6 |
| 11 | —H | —H | —CH(OH)CH₃ | Na⁺ | —OCONH₂ | 6 |
| 12 | —H | —H | —CH(OH)CH₃ | Na⁺ | —SCH₃ | 6 |
| 13 | —H | —H | —CH(F)CH₃ | K⁺ | —SOCH₃ | 7 |
| 14 | —CH₃ | —H | —CH(OH)CH₃ | Na⁺ | —SO₂CH₃ | 7 |
| 15 | —H | —H | —CH(OH)CH₃ | Na⁺ | —SCH₂CH₂OH | 7 |
| 16 | —H | —H | —CH(OH)CH₃ | Na⁺ | —SOCH₂CH₂OH | 7 |
| 17 | —H | —H | —CH(OH)CH₃ | K⁺ | —SO₂CH₂CH₂OH | 7 |
| 18 | —H | —H | —CH(OH)CH₃ | Na⁺ | —SO₂NH₂ | 1,7 |
| 19 | —H | —H | —CH(OH)CH₃ | K⁺ | —SO₂N(CH₃)₂ | 1,6 |
| 20 | —H | —H | —CF₂CH₃ | K⁺ | —NHCHO | 1,6 |
| 21 | —CH₃ | —H | —CH(OH)CH₃ | K⁺ | —NHCOCH₃ | 1,7 |
| 22 | —H | —H | —CH(OH)CH₃ | K⁺ | —NHCO₂CH₃ | 1,6 |
| 23 | —H | —H | —CH(OH)CH₃ | Na⁺ | —NHSO₂CH₃ | 1,7 |
| 24 | —H | —H | —CH(OH)CH₃ | Na⁺ | —CN | 6 |
| 25 | —H | —H | —CH(OH)CH₃ | K⁺ | —CHO | 7 |
| 26 | —H | —H | —CH(OH)CH₃ | K⁺ | —COCH₃ | 6 |
| 27 | —H | —H | —CH(OH)CH₃ | K⁺ | —COCH₂OH | 7 |
| 28 | —H | —H | —CH(OH)CH₃ | K⁺ | —CH=NOH | 6 |
| 29 | —H | —H | —CH(OH)CH₃ | Na⁺ | —CH=NOCH₃ | 7 |
| 30 | —H | —H | —CH(OH)CH₃ | K⁺ | —CH=NOCH₂CO₂K | 1 |
| 31 | —CH₃ | —H | —CH(OH)CH₃ | Na⁺ | —CH=NOCMe₂CO₂Na | 6 |
| 32 | —H | —H | —CH(OH)CH₃ | Na⁺ | —CH=NOCMe₂CO₂Me | 7 |
| 33 | —H | —H | —CH(OH)CH₃ | K⁺ | —CO₂CH₂CH₂OH | 1 |
| 34 | —H | —H | —CH(OH)CH₃ | Na⁺ | —CONH₂ | 6 |
| 35 | —H | —H | —CH(OH)CH₃ | K⁺ | —CONHCH₃ | 7 |
| 36 | —H | —H | —CH(OH)CH₃ | K⁺ | —CON(CH₃)₂ | 6 |

TABLE I-continued

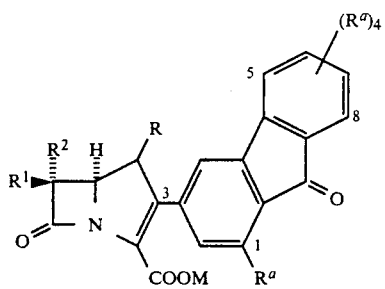

| # | R | R[1] | R[2] | M | R[a] | Ra position |
|---|---|---|---|---|---|---|
| 37 | —H | —H | —CH(OH)CH$_3$ | K$^+$ | —CONHCH$_2$CN | 7 |
| 38 | —CH$_3$ | —H | —CF$_2$CH$_3$ | Na$^+$ | —CINHCH$_2$CONH$_2$ | 1 |
| 39 | —H | —H | —CH(OH)CH$_3$ | K$^+$ | —CONHCH$_2$CO$_2$K | 6 |
| 40 | —H | —H | —CH(OH)CH$_3$ | Na$^+$ | —CONHOH | 7 |
| 41 | —H | —H | —CH(OH)CH$_3$ | Na$^+$ | —CONHOCH$_3$ | 1 |
| 42 | —H | —H | —CH(OH)CH$_3$ | Na$^+$ | —tetrazolyl | 6 |
| 43 | —H | —H | —CH$_2$OH | Na$^+$ | —CO$_2$Na | 1 |
| 44 | —H | —H | —CH(OH)CH$_3$ | Na$^+$ | —SCF$_3$ | 6 |
| 45 | —H | —H | —CH(OH)CH$_3$ | Na$^+$ | —PO$_2$NaH | 7 |
| 46 | —H | —H | —CH(OH)CH$_3$ | Na$^+$ | —CONHSO$_2$Ph | 1 |
| 47 | —CH$_3$ | —H | —CH(OH)CH$_3$ | Na$^+$ | —CONHSO$_2$NH$_2$ | 6 |
| 48 | —H | —H | —CH(OH)CH$_3$ | Na$^+$ | —SO$_3$Na | 6 |
| 49 | —H | —H | —CH(OH)CH$_3$ | Na$^+$ | —SO$_2$NHCN | 7 |
| 50 | —CH$_3$ | —H | —CH(F)CH$_3$ | Na$^+$ | —SO$_2$NHCONH$_2$ | 6 |
| 51 | —H | —H | —CH(OH)CH$_3$ | K$^+$ | —CH=CHCN | 1 |
| 52 | —H | —H | —CH(OH)CH$_3$ | K$^+$ | —CH=CHCONH$_2$ | 6 |
| 53 | —H | —H | —CH(OH)CH$_3$ | Na$^+$ | —CH=CHCO$_2$Na | 7 |
| 54 | —H | —H | —CH(OH)CH$_3$ | Na$^+$ | —C≡C—CONH$_2$ | 1 |
| 55 | —CH$_3$ | —H | —CH(OH)CH$_3$ | Na$^+$ | —C≡C—CN | 6 |
| 56 | —H | —H | —CH(OH)CH$_3$ | Na$^+$ | —CH$_2$OH | 1 |
| 57 | —H | —H | —CH(OH)CH$_3$ | Na$^+$ | —CH$_2$OH | 6 |
| 58 | —H | —H | —CH(OH)CH$_3$ | Na$^+$ | —CH$_2$OH | 7 |
| 59 | —H | —H | —CH$_2$CH$_3$ | K$^+$ | —CH$_2$N$_3$ | 6 |
| 60 | —H | —H | —CH(OH)CH$_3$ | Na$^+$ | —CH$_2$CO$_2$Na | 7 |
| 61 | —H | —H | —CH(OH)CH$_3$ | Na$^+$ | —CH$_2$CO$_2$Na | 1 |
| 62 | —CH$_3$ | —H | —CH(OH)CH$_3$ | Na$^+$ | —CN | 5 |
| 63 | —H | —H | —CH(OH)CH$_3$ | Na$^+$ | —CH$_2$OH | 8 |
| 64 | —H | —H | —CH(OH)CH$_3$ | Na$^+$ | —CH$_2$OH | 5 |
| 65 | —H | —H | —CH(OH)CH$_3$ | Na$^+$ | —CHO | 5 |
| 66 | —H | —H | —CH(OH)CH$_3$ | Na$^+$ | —CHO | 8 |
| 67 | —H | —H | —CH(OH)CH$_3$ | Na$^+$ | —CO$_2$CH$_3$ | 1 |
| 68 | —H | —H | —CH(F)CH$_3$ | Na$^+$ | —CO$_2$Na | 8 |
| 69 | —CH$_3$ | —H | —CH(OH)CH$_3$ | Na$^+$ | —CH$_2$CO$_2$Na | 5 |
| 70 | —H | —H | —CH(OH)CH$_3$ | Na$^+$ | —SCH$_3$ | 5 |
| 71 | —H | —H | —CH(F)CH$_3$ | Na$^+$ | —SOCH$_3$ | 8 |
| 72 | —CH$_3$ | —H | —CH(OH)CH$_3$ | Na$^+$ | —SO$_2$CH$_3$ | 5 |
| 73 | —H | —H | —CH(OH)CH$_3$ | Na$^+$ | —CH=CHCN | 6 |
| 74 | —H | —H | —CH(OH)CH$_3$ | Na$^+$ | —CH=CHCN | 7 |
| 75 | —H | —H | —CH(OH)CH$_3$ | Na$^+$ | —CHO | 1 |
| 76 | —H | —H | —CH(OH)CH$_3$ | Na$^+$ | —CHO | 6 |
| 77 | —H | —H | —CH(OH)CH$_3$ | Na$^+$ | —CN | 1 |
| 78 | —H | —H | —CH(OH)CH$_3$ | Na$^+$ | —CN | 7 |
| 79 | —H | —H | —CH(OH)CH$_3$ | Na$^+$ | —SOCH$_3$ | 1 |
| 80 | —H | —H | —CH(OH)CH$_3$ | Na$^+$ | —SOCH$_3$ | 6 |

TABLE II

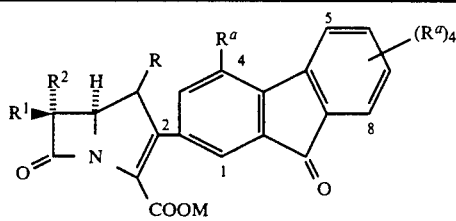

| # | R | R[1] | R[2] | M | R[a] | Ra position |
|---|---|---|---|---|---|---|
| 1 | —H | —H | —CH(OH)CH$_3$ | K$^+$ | —OCH$_3$ | 4 |
| 2 | —H | —H | —CH(OH)CH$_3$ | Na$^+$ | —OCH$_2$CO$_2$Na | 4 |
| 3 | —H | —H | —CH(OH)CH$_3$ | K$^+$ | —OCH$_2$CH$_2$OH | 4 |
| 4 | —H | —H | —CH(OH)CH$_3$ | K$^+$ | —CF$_3$ | 4 |

TABLE II-continued

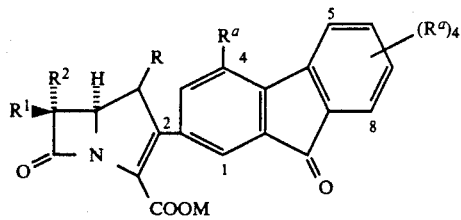

| # | R | R¹ | R² | M | Rᵃ | Ra position |
|---|---|---|---|---|---|---|
| 5 | —H | —H | —CH(OH)CH₃ | Na⁺ | —F | 4 |
| 6 | —H | —H | —CH(OH)CH₃ | Na⁺ | —Cl | 6 |
| 7 | —H | —H | —CH(OH)CH₃ | K⁺ | —Br | 7 |
| 8 | —H | —H | —CH₂OH | K⁺ | —I | 4,6 |
| 9 | —H | —H | —CH(OH)CH₃ | K⁺ | —OH | 4,6,7 |
| 10 | —H | —H | —CH(OH)CH₃ | Na⁺ | —OCOCH₃ | 6 |
| 11 | —H | —H | —CH(OH)CH₃ | Na⁺ | —OCONH₂ | 6 |
| 12 | —H | —H | —CH(OH)CH₃ | K⁺ | —SCH₃ | 6 |
| 13 | —H | —H | —CH(F)CH₃ | K⁺ | —SOCH₃ | 7 |
| 14 | —CH₃ | —H | —CH(OH)CH₃ | Na⁺ | —SO₂CH₃ | 7 |
| 15 | —H | —H | —CH(OH)CH₃ | Na⁺ | —SCH₂CH₂OH | 7 |
| 16 | —H | —H | —CH(OH)CH₃ | Na⁺ | —SOCH₂CH₂OH | 7 |
| 17 | —H | —H | —CH(OH)CH₃ | K⁺ | —SO₂CH₂CH₂OH | 7 |
| 18 | —H | —H | —CH(OH)CH₃ | Na⁺ | —SO₂NH₂ | 4,7 |
| 19 | —H | —H | —CH(OH)CH₃ | K⁺ | —SO₂N(CH₃)₂ | 4,6 |
| 20 | —H | —H | —CF₂CH₃ | K⁺ | —NHCHO | 4,6 |
| 21 | —CH₃ | —H | —CH(OH)CH₃ | K⁺ | —NHCOCH₃ | 4,7 |
| 22 | —H | —H | —CH(OH)CH₃ | K⁺ | —NHCO₂CH₃ | 4,6 |
| 23 | —H | —H | —CH(OH)CH₃ | Na⁺ | —NHSO₂CH₃ | 4,7 |
| 24 | —H | —H | —CH(OH)CH₃ | Na⁺ | —CN | 6 |
| 25 | —H | —H | —CH(OH)CH₃ | K⁺ | —CHO | 7 |
| 26 | —H | —H | —CH(OH)CH₃ | K⁺ | —COCH₃ | 6 |
| 27 | —H | —H | —CH(OH)CH₃ | K⁺ | —COCH₂OH | 7 |
| 28 | —H | —H | —CH(OH)CH₃ | K⁺ | —CH=NOH | 6 |
| 29 | —H | —H | —CH(OH)CH₃ | Na⁺ | —CH=NOCH₃ | 7 |
| 30 | —CH₃ | —H | —CH(OH)CH₃ | K⁺ | —CH=NOCH₂CO₂K | 4 |
| 31 | —H | —H | —CH(OH)CH₃ | Na⁺ | —CH=NOCMe₂CO₂Na | 6 |
| 32 | —H | —H | —CH(OH)CH₃ | Na⁺ | —CH=NOCMe₂CO₂Me | 7 |
| 33 | —H | —H | —CH(OH)CH₃ | K⁺ | —CO₂CH₂CH₂OH | 4 |
| 34 | —H | —H | —CH(OH)CH₃ | Na⁺ | —CONH₂ | 6 |
| 35 | —H | —H | —CH(OH)CH₃ | Na⁺ | —CONHCH₃ | 7 |
| 36 | —H | —H | —CH(OH)CH₃ | Na⁺ | —CON(CH₃)₂ | 6 |
| 37 | —H | —H | —CH(OH)CH₃ | K⁺ | —CONHCH₂CN | 7 |
| 38 | —CH₃ | —H | —CF₂CH₃ | Na⁺ | —CONHCH₂CONH₂ | 4 |
| 39 | —H | —H | —CH(OH)CH₃ | K⁺ | —CONHCH₂CO₂H | 6 |
| 40 | —H | —H | —CH(OH)CH₃ | Na⁺ | —CONHOH | 7 |
| 41 | —H | —H | —CH(OH)CH₃ | Na⁺ | —CONHOCH₃ | 4 |
| 42 | —H | —H | —CH(OH)CH₃ | Na⁺ | —tetrazolyl | 6 |
| 43 | —H | —H | —CH₂OH | Na⁺ | —CO₂Na | 4 |
| 44 | —H | —H | —CH(OH)CH₃ | Na⁺ | —SCF₃ | 6 |
| 45 | —H | —H | —CH(OH)CH₃ | Na⁺ | —PO₃NaH | 7 |
| 46 | —H | —H | —CH(OH)CH₃ | Na⁺ | —CONHSO₂Ph | 4 |
| 47 | —CH₃ | —H | —CH(OH)CH₃ | Na⁺ | —CONHSO₂NH₂ | 6 |
| 48 | —H | —H | —CH(OH)CH₃ | Na⁺ | —SO₃Na | 6 |
| 49 | —H | —H | —CH(OH)CH₃ | Na⁺ | —SO₂NHCN | 7 |
| 50 | —CH₃ | —H | —CH(F)CH₃ | Na⁺ | —SO₂NHCONH₂ | 6 |
| 51 | —H | —H | —CH(OH)CH₃ | K⁺ | —CH=CHCN | 4 |
| 52 | —H | —H | —CH(OH)CH₃ | K⁺ | —CH=CHCONH₂ | 6 |
| 53 | —H | —H | —CH(OH)CH₃ | Na⁺ | —CH=CHCO₂Na | 7 |
| 54 | —H | —H | —CH(OH)CH₃ | Na⁺ | —C≡C—CONH₂ | 4 |
| 55 | —CH₃ | —H | —CH(OH)CH₃ | Na⁺ | —C≡C—CN | 6 |
| 56 | —H | —H | —CH(OH)CH₃ | Na⁺ | —CH₂OH | 4 |
| 57 | —H | —H | —CH(OH)CH₃ | Na⁺ | —CH₂OH | 6 |
| 58 | —H | —H | —CH(OH)CH₃ | Na⁺ | —CH₂OH | 7 |
| 59 | —H | —H | —CH₂CH₃ | K⁺ | —CH₂N₃ | 6 |
| 60 | —H | —H | —CH(OH)CH₃ | Na⁺ | —CH₂CO₂Na | 7 |
| 61 | —H | —H | —CH(OH)CH₃ | Na⁺ | —CH₂CO₂Na | 4 |
| 62 | —CH₃ | —H | —CH(OH)CH₃ | Na⁺ | —CN | 5 |
| 63 | —H | —H | —CH(OH)CH₃ | Na⁺ | —CH₂OH | 8 |
| 64 | —H | —H | —CH(OH)CH₃ | Na⁺ | —CH₂OH | 5 |
| 65 | —H | —H | —CH(OH)CH₃ | Na⁺ | —CHO | 5 |
| 66 | —H | —H | —CH(OH)CH₃ | Na⁺ | —CHO | 8 |
| 67 | —H | —H | —CH(OH)CH₃ | Na⁺ | —CO₂CH₃ | 5 |
| 68 | —H | —H | —CH(F)CH₃ | Na⁺ | —CO₂Na | 8 |
| 69 | —CH₃ | —H | —CH(OH)CH₃ | Na⁺ | —CH₂CO₂Na | 5 |
| 70 | —H | —H | —CH(OH)CH₃ | Na⁺ | —SCH₃ | 5 |
| 71 | —H | —H | —CH(F)CH₃ | Na⁺ | —SOCH₃ | 8 |
| 72 | —CH₃ | —H | —CH(OH)CH₃ | Na⁺ | —SO₂CH₃ | 5 |
| 73 | —H | —H | —CH(OH)CH₃ | Na⁺ | —CH=CHCN | 6 |

TABLE II-continued

| # | R | R¹ | R² | M | Rᵃ | Ra position |
|---|---|----|----|---|-----|-------------|
| 74 | —H | —H | —CH(OH)CH₃ | Na⁺ | —CH=CHCN | 7 |
| 75 | —H | —H | —CH(OH)CH₃ | Na⁺ | —CN | 7. |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form—COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protecting groups include benzhydryl, p-nitrobenzyl, 2-naphthylmethyl, allyl, benzyl, trichloroethyl, silyl such as trimethylsilyl, trimethylsilylethyl, phenacyl, p-methoxybenzyl, acetonyl, o-nitrobenzyl, p-methoxyphenyl, 4-pyridylmethyl, and t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria or medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applictions may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1) define the procedure for determining DHP susceptibility of the present carbapenems and 2) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The invention is further defined by reference to the following examples, which are illustrative and not limiting. All temperatures are in degrees Celsius.

EXAMPLE 1

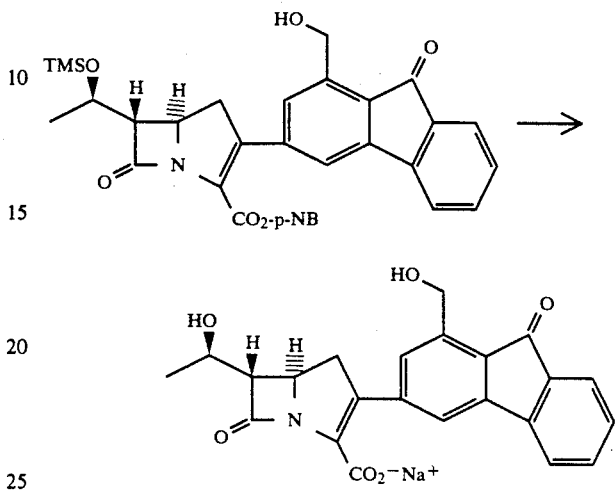

Sodium (5R,6S)-2-(1-hydroxymethyl-9-fluorenon-3-yl)-6-(1R-hydroxyethyl)carbapen-2-em-3-carboxylate p-Nitrobenzyl (5R,6S)-2-(1-hydroxymethyl-9-flourenon-3-yl)-6-(1R-trimethylsilyloxyethyl)carbapen-2-em-3-carboxylate (30 mg) was dissolved in THF (2.6 ml), EtOH (2.6 ml), water (0.5 ml). AcOH (1 μl) was added and the reaction allowed to stir at 35° for 3 hours during which the trimethylsilyl group was hydrolysed off. The reaction mixture was diluted with pH 7 Sodium phosphate buffer (0.5 ml, 0.2M) and 5% Pd/C catalyst 6 mg was added. The mixture was hydrogenated at atmosphereic pressure for 1 hour. The catalyst was filtered off, washed with water and the combined filtrate and washings were extracted once with EtOAc and then evaporated to a small volume. The product was purified by reverse phase HPLC on a Whatman Partisil ODS3 column using a water/CH$_3$CN gradient elution to give the product.

$^1$H-NMR (D$_2$O, 300 MHz): δ1.37 (d, J=7, CH$_3$—C); 3.18 (d of d, J=16, J=10, C-1 Ha); 3.50 (d of d, J=16, J=8, C-1 Hb); 3.63 (d of d, J=6, J=2.5, C-6H); 4.35 (m, CH$_3$—CH—); 4.46 (d of t, J=8.5, J=2.5, C-5H); 4.81 (s, CH$_2$OH); 7.1-7.55 (m, ArH).

UV (H$_2$O, λmax): 256, 306, 370.

EXAMPLE 2

Sodium (5R, 6S)-2-(6-hydroxymethyl-9-fluorenon-3-yl)-6-(1R-hydroxyethyl)carbapen-2-em-3-carboxylate Starting with the product of Example 36, hydrolysis of the trimethylsilyl group followed by reduction of the p-nitrobenzyl group, as described in Example 1, the named product is obtained.

EXAMPLE 3

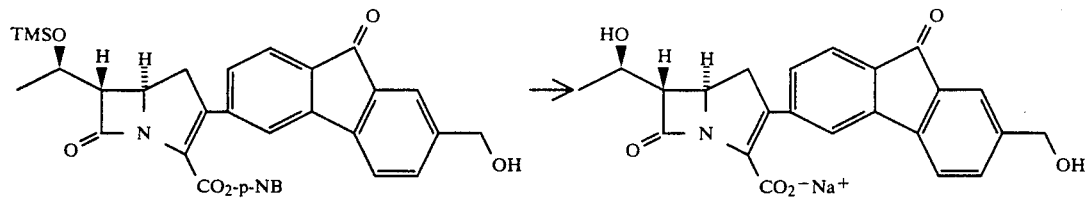

Sodium (5R,6S)-2-(7-hydroxymethyl-9-fluorenon-3-yl)-6-(1R-hydroxyethyl)carbapen-2-em-3-carboxylate Starting with the product of Example 37, hydrolysis of the trimethylsilyl group followed by reduction of the p-nitrobenzyl group, as described in Example 1, the named product was obtained.

$^1$H-NMR (D$_2$O, 300 MHz): δ1.43 (d, J=6, CH$_3$—C); 3.19 (d of d, J=16, J=10, C-1 Ha); 3.52 (d of d, J=16, J=8, C-1 Hb); 3.66 (d of d, J=4.5, J=1.5, C-6H; 4.38 (m, CH$_3$—CH—); 4.46 (d of t, J=9.5, J=1.5, C-5H); 4.62 (s, CH$_2$OH); 7.12–7.45 (m, ArH).

UV (H$_2$O, λmax): 262, 306, 370.

EXAMPLE 4

Sodium (5R,6S)-2-(1-formyl-9-fluorenon-3-yl)-6-(1R-hydroxyethyl)-carbapen-2-em-3-carboxylate Starting with the product of Example 39, hydrolysis of the trimethylsilyl group followed by reduction of the p-nitrobenzyl group, as described in Example 1, the named product is obtained.

EXAMPLE 5

Sodium (5R,6S)-2-(6-formyl-9-fluorenon-3-yl)-6-(1R-hydroxyethyl)-carbapen-2-em-3-carboxylate Starting with the product of Example 40, hydrolysis of the trimethylsilyl group followed by reduction of the p-nitrobenzyl group, as described in Example 1, the named product is obtained.

EXAMPLE 6

EXAMPLE 7

Sodium (5R,6S)-2-(1-methoxyiminomethyl-9-fluorenon-3-yl)-6-(1R-hydroxyethyl)carbapen-2-em-3-carboxylate Starting with the product of Example 42, hydrolysis of the trimethylsilyl group followed by reduction of the p-nitrobenzyl group, as described in Example 1, the named product is obtained.

EXAMPLE 8

Sodium (5R,6S)-2-(6-methoxyiminomethyl-9-fluorenon-3-yl)-6-(1R-hydroxyethyl)carbapen-2-em-3-carboxylate Starting with the product of Example 43, hydrolysis of the trimethylsilyl group followed by reduction of the p-nitrobenzyl group, as described in Example 1, the named product is obtained.

EXAMPLE 9

Sodium (5R,6S)-2-(7-methoxyiminomethyl-9-fluorenon-3-yl)-6-(1R-hydroxyethyl)carbapen-2-em-3-carboxylate Starting with the product of Example 44, hydrolysis of the trimethylsilyl group followed by reduction of the p-nitrobenzyl group, as described in Example 1, the named product is obtained.

EXAMPLE 10

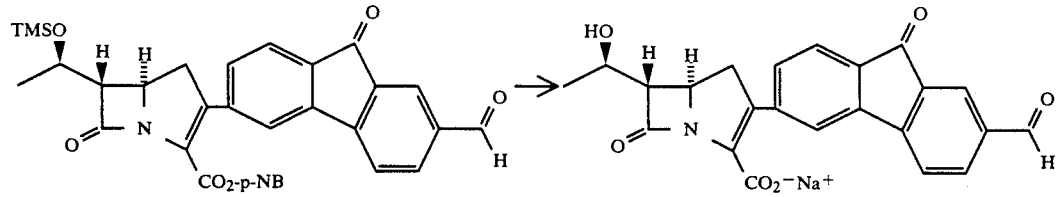

Sodium (5R,6S)-2-(7-formyl-9-fluorenon-3-yl)-6-(1R-hydroxyethyl)carbapen-2-em-3-carboxylate Starting with the product of Example 41, hydrolysis of the trimethylsilyl group followed by reduction of the p-nitrobenzyl group, as described in Example 1, the named product was obtained.

$^1$H-NMR (D$_2$O, 300 MHz): δ1.44 (d, J=7, CH$_3$—C); 3.18 (d of d, J=15.5, J=10, C-1 Ha); 3.49 (d of d, J=15.5, J=9, C-1 Hb); 3.65 (d of d, J=3, J=2.0, C-6H); 4.39 (m, CH$_3$—CH—); 4.48 (d of t, J=10, J=2.5, C-5H); 7.23–7.96 (m, ArH); 9.83 (s, CHO).

UV (H$_2$O, λmax): 275, 325.

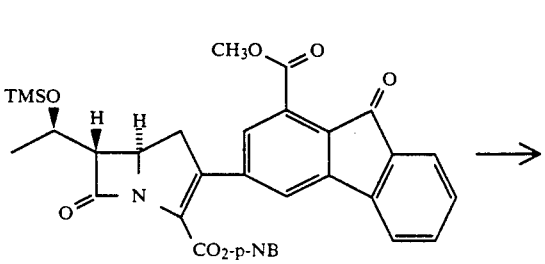

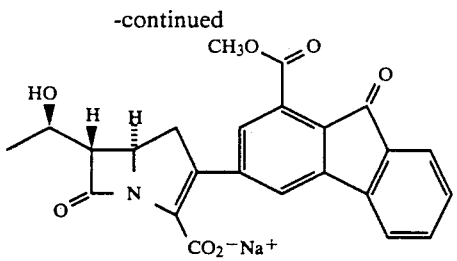

Sodium
(5R,6S)-2-(1-methoxycarbonyl-9-fluorenon-3-yl)-6-(1R-hydroxyethyl)carbapen-2-em-3-carboxylate Starting with the product of Example 45, hydrolysis of the trimethylsilyl group followed by reduction of the p-nitrobenzyl group, as described in Example 1, the named product was obtained.

$^1$H-NMR (D$_2$O, 300 MHz): δ1.44 (d, J=7, CH$_3$—C); 3.17 (d of d, J=17, J=10, C-1 Ha); 3.50 (d of d, J=17, J=8.5, C-1 Hb); 3.63 (d of d, J=1.5, J=4, C-6H); 4.07 (s, OCH$_3$); 4.40 (m, CH$_3$—C$\underline{H}$—); 4.40 (d of t, J=8, J=1.5, C-5H); 7.3–7.8 (m, Ar$\underline{H}$).

UV (H$_2$O, λmax): 257, 307, 355.

EXAMPLE 11

Sodium (5R, 6S)-2-(6-methoxycarbonyl-9-fluorenon-3-yl)-6-(1R-hydroxyethyl)carbapen-2-em-3-carboxylate Starting with the product of Example 46, hydrolysis of the trimethylsilyl group followed by reduction of the p-nitrobenzyl group, as described in Example 1, the named product is obtained.

EXAMPLE 12

Sodium (5R, 6S)-2-(7-methoxycarbonyl-9-fluorenon-3-yl)-6-(1R-hydroxyethyl)carbapen-2-em-3-carboxylate Starting with the product of Example 47, hydrolysis of the trimethylsilyl group followed by reduction of the p-nitrobenzyl group, as described in Example 1, the named product is obtained.

EXAMPLE 13

Disodium (5R, 6S)-2-(1-carboxylate-9-fluorenon-3-yl)-6-(1R-hydroxyethyl)carbapen-2-em-3-carboxylate Starting with the product of Example 48, hydrolysis of the trimethylsilyl group followed by reduction of the p-nitrobenzyl group, as described in Example 1, the named product is obtained.

EXAMPLE 14

Disodium (5R, 6S)-2-(6-carboxylate-9-fluorenon-3-yl)-6-(1R-hydroxyethyl)carbapen-2-em-3-carboxylate Starting with the product of Example 49, hydrolysis of the trimethylsilyl group followed by reduction of the p-nitrobenzyl group, as described in Example 1, the named product is obtained.

EXAMPLE 15

Disodium (5R, 6S)-2-(7-carboxylate-9-fluorenon-3-yl)-6-(1R-hydroxyethyl)carbapen-2-em-3-carboxylate Starting with the product of Example 50, hydrolysis of the trimethylsilyl group followed by reduction of the p-nitrobenzyl group, as described in Example 1, the named product is obtained.

EXAMPLE 16

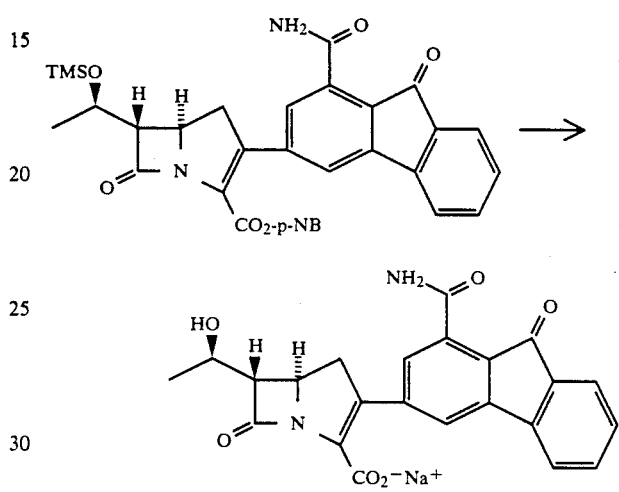

Sodium
(5R,6S)-2-(1-aminocarbonyl-9-fluorenon-3-yl)-6-(1R-hydroxyethyl)carbpen-2-em-3-carboxylate Starting with the product of Example 51, hydrolysis of the trimethylsilyl group followed by reduction of the p-nitrobenzyl group, as described in Example 1, the named product was obtained.

$^1$H-NMR (D$_2$O, 300 MHz): δ1.41 (d, J=7, CH$_3$—C); 3.11 (d of d, J=17, J=10, C-1 Ha); 3.42 (d of d, J=17, J=8.0, C-1 Hb); 3.63 (d of d, J=2.5, J=5, C-6H); 4.36 (m, CH$_3$—C$\underline{H}$—); 4.44 (d of t, J=10, J=2.5, C-5H); 7.15–7.5 (m, Ar$\underline{H}$).

UV (H$_2$O, λmax): 257, 307, 370.

EXAMPLE 17

Sodium (5R, 6S)-2-(6-aminocarbonyl-9-fluorenon-3-yl)-6-(1R-hydroxyethyl)carbapen-2-em-3-carboxylate Starting with the product of Example 52, hydrolysis of the trimethylsilyl group followed by reduction of the p-nitrobenzyl group, as described in Example 1, the named product is obtained.

EXAMPLE 18

Sodium (5R, 6S)-2-(7-aminocarbonyl-9-fluorenon-3-yl)-6-(1R-hydroxyethyl)carbapen-2-em-3-carboxylate Starting with the product of Example 53, hydrolysis of the trimethylsilyl group followed by reduction of the p-nitrobenzyl group, as described in Example 1, the named product is obtained.

EXAMPLE 19

Sodium (5R, 6S)-2-(1-N-methylaminocarbonyl-9-fluorenon-3-yl)-6-(1R-hydroxyethyl)carbapen-2-em-3-carboxylate Starting with the product of Example 54, hydrolysis of the trimethylsilyl group followed by reduction of the p-nitrobenzyl group, as described in Example 1, the named product is obtained.

EXAMPLE 20

Sodium (5R, 6S)-2-(6-N-methylaminocarbonyl-9-fluorenon-3-yl)-6-(1R-hydroxyethyl)carbapen-2-em-3-carboxylate Starting with the product of Example 55, hydrolysis of the trimethylsilyl group followed by reduction of the p-nitrobenzyl group, as described in Example 1, the named product is obtained.

EXAMPLE 21

Sodium (5R, 6S)-2-(7-N-methylaminocarbonyl-9-fluorenon-3-yl)-6-(1R-hydroxyethyl)carbapen-2-em-3-carboxylate Starting with the product of Example 56, hydrolysis of the trimethylsilyl group followed by reduction of the p-nitrobenzyl group, as described in Example 1, the named product is obtained.

EXAMPLE 22

Sodium (5R, 6S)-2-(1-N,N-dimethylaminocarbonyl-9-fluorenon-3-yl)-6-(1R-hydroxyethyl)carbapen-2-em-3-carboxylate Starting with the product of Example 57, hydrolysis of the trimethylsilyl group followed by reduction of the p-nitrobenzyl group, as described in Example 1, the named product is obtained.

EXAMPLE 23

Sodium (5R, 6S)-2-(6-N,N-dimethylaminocarbonyl-9-fluorenon-3-yl)-6-(1R-hydroxyethyl)carbapen-2-em-3-carboxylate Starting with the product of Example 58, hydrolysis of the trimethylsilyl group followed by reduction of the p-nitrobenzyl group, as described in Example 1, the named product is obtained.

EXAMPLE 24

Sodium (5R, 6S)-2-(7-N,N-dimethylaminocarbonyl-9-fluorenon-3-yl)-6-(1R-hydroxyethyl)carbapen-2-em-3-carboxylate Starting with the product of Example 59, hydrolysis of the trimethylsilyl group followed by reduction of the p-nitrobenzyl group, as described in Example 1, the named product is obtained.

EXAMPLE 25

Sodium (5R, 6S)-2-(1-methylthio-9-fluorenon-3-yl)-6-(1R-hydroxyethyl)carbapen-2-em-3-carboxylate Starting with the product of Example 60, hydrolysis of the trimethylsilyl group followed by reduction of the p-nitrobenzyl group, as described in Example 1, the named product is obtained.

EXAMPLE 26

Sodium (5R, 6S)-2-(6-methylthio-9-fluorenon-3-yl)-6-(1R-hydroxyethyl)carbapen-2-em-3-carboxylate Starting with the product of Example 61, hydrolysis of the trimethylsilyl group followed by reduction of the p-nitrobenzyl group, as described in Example 1, the named product is obtained.

EXAMPLE 27

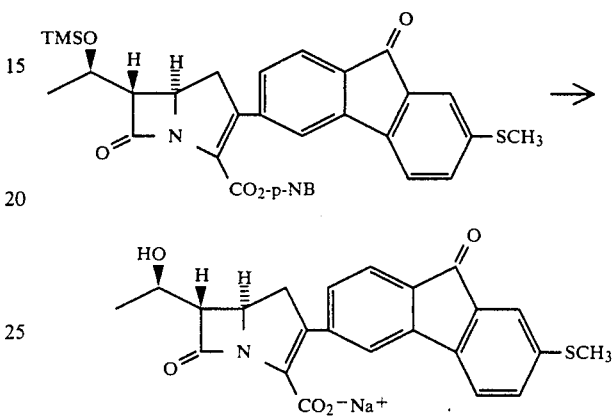

Sodium (5R,6S) 2-(7-methylthio-9-fluorenon-3-yl)-6-(1R-hydroxyethyl)-carbapen-2-em-3-carboxylate Starting with the product of Example 62, hydrolysis of the trimethylsilyl group followed by reduction of the p-nitrobenzyl group, as described in Example 1, the named product was obtained.

$^1$H-NMR ($D_2O$, 300 MHz): δ1.40 (d, J=7, $CH_3$—C); 2.54 (s, $SCH_3$); 3.16 (m, C-1 Ha); 3.47 (m, C-1 Hb); 3.63 (m, C-6H); 4.40 (m, $CH_3$—CH—); 4.40 (d of t, J=7.5, J=2.5, C-5H); 7.01–7.24 (m, $\overline{Ar}$H).

UV ($H_2O$, λmax): 276, 317.

EXAMPLE 28

Sodium (5R, 6S)-2-(1-methylsulfinyl-9-fluorenon-3-yl)-6-(1R-hydroxyethyl)carbapen-2-em-3-carboxylate Starting with the product of Example 63, hydrolysis of the trimethylsilyl group followed by reduction of the p-nitrobenzyl group, as described in Example 1, the named product is obtained.

EXAMPLE 29

Sodium (5R, 6S)-2-(6-methylsulfinyl-9-fluorenon-3-yl)-6-(1R-hydroxyethyl)carbapen-2-em-3-carboxylate Starting with the product of Example 64, hydrolysis of the trimethylsilyl group followed by reduction of the p-nitrobenzyl group, as described in Example 1, the named product is obtained.

EXAMPLE 30

Sodium (5R, 6S)-2-(7-methylsulfinyl-9-fluorenon-3-yl)-6-(1R-hydroxyethyl)carbapen-2-em-3-carboxylate Starting with the product of Example 65, hydrolysis of the trimethylsilyl group followed by reduction of the p-nitrobenzyl group, as described in Example 1, the named product is obtained.

EXAMPLE 31

Sodium (5R, 6S)-2-(1-methylsulfonyl-9-fluorenon-3-yl)-6-(1R-hydroxyethyl)carbapen-2-em-3-carboxylate Starting with the product of Example 66, hydrolysis of the trimethylsilyl group followed by reduction of the p-nitrobenzyl group, as described in Example 1, the named product is obtained.

EXAMPLE 32

Sodium (5R, 6S)-2-(6-methylsulfonyl-9-fluorenon-3-yl)-6-(1R-hydroxyethyl)carbapen-2-em-3-carboxylate Starting with the product of Example 67, hydrolysis of the trimethylsilyl group followed by reduction of the p-nitrobenzyl group, as described in Example 1, the named product is obtained.

EXAMPLE 33

Sodium (5R, 6S)-2-(7-methylsulfonyl-9-fluorenon-3-yl)-6-(1R-hydroxyethyl)carbapen-2-em-3-carboxylate Starting with the product of Example 68, hydrolysis of the trimethylsilyl group followed by reduction of the p-nitrobenzyl group, as described in Example 1, the named product is obtained.

EXAMPLE 34

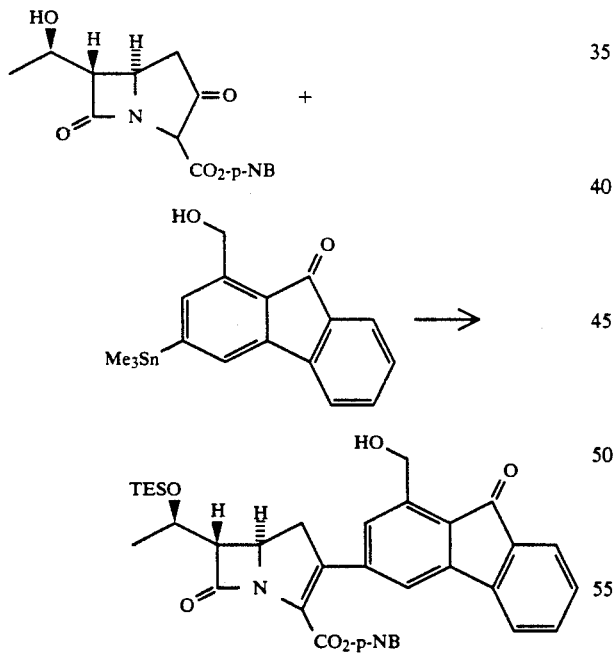

p-Nitrobenzyl (5R,6S)-2-(1-hydroxymethyl-9-fluorenon-3-yl)-6-(1R-triethylsilyloxyethyl)carbapen-2-em-3-carboxylate p-Nitrobenzyl (5R,6S)-2-oxo-6-(1R-hydroxyethyl)-carbapenam-3-carboxylate (143 mg, 0.41 mmoles) was dissolved in 2 ml THF and cooled to $-78°$ under $N_2$, diisopropylamine (63 μl, 1.1 eq) was added followed 10 minutes later by trifluoromethanesulfonic anhydride (75 μl, 1.1 eq). The reaction mixture was allowed to stir at $-78°$ for 15 min. Triethylamine (62 μl, 1.1 eq) was then added followed by triethylsilyl trifluoromethane sulfonate (108 μl, 1.1 eq). The reaction mixture was allowed to stir at $-78°$ for 20 min. $Pd_2(DBA)_3 \cdot CHCl_3$ (8.5 mg, 0.02 eq) and tris(2,4,6-trimethoxyphenyl)phosphine (17.4 mg, 0.08 eq) were added followed by 3-trimethylstannyl-1-hydroxymethyl-9-fluorenone, Example 69, (100 mg, 0.27 mmoles) in THF (1 ml). N-methylpyrrolidone (3 ml) was added followed by $ZnCl_2$ (0.45 ml, 1M soln in $Et_2O$). The cooling bath was removed and the reaction mixture was brought rapidly to room temperature and allowed to stir 0.5 hr. The reaction mixture was diluted with $Et_2O/EtOAc$ 4:1, 25 ml and washed with pH 7 phosphate buffer (0.2M), then with water and brine then dried over $Na_2SO_4$ and evaporated to give a residue which was purified by preparative tlc (30% EtOAc/hexane elution) to give the product (128 mg, 73%).

$^1$H-NMR ($CDCl_3$, 200 MHz): δ0.62 (q, J=7, $CH_3-\underline{CH}_2-Si$); 0.96 (t, J=7, $\underline{CH}_3-CH_2-Si$); 1.32 (d, J=7, $CH_3-C$); 3.32 (m, C-6 H and C-1 H); 4.32 (m, C-5H and $CH_3-\underline{CH}-$); 4.86 (s, $CH_2OH$); 5.21, 5.37 (2d, J=12, $ArCH_2O$); 7.13–8.2 (m, ArH).

EXAMPLE 35

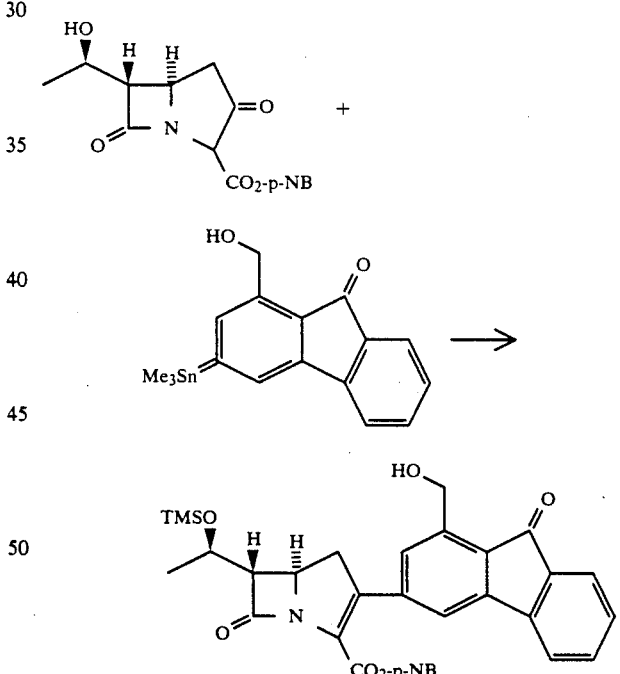

p-Nitrobenzyl (5R,6S)-2-(1-hydroxymethyl-9-fluorenon-3-yl)-6-(1R-trimethylsilyloxyethyl)carbapen-2-em-3-carboxylate Using 1.1 eq of trimethylsilyl trifluoromethanesulfonate in place of triethylsilyl trifluoromethanesulfonate in the process of Example 34 gave the desired product.

$^1$H-NMR ($CDCl_3$, 200 MHz): δ0.096 (s, $CH_3-Si$); 1.32 (d, J=7, $CH_3-C$); 3.32 (m, C-6 H and C-1 H); 4.32 (m, C-5 H and $CH_3-\underline{CH}-$); 4.86 (s, $CH_2OH$); 5.21, 5.37 (2d, J-12, $ArCH_2O$); 7.13–8.2 (m, ArH).

EXAMPLE 36

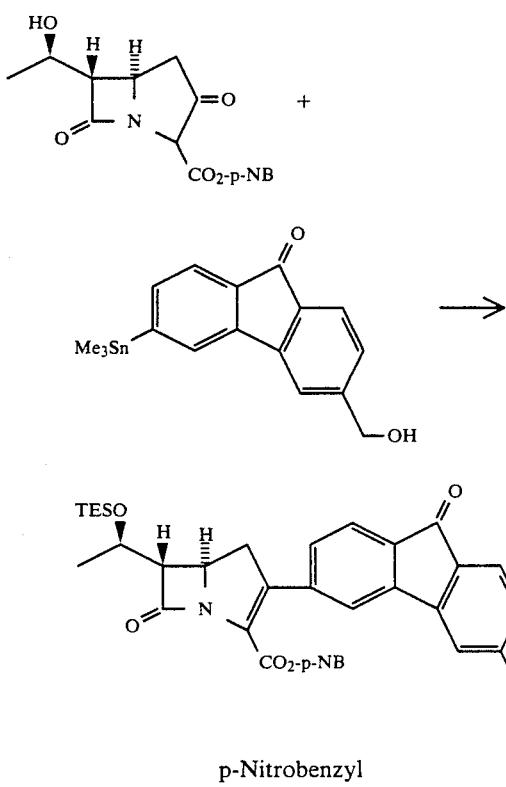

p-Nitrobenzyl
(5R,6S)-2-(6-hydroxymethyl-9-fluorenon-3-yl)-6-(1R-triethylsilyloxyethyl)carbapen-2-em-3-carboxylate Using 3-trimethylstannyl-6-hydroxymethyl-9-fluorenone, Example 70, under the conditions of Example 34, there is obtained the corresponding 6-substituted fluorenone carbapenem.

EXAMPLE 37

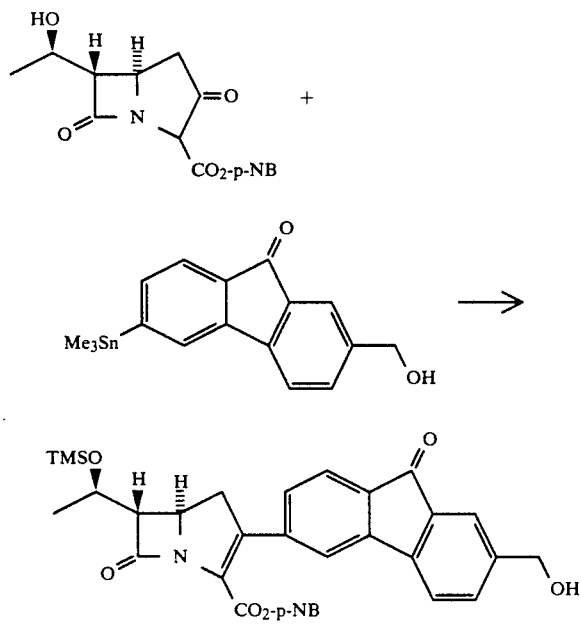

p-Nitrobenzyl
(5R,6S)-2-(7-hydroxymethyl-9-fluorenon-3-yl)-6-(1R-trimethylsilyloxyethyl)-carbapen-2-em-3-carboxylate Using stannane from Example 71 in place of 3-trimethylstannyl-1-hydroxymethyl-9-fluorenone, under the conditions of Example 35, there was obtained the corresponding 7-substituted fluorenone carbapenem.

$^1$H-NMR (CDCl$_3$, 200 MHz): δ0.16 (s, CH$_3$—Si); 1.33 (d, J=7, CH$_3$—C); 3.30 (m, C-6 H and C-1 H); 4.31 (m, C-5 H and CH$_3$—C$\underline{H}$—); 4.74 (s, CH$_2$OH); 5.27 (ABq, J=14, ArCH$_2$O); 7.18–8.04 (m, ArH).

EXAMPLE 38

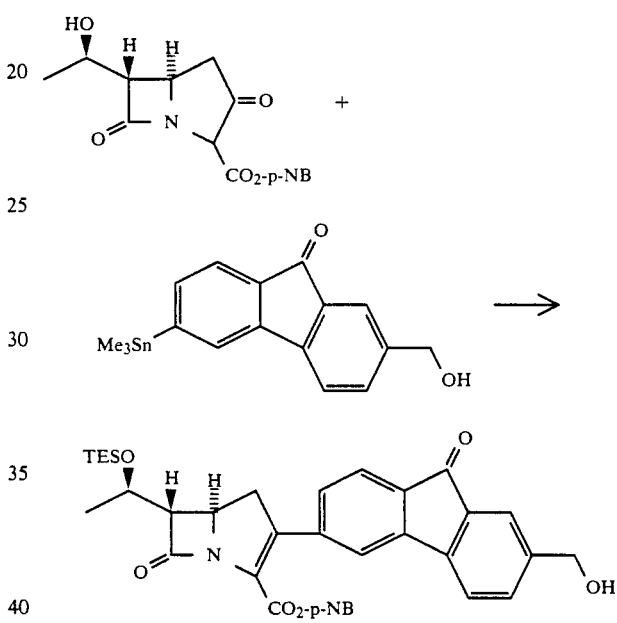

p-Nitrobenzyl
(5R,6S)-2-(7-hydroxymethyl-9-fluorenon-3-yl)-6-(1R-triethylsilyloxyethyl)carbapen-2-em-3-carboxylate Using stannane from Example 71 in place of 3-trimethylstannyl-1-hydroxymethyl-9-fluorenone, under the conditions of Example 34, there was obtained the corresponding 7-substituted fluorenone carbapenem.

$^1$H-NMR (CDCl$_3$, 200 MHz): δ0.63 (q, J=7, CH$_3$—C$\underline{H}_2$—Si); 0.96 (t, J=7, C$\underline{H}_3$—CH$_2$—Si); 1.30 (d, J=7 CH$_3$—C); 3.32 (m, C-6 H and C-1 H); 4.31 (m, C-5 H and CH$_3$—C$\underline{H}$—); 4.72 (s, CH$_2$OH); 5.25 (ABq, J=12, ArCH$_2$O); 7.18–8.04 (m, ArH).

IR (CH$_2$Cl$_2$, cm$^{-1}$): 1778, 1715.

EXAMPLE 39 p-Nitrobenzyl
(5R,6S)-2-(1-formyl-9-fluorenon-3-yl)-6-(1R-trimethylsilyloxyethyl)carbapen-2-em-3-carboxylate Using stannane from Example 72 in place of 3-trimethylstannyl-1-hydroxymethyl-9-fluorenone, under the conditions of Example 35, there is obtained the corresponding 1-substituted fluorenone carbapenem.

EXAMPLE 40 p-Nitrobenzyl
(5R,6S)-2-(6-formyl-9-fluorenon-3-yl)-6-(1R-trimethyl-
silyloxyethyl)carbapen-2-em-3-carboxylate Using stannane from Example 73 in place of 3-trimethylstannyl-1-hydroxymethyl-9-fluorenone, under the conditions of Example 35, there is obtained the corresponding 6-substituted fluorenone carbapenem.

EXAMPLE 41

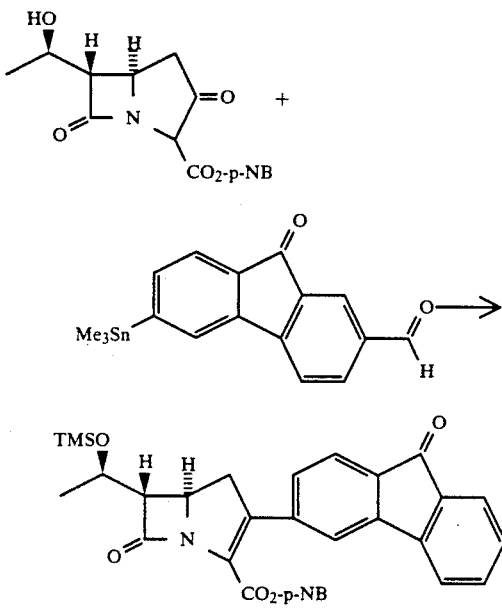

p-Nitrobenzyl
(5R,6S)-2-(7-formyl-9-fluorenon-3-yl)-6-(1R-trimethyl-
silyloxyethyl)carbapen-2-em-3-carboxylate Using stannane from Example 74 in place of 3-trimethylstannyl-1-hydroxymethyl-9-fluorenone, under the conditions of Example 35, there was obtained the corresponding 7-substituted fluorenone carbapenem.

$^1$H-NMR (CDCl$_3$, 200 MHz): δ0.14 (s, CH$_3$—Si); 1.31 (d, J=7, CH$_3$—C); 3.32 (m, C-6 H and C-1 H); 4.30 (m, C-5 H and CH$_3$—C$\underline{\text{H}}$—); 5.30 (ABq, J=12, ArC-H$_2$O); 7.30–8.14 (m, Ar$\underline{\text{H}}$); 10.05 (s, CHO).

EXAMPLE 42 p-Nitrobenzyl
(5R,6S)-2-(1-methoxyiminomethyl-9-fluorenon-3-yl)-6-(1R-trimethylsilyloxyethyl)carbapen-2-em-3-carboxylate Using stannane from Example 75 in place of 3-trimethylstannyl-1-hydroxymethyl-9-fluorenone, under the conditions of Example 35, there is obtained the corresponding 1-substituted fluorenone carbapenem.

EXAMPLE 43 p-Nitrobenzyl
(5R,6S)-2-(6-methoxyiminomethyl-9-fluorenon-3-yl)-6-(1R-trimethylsilyloxyethyl)carbapen-2-em-3-carboxylate Using stannane from Example 76 in place of 3-trimethylstannyl-1-hydroxymethyl-9-fluorenone, under the conditions of Example 35, there is obtained the corresponding 6-substituted fluorenone carbapenem.

EXAMPLE 44 p-Nitrobenzyl
(5R,6S)-2-(7-methoxyiminomethyl-9-fluorenon-3-yl)-6-(1R-trimethylsilyloxyethyl)carbapen-2-em-3-carboxylate Using stannane from Example 77 in place of 3-trimethylstannyl-1-hydroxymethyl-9-fluorenone, under the conditions of Example 35, there is obtained the corresponding 7-substituted fluorenone carbapenem.

EXAMPLE 45

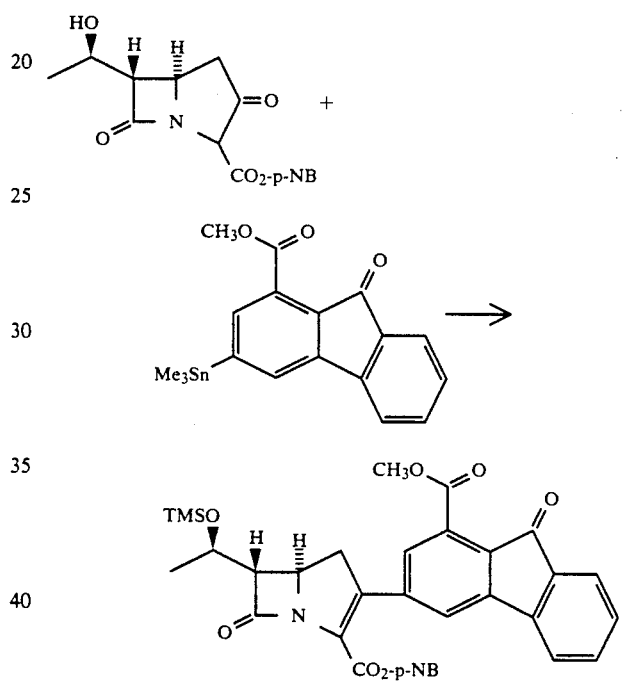

p-Nitrobenzyl
(5R,6S)-2-(1-methoxycarbonyl-9-fluorenon-3-yl)-6-(1R-trimethylsilyloxyethyl)carbapen-2-em-3-carboxylate.

Using stannane from Example 78 in place of 3-trimethylstannyl-1-hydroxymethyl-9-fluorenone, under the conditions of Example 35, there was obtained the corresponding 1-substituted fluoreneone carbapenem.

$^1$H-NMR (CDCl$_3$, 200 MHz): δ0.15 (s, CH$_3$—Si); 1.31 (d, J=7, CH$_3$—C); 3.30 (m, C-6 H and C-1 H and C-1 H); 4.0 (s, OCH$_3$); 4.31 (m, C-5 H and CH$_3$—CH—); 5.21, 5.38 (2d, J=12, ArCH$_2$O); 7.18–8.2 (m, Ar$\underline{\text{H}}$).

EXAMPLE 46 p-Nitrobenzyl
(5R,6S)-2-(6-methoxycarbonyl-9-fluorenon-3-yl)-6-(1R-trimethylsilyloxyethyl)carbapen-2-em-3-carboxylate Using stannane from Example 79 in place of 3-trimethylstannyl-1-hydroxymethyl-9-fluorenone, under the conditions of Example 35, there is obtained the corresponding 6-substituted fluorenone carbapenem.

EXAMPLE 47 p-Nitrobenzyl (5R,6S)-2-(7-methoxycarbonyl-9-fluorenon-3-yl)-6-(1R-trimethylsilyloxyethyl)carbapen-2-em-3-carboxylate Using stannane from Example 80 in place of 3-trimethylstannyl-1-hydroxymethyl-9-fluorenone, under the conditions of Example 35, there is obtained the corresponding 7-substituted fluorenone carbapenem.

EXAMPLE 48 p-Nitrobenzyl (5R,6S)-2-(1-p-nitrobenzyloxycarbonyl-9-fluorenon-3-yl)-6-(1R-trimethylsilyloxyethyl)carbapen-2-em-3-carboxylate Using stannane from Example 81 in place of 3-trimethylstannyl-1-hydroxymethyl-9-fluorenone, under the conditions of Example 35, there is obtained the corresponding 1-substituted fluorenone carbapenem.

EXAMPLE 49 p-Nitrobenzyl (5R,6S)-2-(6-p-nitrobenzyloxycarbonyl-9-fluorenon-3-yl)-6-(1R-trimethylsilyloxyethyl)carbapen-2-em-3-carboxylate Using stannane from Example 82 in place of 3-trimethylstannyl-1-hydroxymethyl-9-fluorenone, under the conditions of Example 35, there is obtained the corresponding 6-substituted fluorenone carbapenem.

EXAMPLE 50 p-Nitrobenzyl (5R,6S)-2-(7-p-nitrobenzyloxycarbonyl-9-fluorenon-3-yl)-6-(1R-trimethylsilyloxyethyl)carbapen-2-em-3-carboxylate Using stannane from Example 83 in place of 3-trimethylstannyl-1-hydroxymethyl-9-fluorenone, under the conditions of Example 35, there is obtained the corresponding 7-substituted fluorenone carbapenem.

EXAMPLE 51

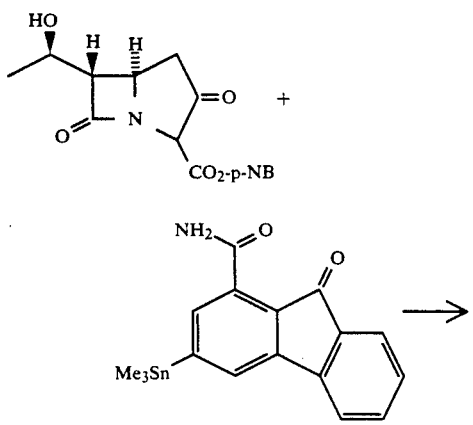

-continued

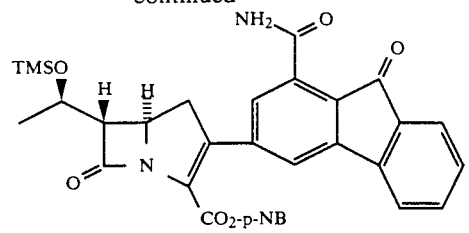

p-Nitrobenzyl (5R,6S)-2-(1-aminocarbonyl-9-fluorenon-3-yl)-6-(1R-trimethylsilyloxyethyl)carbapen-2-em-3-carboxylate Using stannane from Example 84 in place of 3-trimethylstannyl-1-hydroxymethyl-9-fluorenone, under the conditions of Example 35, there is obtained the corresponding 1-substituted fluorenone carbapenem.

EXAMPLE 52 p-Nitrobenzyl (5R,6S)-2-(6-aminocarbonyl-9-fluorenon-3-yl)-6-(1R-trimethylsilyloxyethyl)carbapen-2-em-3-carboxylate Using stannane from Example 85 in place of 3-trimethylstannyl-1-hydroxymethyl-9-fluorenone, under the conditions of Example 35, there is obtained the corresponding 6-substituted fluorenone carbapenem.

EXAMPLE 53 p-Nitrobenzyl (5R,6S)-2-(7-aminocarbonyl-9-fluorenon-3-yl)-6-(1R-trimethylsilyloxyethyl)carbapen-2-em-3-carboxylate Using stannane from Example 86 in place of 3-trimethylstannyl-1-hydroxymethyl-9-fluorenone, under the conditions of Example 35, there is obtained the corresponding 7-substituted fluorenone carbapenem.

EXAMPLE 54 p-Nitrobenzyl (5R,6S)-2-(1-N-methylaminocarbonyl-9-fluorenon-3-yl)-6-(1R-trimethylsilyloxyethyl)carbapen-2-em-3-carboxylate Using stannane from Example 87 in place of 3-trimethylstannyl-1-hydroxymethyl-9-fluorenone, under the conditions of Example 35, there is obtained the corresponding 1-substituted fluorenone carbapenem.

EXAMPLE 55 p-Nitrobenzyl (5R,6S)-2-(6-N-methylaminocarbonyl-9-fluorenon-3-yl)-6-(1R-trimethylsilyloxyethyl)carbapen-2-em-3-carboxylate Using stannane from Example 88 in place of 3-trimethylstannyl-1-hydroxymethyl-9-fluorenone, under the conditions of Example 35, there is obtained the corresponding 6-substituted fluorenone carbapenem.

EXAMPLE 56 p-Nitrobenzyl (5R,6S)-2-(7-N-methylaminocarbonyl-9-fluorenon-3-yl)-6-(1R-trimethylsilyloxyethyl)carbapen-2-em-3-carboxylate Using stannane from Example 89 in place of 3-trimethylstannyl-1-hydroxymethyl-9-fluorenone, under the conditions of Example 35, there is obtained the corresponding 7-substituted fluorenone carbapenem.

EXAMPLE 57 p-Nitrobenzyl
(5R,6S)-2-(1-N,N-dimethylaminocarbonyl-9-fluorenon-3-yl)-6-(1R-trimethylsilyloxyethyl) carbapen-2-em-3-carboxylate Using stannane from Example 90 in place of 3-trimethylstannyl-1-hydroxymethyl-9-fluorenone, under the conditions of Example 35, there is obtained the corresponding 1-substituted fluorenone carbapenem.

EXAMPLE 58 p-Nitrobenzyl
(5R,6S)-2-(6-N,N-dimethylaminocarbonyl-9-fluorenon-3-yl)-6-(1R-trimethylsilyloxyethyl)carbapen-2-em-3-carboxylate Using stannane from Example 91 in place of 3-trimethylstannyl-1-hydroxymethyl-9-fluorenone, under the conditions of Example 35, there is obtained the corresponding 6-substituted fluorenone carbapenem.

EXAMPLE 59 p-Nitrobenzyl
(5R,6S)-2-(7-N,N-dimethylaminocarbonyl-9-fluorenon-3-yl)-6-(1R-trimethylsilyloxyethyl)carbapen-2-em-3-carboxylate Using stannane from Example 92 in place of 3-trimethylstannyl-1-hydroxymethyl-9-fluorenone, under the conditions of Example 35, there is obtained the corresponding 7-substituted fluorenone carbapenem.

EXAMPLE 60 p-Nitrobenzyl
(5R,6S)-2-(1-methylthio-9-fluorenon-3-yl)-6-(1R-trimethylsilyloxyethyl)carbapen-2-em-3-carboxylate Using stannane from Example 93 in place of 3-trimethylstannyl-1-hydroxymethyl-9-fluorenone, under the conditions of Example 35, there is obtained the corresponding 1-substituted fluorenone carbapenem.

EXAMPLE 61 p-Nitrobenzyl
(5R,6S)-2-(6-methylthio-9-fluorenon-3-yl)-6-(1R-trimethylsilyloxyethyl)carbapen-2-em-3-carboxylate Using stannane from Example 94 in place of 3-trimethylstannyl-1-hydroxymethyl-9-fluorenone, under the conditions of Example 35, there is obtained the corresponding 6-substituted fluorenone carbapenem.

EXAMPLE 62

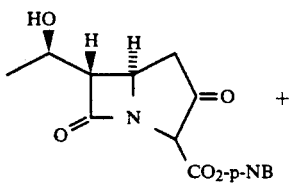

+

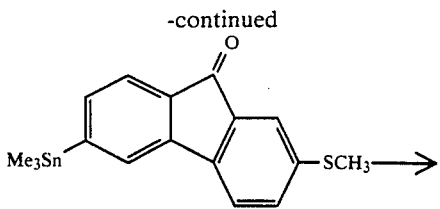

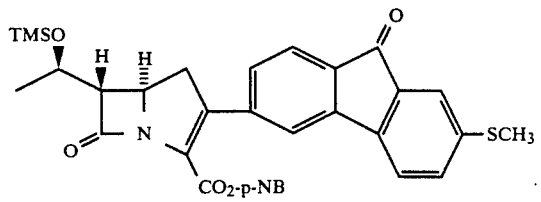

p-Nitrobenzyl
(5R,6S)-2-(7-methylthio-9-fluorenon-3-yl)-6-(1R-trimethylsilyloxyethyl)carbapen-2-em-3-carboxylate Using stannane from Example 95 in place of 3-trimethylstannyl-1-hydroxymethyl-9-fluorenone, under the conditions of Example 35, there was obtained the corresponding 7-substituted fluorenone carbapenem.

$^1$H-NMR (CDCl$_3$, 200 MHz): δ0.18 (s, CH$_3$—Si); 1.33 (d, J=7, CH$_3$—C); 2.56 (s, SCH$_3$); 3.30 (m, C-6 H and C-1 H); 4.31 (m, C-5 H and CH$_3$—CH—); 5.30 (ABq, J=12, ArCH$_2$O); 7.18–8.2 (m, ArH).

IR (CH$_2$Cl$_2$, cm$^{-1}$): 1775, 1715.

EXAMPLE 63 p-Nitrobenzyl
(5R,6S)-2-(1-methylsulfinyl-9-fluoren-3-yl)-6-(1R-hydroxyethyl)carbapen-2-em-3-carboxylate Using stannane from Example 96 in place of 3-trimethylstannyl-1-hydroxymethyl-9-fluorenone, under the conditions of Example 35, there is obtained the corresponding 1-substituted fluorenone carbapenem.

EXAMPLE 64 p-Nitrobenzyl
(5R,6S)-2-(6-methylsulfinyl-9-fluoren-3-yl)-6-(1R-hydroxyethyl)carbapen-2-em-3-carboxylate Using stannane from Example 97 in place of 3-trimethylstannyl-1-hydroxymethyl-9-fluorenone, under the conditions of Example 35, there is obtained the corresponding 6-substituted fluorenone carbapenem.

EXAMPLE 65 p-Nitrobenzyl
(5R,6S)-2-(7-methylsulfinyl-9-fluoren-3-yl)-6-(1R-hydroxyethyl)carbapen-2-em-3-carboxylate Using stannane from Example 95 in place of 3-trimethylstannyl-1-hydroxymethyl-9-fluorenone, under the conditions of Example 35, there is obtained the corresponding 7-substituted fluorenone carbapenem.

EXAMPLE 66 p-Nitrobenzyl
(5R,6S)-2-(1-methylsulfonyl-9-fluoren-3-yl)-6-(1R-hydroxyethyl)carbapen-2-em-3-carboxylate Using stannane from Example 99 in place of 3-trimethylstannyl-1-hydroxymethyl-9-fluorenone, under the conditions of Example 35, there is obtained the corresponding 1-substituted fluorenone carbapenem.

EXAMPLE 67 p-Nitrobenzyl (5R,6S)-2-(6-methylsulfonyl-9-fluoren-3-yl)-6-(1R-hydroxyethyl)carbapen-2-em-3-carboxylate Using stannane from Example 100 in place of 3-trimethylstannyl-1-hydroxymethyl-9-fluorenone, under the conditions of Example 35, there is obtained the corresponding 6-substituted fluorenone carbapenem.

EXAMPLE 68 p-Nitrobenzyl (5R,6S)-2-(7-methylsulfonyl-9-fluoren-3-yl)-6-(1R-hydroxyethyl)carbapen-2-em-3-carboxylate Using stannane from Example 101 in place of 3-trimethylstannyl-1-hydroxymethyl-9-fluorenone, under the conditions of Example 35, there is obtained the corresponding 7-substituted fluorenone carbapenem.

EXAMPLE 69

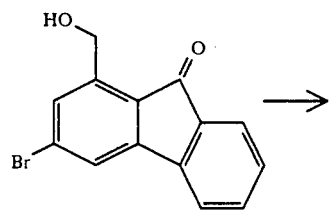

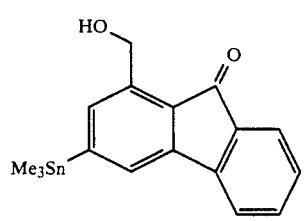

3-Trimethylstannyl-1-hydroxymethyl-9-fluorenone

3-Bromo-1-hydroxymethyl-9-fluorenone (0.289 g) was dissolved in toluene (4 ml) and triphenylphosphine (3.8 mg, 0.02 eq) and tetrakis(triphenylphosphine)palladium (50 mg, 0.06 eq) were added. The solution was degassed under $N_2$ and then treated with hexamethyldistannane (0.208 ml, 1.4 eq). The reaction mixture was heated at 110° under $N_2$ for 1 hour. The reaction mixture was evaporated and the residue purified by preparative tlc to give the product (0.230 g).

$^1$H-NMR (CDCl$_3$, 200 MHz): δ0.35 (s, Me$_3$Sn); 4.32 (t, J=8, OH); 4.85 (d, J=8, Ar-CH$_2$OH); 7.2–7.7 (m, Ar-H).

EXAMPLE 70

3-Trimethylstannyl-6-hydroxymethyl-9-fluorenone

Treatment of the corresponding bromide under the conditions of Example 69, there is obtained the corresponding stannyl fluorenone derivative.

EXAMPLE 71

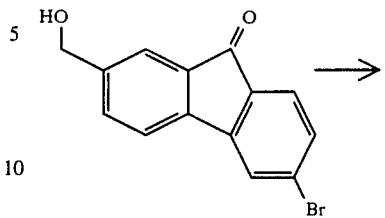

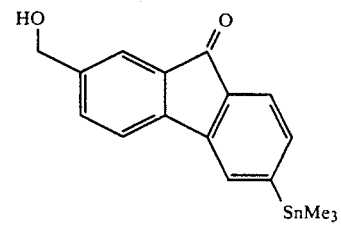

3-trimethylstannyl-7-hydroxymethyl-9-fluorenone

3-Bromo-7-hydroxymethyl-9-fluorenone (200 mg) was dissolved in toluene (10 ml). Reaction mixture was then degassed by bubbling in nitrogen for five minutes. To this solution at 110° C. was added hexamethylditin (282 μl) and then tetrakis(triphenylphosphine)palladium(0) (47 mg) and triphenylphosphine (3.6 mg) in toluene (10 ml) dropwise over a five minute period. Reaction mixture was stirred at 110° C. for five minutes. Toluene was removed under reduced pressure. The residue was purified by preparative tlc using 20% ethyl acetate/methylene chloride gave the desired product (205 mg).

$^1$H-NMR (CDCl$_3$, 200 MHz): δ0.36 (s, SnMe$_3$); 1.8 (t, J=6, OH): 4.73 (d, J=6, CH$_2$OH): 7.42–7.65 (m, ArH).
IR (CH$_2$Cl$_2$, cm$^{-1}$): 1713.

EXAMPLE 72

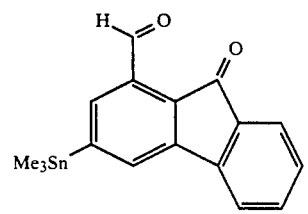

3-Trimethylstannyl-9-fluorenone-1-carboxaldehyde

3-Bromo-9-fluorenone-1-carboxaldehyde (100 mg) is treated under the conditions of Example 69 to give the product.

EXAMPLE 73

3-Trimethylstannyl-9-fluorenone-6-carboxaldehyde

3-Bromo-9-fluorenone-1-carboxaldehyde (100 mg) is treated under the conditions of Example 69 to give the product.

EXAMPLE 74

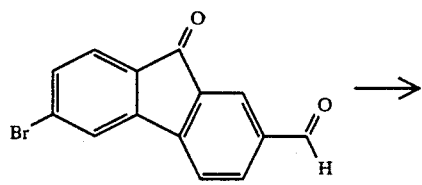

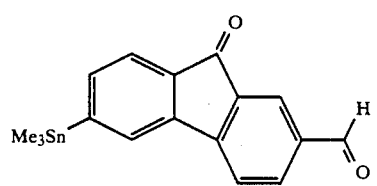

3-Trimethylstannyl-9-fluorenone-7-carboxaldehyde

Treatment of the corresponding 3-bromo derivative described in Example 103 under the conditions described for 3-trimethylstannyl-1-hydroxymethyl-9-fluorenone, Example 69, the desired product was obtained.

$^1$H-NMR (CDCl$_3$, 200 MHz): δ0.38 (s, Me$_3$Sn); 7.5–7.8 (m, Ar-H); 10.03 (s, CHO).

IR (CH$_2$Cl$_2$, cm$^{-1}$): 1715, 1695.

EXAMPLE 75

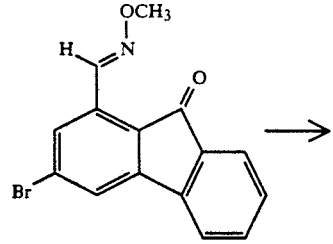

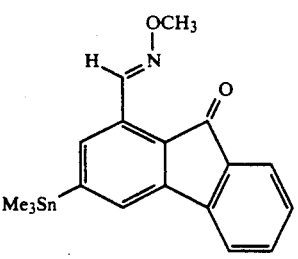

3-Trimethylstannyl-1-methoxyiminomethyl-9-fluorenone

3-Bromo-1-methoxyiminomethyl-9-fluorenone (100 mg) is treated under the conditions of Example 69 to give the product.

EXAMPLE 76

3-Trimethylstannyl-6-methoxyiminomethyl-9-fluorenone

Treatment of the corresponding bromide under the conditions of Example 69, there is obtained the corresponding stannyl fluorenone derivative.

EXAMPLE 77

3-Trimethylstannyl-7-methoxyiminomethyl-9-fluorenone

Treatment of the corresponding bromide under the conditions of Example 69, there is obtained the corresponding stannyl fluorenone derivative.

EXAMPLE 78

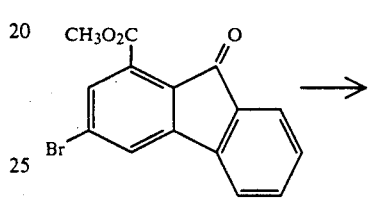

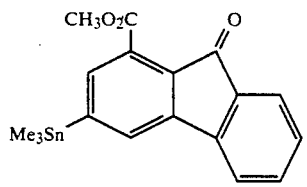

Methyl 3-trimethylstannyl-9-fluorenone-1-carboxylate

Methyl 3-bromo-9-fluorenone-1-carboxylate (104 mg) was treated with hexamethyldistannane as described for the preparation of 3-trimethylstannyl-1-hydroxymethyl-9-fluorenone, Example 69, except that heating at 110° was carried out for 1.75 hours. Purification of the crude product by tlc gave the desired product (116 mg).

$^1$H-NMR (CDCl$_3$, 200 MHz): δ0.38 (s, Me$_3$Sn); 4.01 (s, OCH$_3$); 7.2–7.8 (m, Ar-H).

EXAMPLE 79

Methyl 3-trimethylstannyl-9-fluorenone-6-carboxylate

Treatment of the corresponding bromide under the conditions of Example 69, there is obtained the corresponding stannyl fluorenone derivative.

EXAMPLE 80

Methyl 3-trimethylstannyl-9-fluorenone-7-carboxylate

Treatment of the corresponding bromide under the conditions of Example 69, there is obtained the corresponding stannyl fluorenone derivative.

EXAMPLE 81 p-Nitrobenzyl 3-trimethylstannyl-9-fluorenone-1-carboxylate

Treatment of the corresponding bromide under the conditions of Example 69, there is obtained the corresponding stannyl fluorenone derivative.

EXAMPLE 82 p-Nitrobenzyl 3-trimethylstannyl-9-fluorenone-6-carboxylate

Treatment of the corresponding bromide under the conditions of Example 69, there is obtained the corresponding stannyl fluorenone derivative.

EXAMPLE 83 p-Nitrobenzyl 3-trimethylstannyl-9-fluorenone-7-carboxylate

Treatment of the corresponding bromide under the conditions of Example 69, there is obtained the corresponding stannyl fluorenone derivative.

EXAMPLE 84

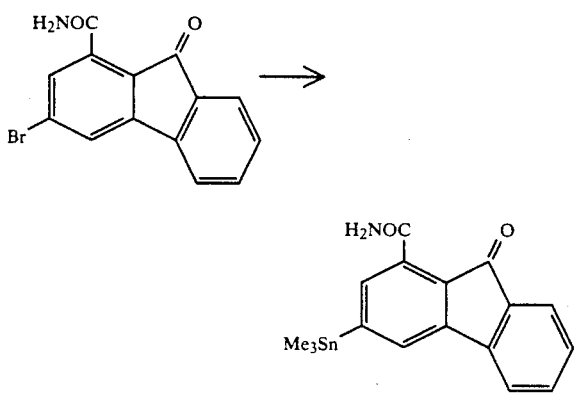

3-Trimethylstannyl-9-fluorenone-1-carboxamide

3-Bromo-9-fluorenone-1-carboxamide from Example 106 was treated under the conditions described for the preparation of methyl 3-trimethylstannyl-9-fluorenone-1-carboxylate, Example 78, to give after heating for 1.35 hours and preparative tlc, the desired product (22 mg).

$^1$H-NMR (CDCl$_3$, 200 MHz): δ0.38 (s, Me$_3$Sn); 7.2–7.75 (m, Ar-H); 7.81 (s, ArH); 8.38 (s, ArH).

EXAMPLE 85

3-Trimethylstannyl-9-fluorenone-6-carboxamide

Treatment of the corresponding bromide under the conditions of Example 69, there is obtained the corresponding stannyl fluorenone derivative.

EXAMPLE 86

3-Trimethylstannyl-9-fluorenone-7-carboxamide

Treatment of the corresponding bromide under the conditions of Example 69, there is obtained the corresponding stannyl fluorenone derivative.

EXAMPLE 87

N-methyl-3-trimethylstannyl-9-fluorenone-1-carboxamide

Treatment of the corresponding bromide under the conditions of Example 69, there is obtained the corresponding stannyl fluorenone derivative.

EXAMPLE 88

N-methyl-3-trimethylstannyl-9-fluorenone-6-carboxamide

Treatment of the corresponding bromide under the conditions of Example 69, there is obtained the corresponding stannyl fluorenone derivative.

EXAMPLE 89

N-methyl-3-trimethylstannyl-9-fluorenone-7-carboxamide

Treatment of the corresponding bromide under the conditions of Example 69, there is obtained the corresponding stannyl fluorenone derivative.

EXAMPLE 90

N,N-dimethyl-3-trimethylstannyl-9-fluorenone-1-carboxamide

Treatment of the corresponding bromide under the conditions of Example 69, there is obtained the corresponding stannyl fluorenone derivative.

EXAMPLE 91

N,N-dimethyl-3-trimethylstannyl-9-fluorenone-6-carboxamide

Treatment of the corresponding bromide under the conditions of Example 69, there is obtained the corresponding stannyl fluorenone derivative.

EXAMPLE 92

N,N-dimethyl-3-trimethylstannyl-9-fluorenone-7-carboxamide

Treatment of the corresponding bromide under the conditions of Example 69, there is obtained the corresponding stannyl fluorenone derivative.

EXAMPLE 93

3-Trimethylstannyl-1-methylthio-9-fluorenone

Treatment of the corresponding bromide under the conditions of Example 69, there is obtained the corresponding stannyl fluorenone derivative.

EXAMPLE 94

3-Trimethylstannyl-6-methylthio-9-fluorenone

Treatment of the corresponding bromide under the conditions of Example 69, there is obtained the corresponding stannyl fluorenone derivative.

EXAMPLE 95

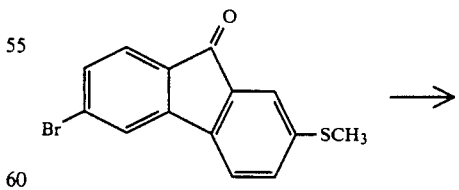

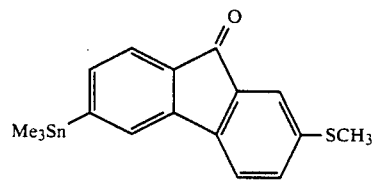

3-Trimethylstannyl-7-methylthio-9-fluorenone

Treatment of the corresponding 3-bromo derivative described in Example 108 under the conditions described for 3-trimethylstannyl-1-hydroxymethyl-9-fluorenone, Example 69, the desired product was obtained.

¹H-NMR (CDCl₃, 200 MHz): δ0.28 (s, Me₃Sn); 2.46 (s, SCH₃); 7.2–7.55 (m, Ar-H).

EXAMPLE 96

3-Trimethylstannyl-1-methylsulfinyl-9-fluorenone

Treatment of the corresponding bromide under the conditions of Example 69, there is obtained the corresponding stannyl fluorenone derivative.

EXAMPLE 97

3-Trimethylstannyl-6-methylsulfinyl-9-fluorenone

Treatment of the corresponding bromide under the conditions of Example 69, there is obtained the corresponding stannyl fluorenone derivative.

EXAMPLE 98

3-Trimethylstannyl-7-methylsulfinyl-9-fluorenone

Treatment of the corresponding bromide under the conditions of Example 69, there is obtained the corresponding stannyl fluorenone derivative.

EXAMPLE 99

3-Trimethylstannyl-1-methylsulfonyl-9-fluorenone

Treatment of the corresponding bromide under the conditions of Example 69, there is obtained the corresponding stannyl fluorenone derivative.

EXAMPLE 100

3-Trimethylstannyl-6-methylsulfonyl-9-fluorenone

Treatment of the corresponding bromide under the conditions of Example 69, there is obtained the corresponding stannyl fluorenone derivative.

EXAMPLE 101

3-Trimethylstannyl-7-methylsulfonyl-9-fluorenone

Treatment of the corresponding bromide under the conditions of Example 69, there is obtained the corresponding stannyl fluorenone derivative.

EXAMPLE 102

3-Bromo-1-hydroxymethyl-9-fluorenone

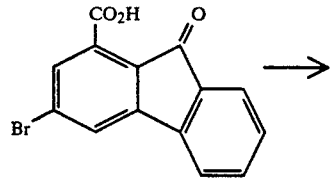

Step A: Preparation of 3-bromo-1-hydroxymethyl-9-fluorenol

3-Bromo-9-fluorenone-1-carboxylic acid, Example 100, (1.23 g) was dissolved in 20 ml THF and treated with BH₃. THF (8 ml, 1M soln in THF, 2 eq). The reaction mixture was allowed to stir overnight at room temperature under N₂. HCl (2N soln) was added and stirring continued until H₂ evolution ceased. The reaction mixture was diluted with water and extracted with EtOAc, dried and evaporated which gave the solid product (1.23 g), which was used without further purification in the next step.

¹H-NMR (CDCl₃, 200 MHz): δ4.71, 4.98 (2d, J=12, Ar-CH₂OH); 5.73 (s, ArCHOHAr); 7.3–7.8 (m, Ar-H).

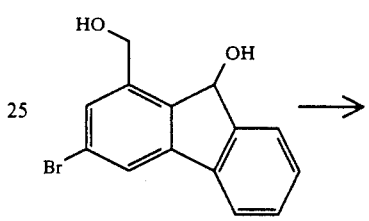

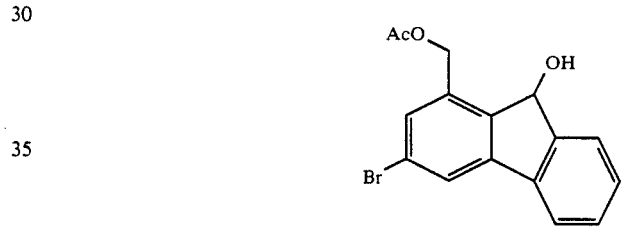

Step B: Preparation of 3-bromo-3-acetoxymethyl-9-fluorenol

3-Bromo-1-hydroxymethyl-9-fluorenol (1.23 g) was dissolved in pyridine (5 ml) and treated with Ac₂O (1.1 eq). The reaction mixture allowed to stir at r.t. for 1 hour. The pyridine was evaporated off under reduced pressure, the residue dissolved in EtOAc, washed with 1N HCl followed by NaHCO₃ (10% soln) then dried and evaporated to give the crude product which by chromatography on silica-gel gave the desired product (0.406 g) along with starting material (0.252 g) and 3-bromo-1-acetoxymethyl-9-acetoxyfluorene (0.406 g).

¹H-NMR (CDCl₃, 200 MHz): δ2.16 (s, CH₃-C=O); 5.30, 5.44 (2d, J=14, Ar-CH₂O—); 5.68 (s, ArCHOHAr); 7.3–7.8 (m, Ar-H).

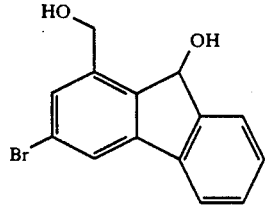

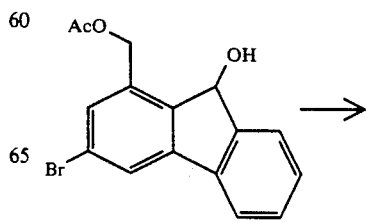

EXAMPLE 103

3-Bromo-9-fluorenone-1-carboxylic acid

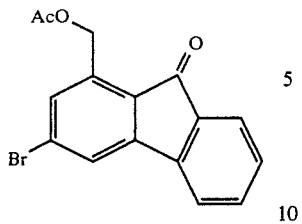

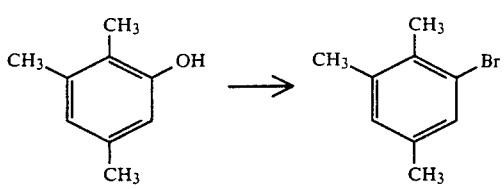

Step C: Preparation of 3-bromo-1-acetoxymethyl-9-fluorenone

Dichloromethane (5 ml) was cooled to −60° C. under $N_2$, oxalyl chloride (1.65 ml, 1M soln in $CH_2Cl_2$, 1.1 eq) was added followed by DMSO (234 μl in 1 ml of ($CH_2Cl_2$). The resulting solution was stirred at −60° for 10 minutes. The 3-bromo-1-acetoxymethyl-9-fluorenol (0.480 g) in a suspension of $CH_2Cl_2$ (2 ml) was added dropwise and the solution stirred at −60° for 0.5 hour. Triethylamine (1.06 ml) was added dropwise and the solution stirred at −60° for 15 minutes. The cooling bath was removed and water (5 ml) was added and the reaction mixture stirred at room temperature for 20 minutes. The organic phase was separated and the aqueous phase was extracted with EtOAc, the combined organic extract was dried and evaporated which gave product, one spot on tlc, used without further purification in the next step.

Step A: Preparation of 1-Bromo-2,3,5-trimethylbenzene

Triphenylphosphine 57.6 g was suspended in 50 ml $CH_3CN$ and cooled to 0° C. under nitrogen. Bromine 11.2 ml (35.2 g) in 60 ml $CH_3CN$ was added dropwise over ½ hour. The ice bath was removed and 27.2 g of the phenol in 40 ml $CH_3CN$ was added all at once. The reaction mixture was heated to 60°-70° for 30 minutes; the solids went into solution. The acetonitrile was distilled off under house vac while the oil bath temperature was raised to 110°. When $CH_3CN$ stopped distilling, the reaction flask was fitted with a wide bore glass tubing, the top of which was connected by rubber tubing to a 500 ml 3 neck flask filled with 200 ml $H_2O$, one neck was stoppered and the other neck was connected to a nitrogen bubbler. The reaction mixture was heated in a sand bath to 340° for 4 hours. After a short while a liquid started to reflux in the glass tubing. The glass tubing was replaced with a distillation unit and the liquid in the flask was distilled out b.p. about 190°, at line vacuum to give 22 g of desired product. Care should be taken to turn the vacuum on gradually as the high sand bath temperature will make the liquid flash out. A high temperature was required to get most of the product from the pot residue which was molten triphenylphosphine oxide.

$^1$H-NMR (CDCl$_3$, 200 MHz): δ2.25, 2.28, 3.01 (3s, CH$_3$-Ar); 6.88, 7.21 (2S, Ar-H).

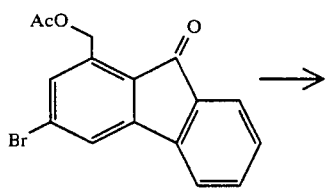

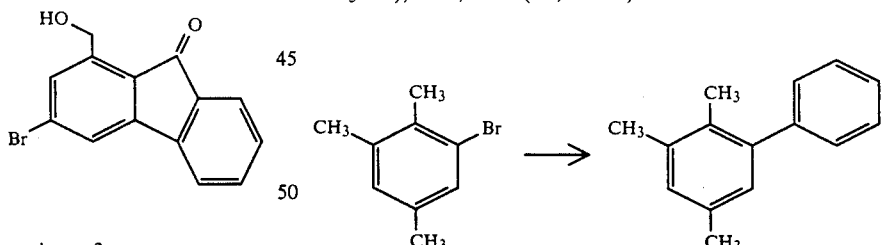

Step D: Preparation of 3-bromo-1-hydroxymethyl-9-fluorenone

The product from the previous reaction was dissolved in MeOH (5 ml) and treated with NaOMe (0.054 ml, 5.5M soln in MeOH, 0.2 eq). The mixture was allowed to stir at room temperature for 1 hour. The MeOH was removed under reduced pressure and the residue was taken up in EtOAc and washed with pH 7 buffer, water and sat'd NaCl solution, dried and evaporated which gave crude product 0.396 g. Purification by preparative tlc (20% EtOAc/hexane elution) gave pure product (0.289 g).

$^1$H-NMR (CDCl$_3$, 200 MHz): δ4.01 (t, J=6, OH); 4.86 (d, J=6, Ar-CH$_2$OH); 7.3-7.8 (m, Ar-H).

Step B: Preparation of 1-Phenyl-2,3,5-trimethylbenzene

The bromo compound 5 g was treated with 4.6 g $C_6H_5B(OH)_2$, 50 ml toluene, 25 ml Na$_2$CO$_3$ (2 H), 12.5 ml MeOH and 0.21 g tetrakistriphenylphosphine palladium. The reaction mixture was heated under nitrogen overnight and worked by extraction with ether, washing with water, saturated NaCl and drying and evaporation. The dark brown residue was passed through silica gel (120 g) using hexane as eluant. The hexane eluant after evaporation gave 4.5 g product.

$^1$H-NMR (CDCl$_3$, 200 MHz): δ2.17 (s, Ar-CH$_3$); 2.33 (s, 2s, Ar-CH$_3$); 6.92 (s, Ar-H); 7.01 (s, Ar-H); 7.2-7.5 (m, Ar-H).

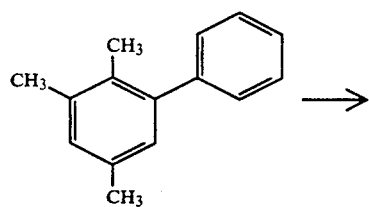

→

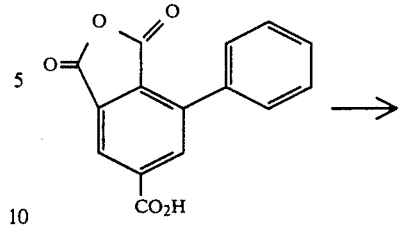

→

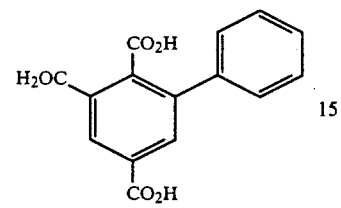

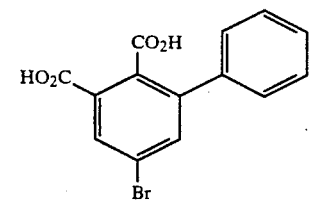

Step C: Preparation of 1-phenyl-benzene-2,3,5tricarboxylic acid

The trimethylbiphenyl (18 g) was suspended in 1.8 L of water, KMnO₄ (103 g) was added followed by 14.2 g Na₂CO₃. The reaction was refluxed gently overnight. The KMnO₄ was completely reacted but an oil was still floating on the surface (unreacted starting material). The solution was filtered and the residue (MnO₂) was washed with water. The filtrate and washings were extracted with ether. The aqueous phase was acidified and extracted with EtOAc 3×300 ml. The EtOAc extract was dried and evaporated to give 11.5 g of triacid.

From the ether extract after drying and evaporation 4.8 g of starting material was recovered.

¹H-NMR (D₂O, NaOD, 200 MHz): δ7.23 (m, Ar-H); 7.78 (s, Ar-H); 7.95 (s, Ar-H).

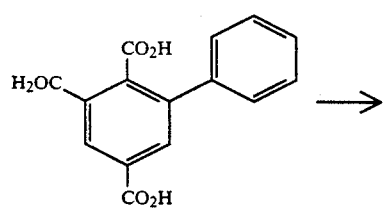

→

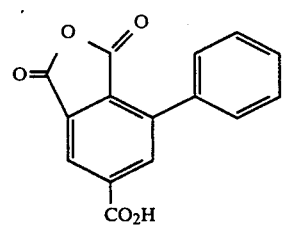

Step D: Preparation of 1-phenyl-benzene-2,3,5-tricarboxylic acid 2,3-anhydride The triacid 11.5 g was heated at 230° under line vac for 1 hour. Allowed to cool to room temperature which gave the anhydride.

¹H-NMR (CD₃COCD₃, 200 MHz): δ7.34 (m, Ar-H); 7.72 (m, Ar-H); 8.46 (s, Ar-H); 8.49 (s, Ar-H).

IR (neat, cm⁻¹) 1830, 1782, 1705.

Step E: Preparation of 1-Phenyl-5-bromobenzene-2,3-dicarboxylic acid

1-Phenyl-benzene-2,3,5-tricarboxylic acid 2,3-anhydride 4.2 g was suspended in 200 ml CH₂Cl₂, under N₂ and treated with 15.7 ml of a 2M solution of oxalyl chloride in CH₂Cl₂. DMF (0.2 ml) was added and the mixture allowed to stir at room temperature for three hours during which the original solid dissolved and a new solid precipitated out. The solvent and excess oxalyl chloride were evaporated off under reduced pressure to give the acid chloride. This was suspended in BrCCl₃ (20 ml) and heated under N₂ to 100°. A solution of 2-mercaptopyridine-N-oxide (2.5 g) and azobisisobutyronitrile (1.4 g) in 2 ml CH₂Cl₂, and pyridine 1.24 ml in 25 ml BrCCl₃, was added dropwise over 0.5 hour and heating was continued another 0.5 hour. The reaction mixture was cooled and evaporated to remove the BrCCl₃ and the residue was stirred with excess 2N NaOH for 10 minutes. The basic solution was extracted twice with ether, then acidified and extracted again with EtOAc. The second EtOA extract was dried and evaporated to give a solid mixture of acids. Extraction with hot CHCl₃ gave the desired product 1.22 g. The CHCl₃ insoluble material was 1-phenylbenzene-2,3,5-tricarboxylic acid (3.2 g).

¹H-NMR (CDCl₃, 200 MHz): δ(7.36 (broad s, Ar-H); 7.7 (s, Ar-H); 8.13 (s, Ar-H).

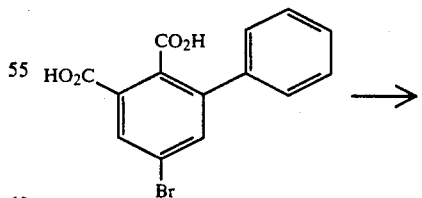

→

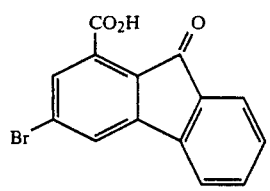

Step F: Preparation of 3-bromo-9-fluorenone-1-carboxylic acid

1-Phenyl-5-bromobenzene-2,3-dicarboxylic acid (1.2 g) was dissolved in H₂SO₄ (20 ml) and heated at 40° for 6 hours. The solution was cooled and added to ice (50 g). The precipitated yellow product was filtered and washed with water and air dried. The filtrate and washings were extracted with CH₂Cl₂ and washed once with saturated NaCl solution, then dried and evaporated which gave more of the product. Total yield 0.84 g.

$^1$H-NMR (CDCl₃, 200 MHz): δ7.3–7.8 (m, Ar-H); 7.84 (s, Ar-H); 8.33 (s, Ar-H).

EXAMPLE 104 p-Nitrobenzyl 3-bromo-9-fluorenone-1-carboxylate

Using the carboxylic acid of Example 103, Step F and treating with one equivalent of sodium hydride in dimethylformamide to deprotonate followed by treatment with p-nitrobenzyl bromide in dimethylformamide for two hours at room temperature will afford the above named compound.

EXAMPLE 105

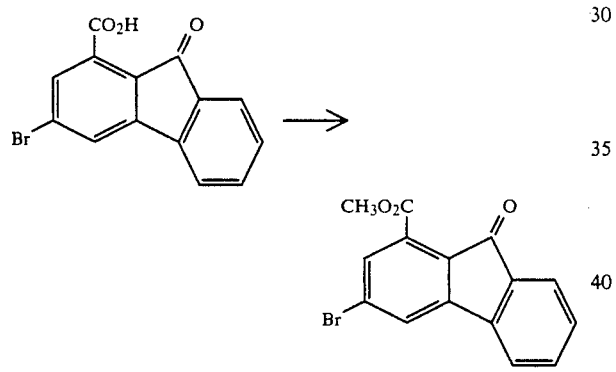

Methyl 3-bromo-9-fluorenone-1-carboxylate

3-Bromo-9-fluorenone-1-carboxylic acid, Example 103, (100 mg) was suspended in CH₂Cl₂ (2 ml) and treated with excess CH₂N₂ in ether. The mixture was allowed to stand at room temperature for 1 hour. Nitrogen was bubbled into the reaction mixture to remove unreacted CH₂N₂. The solvent was removed under reduced pressure to give the crude ester. Preparative tlc gave the product (47 mg).

$^1$H-NMR (CDCl₃, 200 MHz): δ4.02 (s, OCH3); 7.3–7.8 (m, Ar-H).

EXAMPLE 106

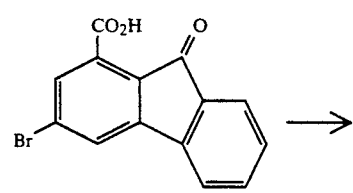

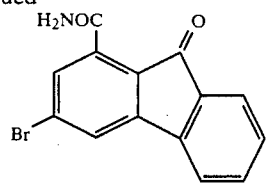

3-Bromo-9-fluorenone-1-carboxamide

3-Bromo-9-fluorenone-1-carboxylic acid, Example 103, (64 mg) was suspended in CH₂Cl₂ (2 ml), 1-hydroxybenzotriazole (31.4 mg, 1.1 eq) was added followed by DCC (48 mg, 1.1 eq). The reaction mixture was stirred at room temperature for 1 hour. The precipitated dicyclohexylurea was filtered off and the residue washed with a little cold CH₂Cl₂. The filtrate and washings were treated with excess NH₃ bubbled slowly into the solution. This was allowed to stir for 15 minutes. The yellow precipitate was filtered off and suspended in Na₂CO₃ soln (2 ml, 2M) and stirred for 15 minutes, then filtered and washed with water. The residue was dried to give the amide which was used without purification in Example 81.

EXAMPLE 107

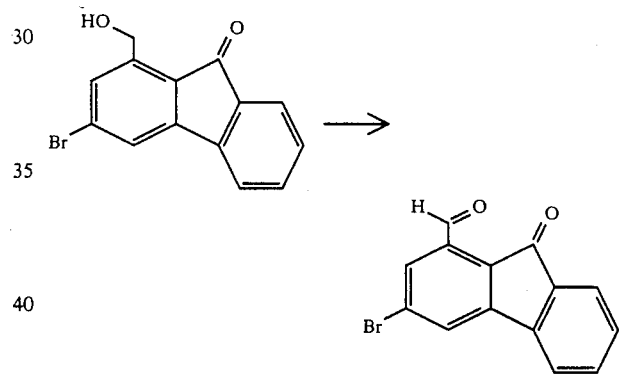

3-Bromo-9-fluorenone-1-carboxaldehyde

3-Bromo-1-hydroxymethyl-9-fluorenone, Example 102, (200 mg) was dissolved in CH₂Cl₂ (4 ml) and treated with N-methylmorpholine-N-oxide (1.1 eq), molecular sieves # 3A (200 mg, finely powdered) was added, followed by tetra-n-propylammonium perruthenate (50 mg). The reaction mixture was stirred at room temperature for 20 minutes and then filtered through a small bed of silica gel and washed with EtOAc/hexane 1:1 mixture until the product was all eluted off. The total eluate was evaporated to give the product.

EXAMPLE 108

3-Bromo-7-methyl-9-fluorenone

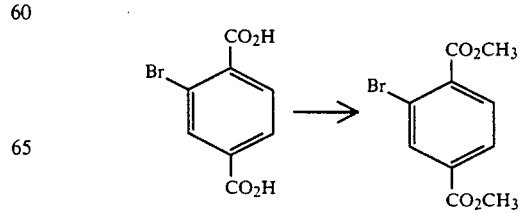

Step A: Preparation of Dimethyl-2-bromoterepthalate

2-Bromoterepthalic acid (14.2 g.) was treated with thionyl chloride (35 ml) and the reaction mixture was heated at reflux overnight. The reaction mixture was cooled and the excess SOCl₂ was removed under reduced pressure. The residue was treated with methanol (174 ml) at −10° C. over a one half hour period followed by triethylamine (17.4 ml). After 15 minutes at room temperature, the methanol was removed under reduced pressure. The residue was then taken up in ethyl ether, washed with water, dried and evaporated gave a white solid (14.65 g).

¹H-NMR (CDCl₃, 200 MHz): δ3.87 (s, CH₃); 7.8–8.32 (m, ArH).

IR (CH₂Cl₂, cm⁻¹); 1720.

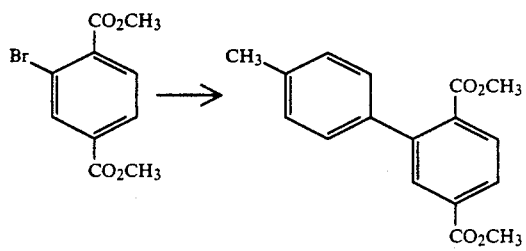

Step B: Preparation of Dimethyl-2-(4-toluyl)-terepthalate

4-Bromotoluene (6 g) was dissolved in tetrahydrofuran (20 ml). To this solution at −78° C. under N₂ was added over a ten minute period, 1.7M tBuLi (42 ml). After two hours at room temperature, the reaction mixture was cooled to 0° C. and 1M ZnCl₂ (36 ml) was added over a ten minute period. After one half hour at room temperature, bis(triphenylphosphine)nickel(II) chloride (1.32 g) was added followed by dimethyl-2-bromo-terepthalate (6 g) in tetrahydrofuran (20 ml) dropwise over a five minute period. The reactin mixture was stirred at room temperature for two hours. The tetrahydrofuran was removed under reduced pressure. The residue was treated with ethyl acetate and 1N HCl and the layers separated. The organic phase was washed with water, brine, dried over magnesium sulfate and evaporated gave the crude product. Chromatography on silica gel using 5% hexanes/methylene chloride gave the desired product (5.33 g).

¹H-NMR (CDCl₃, 200 MHz): δ2.42 (s, CH₃); 3.71, 3.96 (2s, CH₃O): 7.24–8.11 (m, ArH).

IR (CH₂Cl₂, cm⁻¹): 1720.

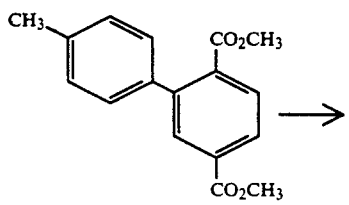

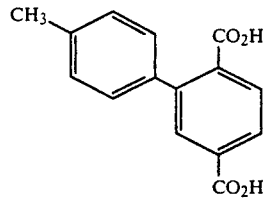

Step C: Preparation of 2-(4-toluyl)terepthalic acid

Dimethyl-2-(4-toluyl)terepthalate (11.88 g) was suspended in methanol (99 ml). 5M NaOH (50 ml) was added. The reaction mixture was heated at reflux for 1.5 hours. The methanol was removed under reduced pressure. The residue was treated with ethyl acetate and water and the layers separated. The aqueous layer was washed once with ethyl acetate. The aqueous layer was then acidified with 2N HCl and extracted three times with ethyl acetate. These combined organic extracts were then dried over MgSO₄, filtered and evaporated under reduced pressure gave the product (7.09 g)

¹H-NMR (DMSO, 200 MHz): δ2.34 (s, CH₃); 7.24–8.08 (m, ArH).

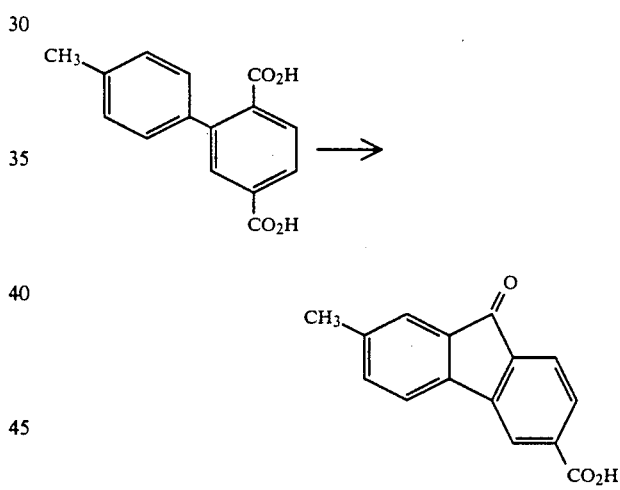

Step D: Preparation of 7-methyl-9-fluorenone-3-carboxylic acid 2-(4-Toluyl)-terepthalic acid (7 g) at 0° C. was suspended in concentrated H₂SO₄ (41 ml). The reaction mixture was heated at 40° C. for four hours (a black solution develops). Ice was added to the reaction mixture and the precipitated yellow solid was filtered, washed well with water and dried under high vacuum. The filtrate was extracted three times with ethyl acetate. The combined organic layers were dried with MgSO₄, filtered and evaporated under reduced pressure gave the desired product as a yellow solid. This was combined with the precipitated yellow solid gave 6.5 g of the desired product.

¹H-NMR (DMSO, 200 MHz): δ2.33 (s, CH₃); 7.42–8.21 (m, ArH).

Step E: Preparation of 7-methyl-9-fluorenone-3-carboxylic chloride

7-Methyl-9-fluorenone-3-carboxylic acid (6.5 g) was suspended in methylene chloride (110 ml) at 0° C. 2M Oxalyl chloride (30 ml) was added followed by DMF (1.17 ml added over a three hour period). The reaction mixture was stirred at room temperature for twenty hours. The reaction mixture was filtered and the methylene chloride was removed under reduced pressure gave the crude product (7.0 g).

$^1$H-NMR (CDCl$_3$, 200 MHz): δ2.42 (s, CH$_3$); 7.38-8.41 (m, ArH).

Step F: Preparation of 3-bromo-7-methyl-9-fluorenone

7-Methyl-9-fluorenone-3-carboxylic acid chloride (7 g.) was dissolved i BrCCl$_3$ (130 ml), AIBN (2.33 g.) in methylene chloride (20 ml.) was added. This solution was then added dropwise over a 45 minute period to a suspension of the sodium salt of 2-mercaptopyridine-N-oxide (6.13 g.) in BrCl$_3$ (70 ml.) at 100° C. Additional AIBN (235 mg.) in a minimum of methylene chloride was then added. The reaction mixture was stirred at 100° C. for twenty minutes, diluted with methylene chloride, washed with aqueous sodium bicarbonate, dried and evaporated. The residue was chromatographed on silica gel using 50% hexanes/methylene chloride gave the desired product (2.9 g).

$^1$H-NMR (CDCl$_3$, 200 MHz): δ2.41 (s, CH$_3$); 7.32-7.64 (m, ArH).

IR (CH$_2$Cl$_2$, cm$^{-1}$): 1715.

EXAMPLE 109

3-bromo-7-hydroxymethyl-9-fluorenone

Step A: Preparation of 7-bromomethyl-3-bromo-9-fluorenone

3-Bromo-7-methyl-9-fluorenone Example 108 (2.6 g) was dissolved in CCl$_4$ (70 ml). To this solution at 80° C. was added NBS (1.78 g) and AIBN (260 mg). After one half hour, additional AIBN (520 mg) was added. At fifteen hours, additional NBS (178 mg) was added. The reaction mixture was stirred at reflux for 22.5 hours. Carbon tetrachloride was removed under reduced pressure. Residue was then diluted with ethyl acetate, washed twice with water, once with brine, dried and evaporated gave the crude product. Crystallization from 50% ethyl acetate/hexanes gave the pure product (1.7 g), as well as a 1/1 mixture of 7-dibromomethyl-3-bromo-9-fluorenone and 7-bromomethyl-3-bromo-9-fluorenone (476 mg) in the mother liquors.

$^1$H-NMR (CDCl$_3$, 200 MHz): δ4.52 (s, CH$_2$Br); 7.44-7.68 (m, ArH).

IR (CH$_2$Cl$_2$, cm$^{-1}$): 1720.

Step B: Preparation of 3-bromo-7-acetoxymethyl-9-fluorenone

7-Bromomethyl-3-bromo-9-fluorenone (1.7 g) was suspended in DMF (25 ml). To this suspension was added potassium acetate (576 mg). The reaction mixture was stirred at 100° C. for one hour. It was then diluted with ethyl acetate, washed four times with water, twice with brine, dried and evaporated. The residue was chromatographed on silica gel using 2% ethyl acetate/methylene chloride and gave the desired product (1.18 g).

$^1$H-NMR (CDCl$_3$, 200 MHz): δ2.12 (s, CH$_3$—C=O); 7.42–7.68 (m, ArH).

IR (CH$_2$Cl$_2$, cm$^{-1}$): 1720.

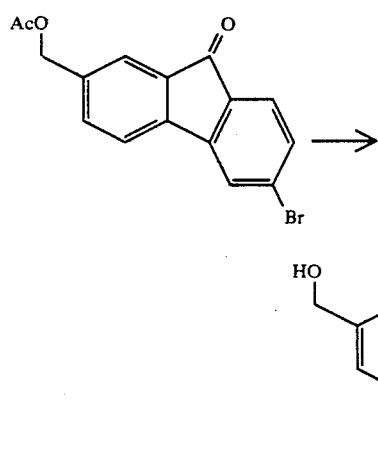

Step C: Preparation of 3-bromo-7-hydroxymethyl-9-fluorenone 3-bromo-7-acetoxymethyl-9-fluorenone (1.18 g) was suspended in methanol (102 ml) and THF (23 ml). To this suspension was added 0.045M NaOMe (6.6 ml). The reaction mixture was stirred at room temperature for 1.25 hours. It was then neutralized with 0.2M pH 7 phosphate buffer. The tetrahydrofuran and methanol were removed under reduced pressure. Reaction mixture was then diluted with ethyl acetate, washed with water and brine, dried and evaporated gave the product (1.0 g).

$^1$H-NMR (DMSO, 200 MHz): δ4.53 (d, J=6, CH$_2$OH); 5.35 (t, J=6, OH); 7.46–8.06 (m, ArH).

EXAMPLE 110

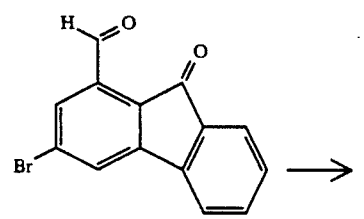

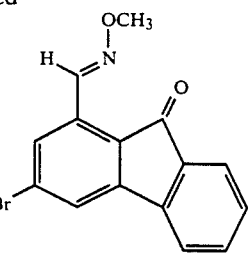

3-Bromo-1-methoxyiminomethyl-9-fluorenone

3-Bromo-9-fluorenone-1-carboxaldehyde, Example 103, (100 mg) was dissolved in THF (4 ml) and treated with O-methylhydroxylamine (1.1 eq) for 1 hour. The solvent was evaporated and the residue was purified by preparative tlc to give the product.

EXAMPLE 111

3-bromo-7-formyl-9-fluorenone

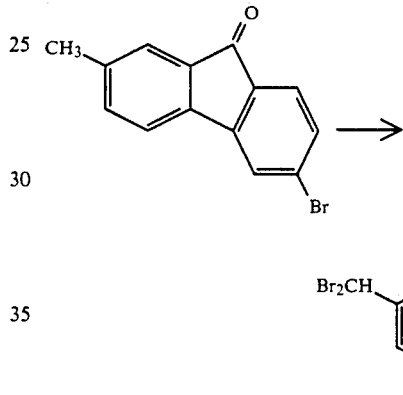

Step A: Preparation of 7-dibromomethyl-3-bromo-9-fluorenone

3-Bromo-7-methyl-9-fluorenone (300 mg) was dissolved in CCl$_4$ (18 ml). To this solution at 80° C. was added NBS (450 mg) and AIBN (30 mg). After one half hour, additional AIBN (60 mg) was added. Reaction mixture stirred at reflux for 65 hours. Carbon tetrachloride was removed under reduced pressure. Residue was then diluted with ethyl acetate and washed twice with H$_2$O, once with brine, dried and evaporated gave the crude product (493.1 mg). Crystallization from 50% ethyl acetate/hexanes gave the pure product (137.1 mg) as well as extensive amounts of desired product in the mother liquors.

$^1$H-NMR (CDCl$_3$, 200 MHz): δ6.68 (s, CHBr$_2$); 7.49–7.94 (m, ArH).

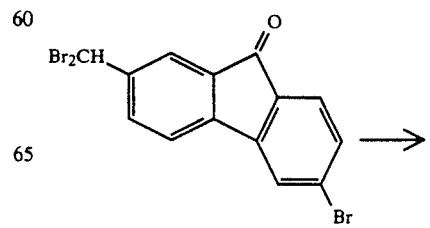

-continued

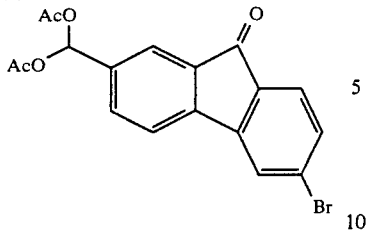

Step B: 7-diacetoxymethyl-3-bromo-9-fluorenone

To 7-dibromomethyl-3-bromo-9-fluorenone (137.1 mg) in DMF (3.3 ml) was added potassium acetate (78 mg). The reaction mixture was stirred at 100° C. for 70 minutes. It was then diluted with ethyl acetate, washed four times with H$_2$O, twice with brine, dried and evaporated. The residue was purified by preparative tlc using 1% ethyl acetate/methylene chloride gave a mixture of the diacetate and the ultimately desired aldehyde (68.4 mg).

$^1$H-NMR (CDCl$_3$ 200 MHz): δ2.16 (s, CH$_3$C=O); 7.68 (s, CH-OAc$_2$); 7.44–7.86 (m, ArH).

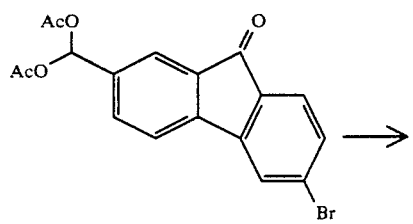

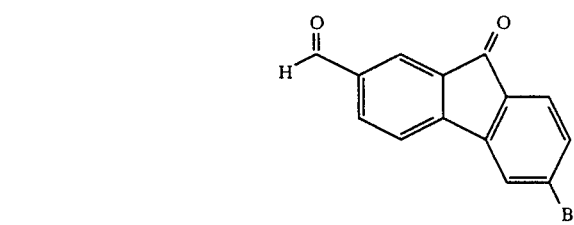

Step C: Preparation of 3-bromo-7-formyl-9-fluorenone

7-Diacetoxymethyl-3-bromo-9-fluorenone (61.1 mg) was suspended in methanol (4.4 ml) and THF (1.0 ml). To this suspension was added 0.054M NaOMe (0.56 ml). The reaction mixture was stirred at room temperature for 22.5 hours. It was then neutralized with 0.2M pH 7 phosphate buffer. The THF and methanol were removed under reduced pressure. Reaction mixture was then diluted with ethyl acetate, washed with water and brine, dried and evaporated gave the crude product (47.5 mg).

$^1$H-NMR (DMSO, 200 MHz): d 7.44–7.86 (m, ArH), 10.07 (s, CH=O).

EXAMPLE 112

3-bromo-7-methylthio-9-fluorenone

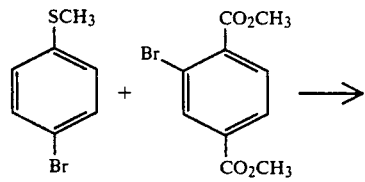

-continued

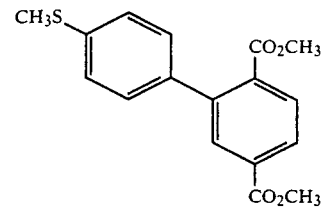

Step A: Preparation of Dimethyl 2-thioanisylterepthalate

4-Bromothioanisole (7.1 g) was dissolved in tetrahydrofuran (23 ml). To this solution at −78° C. under nitrogen was added over a ten minute period 1.7M tBuLi (48 ml). After 45 minutes at room temperature, 1M ZnCl$_2$ (41 ml) was added dropwise over a ten minute period. After one half hour at room temperature, bis(triphenylphosphine)nickel(II) chloride (1.4 g) was added followed by dimethyl-2-bromoterepthalate (4.67 g) in tetrahydrofuran (47 ml). The reaction mixture was stirred at room temperature for 45 minutes. The THF was removed under reduced pressure. The residue was treated with ethyl acetate and 1N HCl and the layers separated. The organic phase was washed with water, brine, dried over magnesium sulfate and evaporated gave the crude product. Chromatography on silica gel using 15% ethyl acetate/hexanes gave the desired product (3.92 g).

$^1$H-NMR (CDCl$_3$, 200 MHz): δ2.52 (s, CH$_3$); 3.70, 3.96 (2s, CH$_3$O); 7.20–8.06 (m, ArH).

IR (CH$_2$Cl$_2$, cm$^{-1}$): 1720.

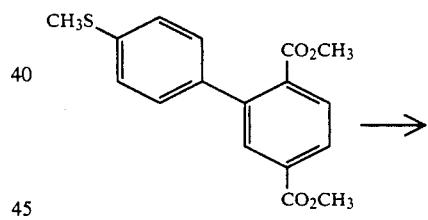

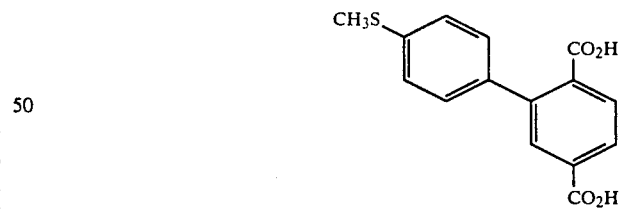

Step B: Preparation of 2-thioanisylterepthalic acid

Dimethyl 2-thioanisylterepthalate (3.92 g) was suspended in methanol (45.9 ml), 5M NaOH (13.5 ml) was added. The reaction mixture was heated at reflux for 1.5 hours. The methanol was removed under reduced pressure. The residues was treated with ethyl acetate and water and the layers separated. The aqueous layer was washed once with ethyl acetate. The aqueous layer was then acidified with 2N HCl and extracted three times with ethyl acetate. These combined organic extracts were then dried over MgSO$_4$, filtered and evaporated under reduced pressure gave the product (2.75 g).

¹H-NMR (D₂O/NaOD, 200 MHz): δ2.38 (s, CH₃); 7.22–7.71 (m, ArH).

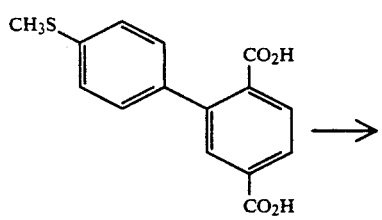

Step C: Preparation of 7-methylthio-9-fluorenone-3-carboxylic acid

2-Thioanisylterepthalic acid (2.75 g) was treated with thionyl chloride (37 ml) and the reaction mixture was heated at reflux for 1.5 hours (becomes a solution as reaction proceeds). The reaction mixture was cooled and the excess SOCl₂ was removed under reduced pressure, gave the acid chloride.

¹H-NMR (CDCl₃, 200 MHz) δ2.54 (s, CH₃); 7.16–8.15 (m, ArH).

The residue was dissolved in methylene chloride (39 ml) and cooled to 0°, 1.1M SnCl₄ in methylene chloride (11.3 ml) was added dropwise over a ten minute period. The reaction mixture was stirred at room temperature for 11.5 hours. After 11.5 hours, water was added to the reaction mixture. After 5 minutes, the reaction mixture was treated with ethyl acetate, acidified with 1N HCl, and the layers separated. After the organic layer was washed with 1N HCl, the combined aqueous layers were washed three times with ethyl acetate. The combined organic layers were dried with MgSO₄ and evaporated and gave the crude product. Trituration with 20% ethyl acetate/hexanes gave the desired product (2.58 g).

¹H-NMR (DMSO, 200 MHz): δ2.54 (s, CH₃); 7.28–8.22 (m, ArH).

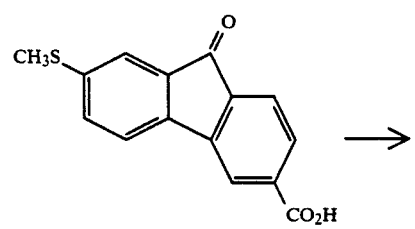

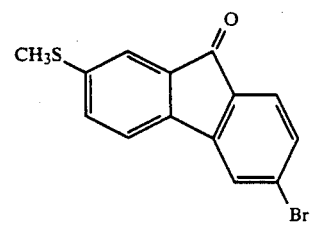

Step D: Preparation of 3-bromo-7-methylthio-9-fluorenone

Treatment of the product from Step C, under the conditions of Steps E and F of Example 108 gave the desired product.

¹H-NMR (CDCl₃, 200 MHz): δ2.52 (s, CH₃); 7.34–7.61 (m, ArH).

EXAMPLE 113

3-Methoxycarbonyl-9-fluorenone-1-carboxylic acid

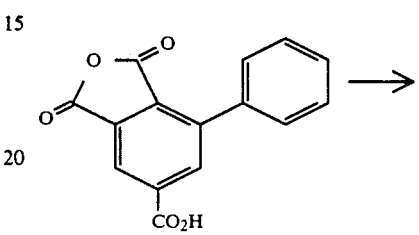

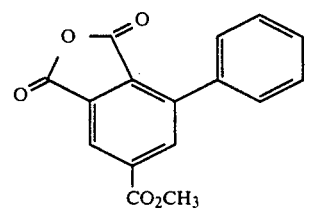

Step A: Preparation of 2-phenyl-benzene-2,3,5-tri-carboxylic acid, 2,3-anhydride-5-methyl-ester The product from Step D, Example 103 was dissolved in Et₂O/CH₂Cl₂ 50/50 200 ml (not completely dissolved). This solution was cooled to 0° and treated with a solution of diazomethane prepared from 20 g of N-nitrosomethylurea in 200 ml of Et₂O. After addition the reaction mixture was stirred until N₂ evolution ceases and a yellow color persists in the reaction mixture. The solution was full of crystals at this point. Excess diazomethane was removed by blowing N₂ through the mixture and the crystals were filtered off and washed with a little ether and dried by suction to give 6.1 g of product. The filtrate was evaporated to dryness and the residue triturated with ether and cooled to 0° and filtered which gave a further 2.5 g of slightly yellow crystals which was also the desired product.

¹H-NMR (CDCl₃, 200 MHz): δ4.03 (s, O—CH₃); 7.54 (m, Ar-H); 8.5 (s, Ar-H); 8.59 (s, Ar-H).

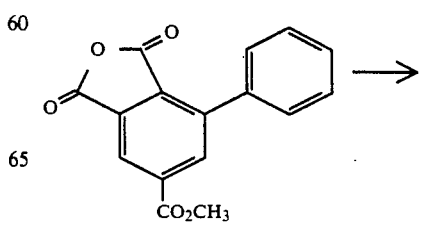

-continued

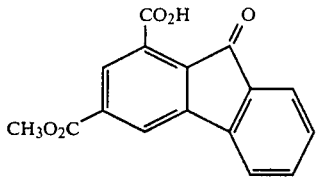

Step B: Preparation of 3-methoxycarbonyl-9-fluorenone-1-carboxylic acid

The 1-phenyl-benzene-2,3,5-tricarboxylic acid, 2,3-anhydride, 5-methyl-ester (4 g) was dissolved in 80 ml of conc. $H_2SO_4$ and heated to 40° for 6 hours. The reaction mixture was cooled and added to solid ice 400 g. The yellow precipitate was filtered (very slow filtration) and washed with a little water. The wet cake was dissolved in THF 100 ml and diluted with 400 ml of $CH_2Cl_2$. The solution was washed with brine, dried over $MgSO_4$ and evaporated to a small volume, which gave the desired product which crystallized out during the evaporation. The product was filtered and dried to give 3.6 g of yellow product.

$^1$H-NMR (CDCl$_3$, 200 MHz): δ4.02 (s, O—CH$_3$); 7.3–7.85 (m, Ar-H); 8.34 (s, Ar-H); 8.81 (s, Ar-H).

EXAMPLE 114

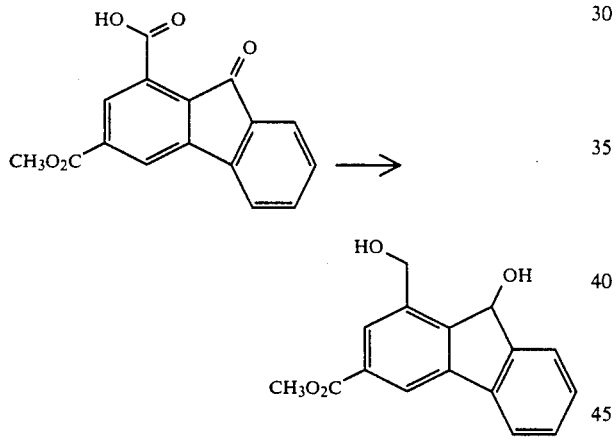

1-Hydroxymethyl-3-methoxycarbonyl-9-fluorenone

Step A: Preparation of 1-hydroxymethyl-3-methoxycarbonyl-9-fluorenol

3-Methoxycarbonyl-9-fluorenone-1-carboxylic acid (0.75 g), from Example 113 was reduced following the procedure of Example 99, Step A, and gave the product (0.74 g).

$^1$H-NMR (CDCl$_3$, 200 MHz): δ3.80 (s, OCH$_3$); 4.64, 4.94 (2d, J=14, ArCH$_2$OH); 5.63 (s, ArCHOHAr); 7.2–7.68 (m, Ar-H); 7.71 (s, ArH); 8.03 (s, ArH).

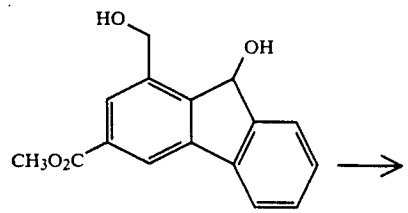

-continued

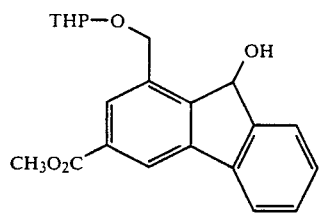

Step B: Preparation of 3-methoxycarbonyl-1-(2-tetrahydropyranyl)oxymethyl-9-fluorenol 3-Methoxycarbonyl-1-hydroxymethyl-9-fluorenol (0.96 g) was treated with dihydropyran (0.43 ml) and p-toluenesulfonic acid (20 mg) in CH$_2$Cl$_2$ (20 ml) for 0.5 hour. The reaction mixture was washed once with NaHCO$_3$ (10% soln) then dried and evaporated to give a mixture of products. Chromatography on silica gel using EtOAc/hexane 1:1 as eluant gave the product (403 mg).

$^1$H-NMR (CDCl$_3$, 200 MHz): δ1.4–2.0 (m, CH$_2$—CH$_2$—CH$_2$); 3.6 (m, CH$_2$—CH$_2$O); 3.94 (s, OCH$_3$); 4.76 (m, ArCH$_2$O); 5.12 (t, OCHO); 5.8 (m, ArCHOHAr); 7.2–8.3 (m, Ar-H).

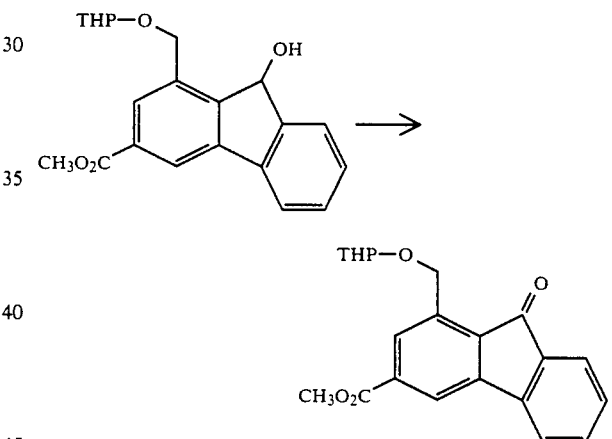

Step C: Preparation of 3-methoxycarbonyl-1-(2-tetrahydropyranyl)oxymethyl-9-fluorenone -fluorenone 3-Methoxycarbonyl-1-(2-tetrahydropyranyl)oxymethyl-9-fluorenol (403 mg) was oxidized under the conditions described in Example 102, Step C, and gave the product.

$^1$H-NMR (CDCl$_3$, 200 MHz): δ1.4–2.0 (m, CH$_2$—CH$_2$—CH$_2$); 3.6 (m, CH$_2$—CH$_2$O); 3.96 (s, OCH$_3$); 4.82 (t, OCHO); 5.04, 5.2 (2d, J=13, ArCH$_2$O); 7.2–7.8 (m, Ar-H); 8.05 (s, ArH); 8.16 (s, ArH).

IR (neat, cm$^{-1}$): 1760, 1712.

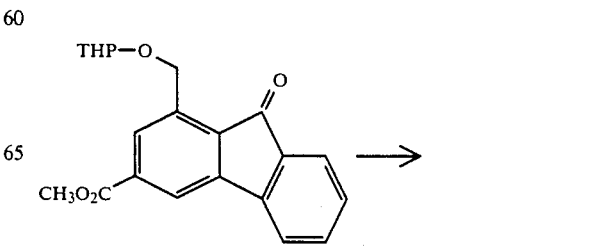

-continued

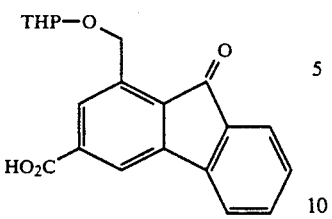

Step D: Preparation of 1-(2-tetrahydropyranyl)oxymethyl-9-fluorenone-3-carboxylic acid 3-Methoxycarbonyl-1-(2-tetrahydropyranyl)oxymethyl-9-fluorenone from the previous reaction was dissolved in MeOH (20 ml) and water (10 ml) and treated with NaOH (2 eq). The reaction mixture was heated in an oil bath at 80° for 1 hour. The reaction mixture was cooled and the MeOH was removed under reduced pressure. The residue was diluted with water and extracted once with EtOAc, then acidified and extracted again with EtOAc. The second EtOAc extract was dried, evaporated, and gave the desired acid (275 mg).

$^1$H-NMR (CDCl$_3$, 200 MHz): δ1.4–2.0 (m, CH$_2$—CH$_2$—CH$_2$); 3.6, 3.95 (2m, CH$_2$—CH$_2$O); 4.87 (t, OCHO); 5.04, 5.22 (2d, J=13, ArCH$_2$O); 7.2–7.7 (m, Ar-H); 8.08 (s, ArH); 8.15 (s, ArH).

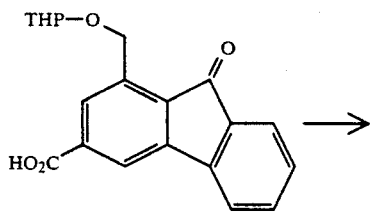

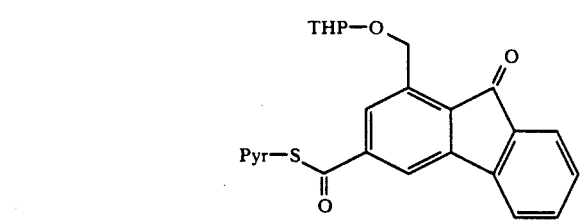

Step E: Preparation of 1-(2-tetrahydropyranyl)oxymethyl-3-(2-pyridyl)-thiocarbonyl-9-fluorenone 1-(2-Tetrahydropyranyl)oxymethyl-9-fluorenone-3-carboxylic acid (57 mg) was dissolved in THF (2 ml). Triphenylphosphine (46.4 mg) and 2,2'-dipyridyl disulfide (39 mg) were added and the reaction mixture was stirred for 2 hours at room temperature. Triphenylphosphine (23.3 mg) and 2,2'-dipyridyl disulfide (20 mg) were again added and the reaction mixture stirred another 2 hours. The reaction mixture was evaporated to dryness and the residue purified by preparative tlc on silica gel using EtOAc/hexane 1:1 as eluant gave the product (75 mg).

$^1$H-NMR (CDCl$_3$, 200 MHz): δ1.4–2.0 (m, CH$_2$—CH$_2$—CH$_2$); 3.6, 3.95 (2m, CH$_2$—CH$_2$O); 4.87 (t, OCHO); 5.1, 5.25 (2d, J=15, ArCH$_2$O); 7.0–8.8 (m, Ar-H and pyridyl-H).

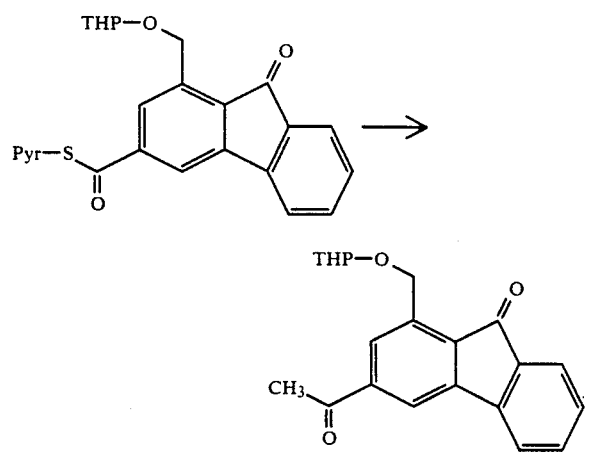

Step F: Preparation of 1-(2-tetrahydropyranyl)oxymethyl-3-methylcarbonyl-9-fluorenone 1-(2-Tetrahydropyranyl)oxymethyl-3-(2-pyridyl)thiocarbonyl-9-fluorenone (470 mg) was dissolved in THF (10 ml) and cooled to −15° under N$_2$. A solution of MeMgBr in THF (1.2 eq) was added dropwise over 5 minutes and the reaction allowed to stir at −15° C. for 0.5 hour. The reaction was quenched with saturated ammonium chloride solution, diluted with EtOAc, and washed with water, sat'd NaCl solution then dried and evaporated to give a residue which was chromatographed on silica gel gave the product (233 mg).

$^1$H-NMR (CDCl$_3$, 200 MHz): δ1.4–2.0 (m, CH$_2$—CH$_2$—CH$_2$); 2.67 (s, CH$_3$CO); 3.6, 3.95 (2m, CH$_2$—CH$_2$O); 4.82 (t, OCHO); 5.06, 5.22 (2d, J=17, ArCH$_2$O); 7.2–7.7 (m, Ar-H); 7.98 (s, ArH); 8.06 (s, ArH).

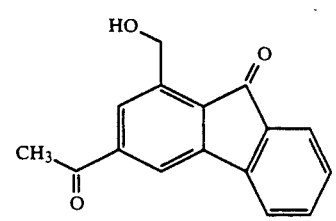

Step G: Preparation of 1-hydroxymethyl-3-methylcarbonyl-9-fluorenone 1-(2-Tetrahydropyranyl)oxymethyl-3-methylcarbonyl-9-fluorenone (197 mg) was dissolved in 1% H$_2$SO$_4$ (5 ml) and allowed to stand at room temperature for 0.5 hour. The reaction mixture was diluted with excess NaHCO$_3$ soln (10%). The MeOH was removed under reduced pressure and the residue was extracted with EtOAc, dried and evaporated gave the product (135 mg).

¹H-NMR (CDCl₃, 200 MHz): δ2.67 (s, CH₃CO); 4.96 (ArCH₂OH); 7.2–7.72 (m, Ar-H); 7.8 (s, ArH); 7.98 (s, ArH).

IR (neat, cm⁻¹): 1710, 1690.

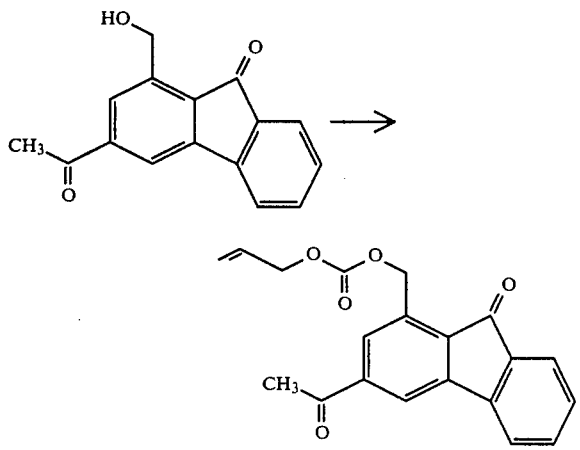

1-Allyloxycarbonyloxymethyl-3-methylcarbonyl-9-fluorenone

1-Hydroxymethyl-3-methylcarbonyl-9-fluorenone (135 mg) was dissolved in THF (4 ml), cooled to 0° C. under N₂. Pyridine (51 μl, 1.2 eq) was added followed by allyloxycarbonyl chloride (70 μl, 1.2 eq). The reaction mixture was allowed to stir overnight allowing it to come to room temperature. The reaction mixture was diluted with methylene chloride, washed with water, sat'd NaCl solution, dried and evaporated. The product was purified by preparative tlc (80 mg).

¹H-NMR (CDCl₃, 200 MHz): δ2.64 (s, CH₃CO); 4.68 (d, CH₂=CHCH₂O); 5.35 (m, CH₂=); 5.68 (s, ArCH₂OH); 7.2–7.7 (m, Ar-H); 7.86 (s, ArH); 7.99 (s, ArH).

IR (neat, cm⁻¹): 1750, 1715, 1695.

EXAMPLE 116

Sodium (5R,6S)-2-(9-fluorenon-2-yl)-6-(1R-hydroxyethyl)carbapen-2-em-3-carboxylate

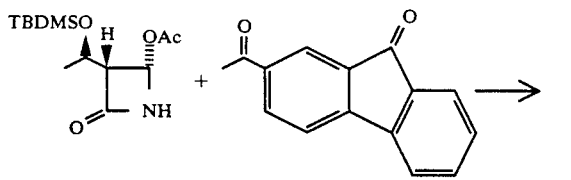

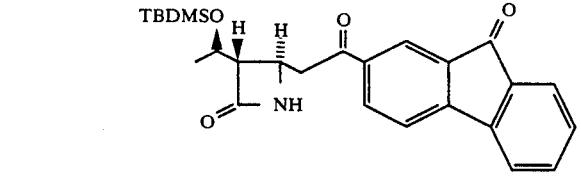

Step A: Preparation of 3-(1-R-t-butyldimethylsilyloxyethyl)-4-[2-(9-fluorenon-2-yl)-2-oxo]ethylazetidin-2-one 2-Acetyl-9-fluorenone (644 mg) was dissolved in 20 ml methylene chloride, and (3S,4S)-3-(1R-t-butyldimethylsilyloxyethyl)-4-acetoxyazetidin-2-one (880 mg) was added and the mixture was cooled to 0° C. under nitrogen. Triethylamine (1.12 ml) was added followed by trimethylsilyl triflate (1.42 ml). The reaction mixture was stirred at 0° for 15 minutes and allowed to come to room temperature. Trimethylsilyl triflate (0.204 ml) was added and the mixture was stirred at room temperature for 1 hour. The reaction mixture was diluted with methylene chloride and washed with 10% sodium bicarbonate solution, dried over magnesium sulfate and evaporated gave the crude product, chromatography on silica gel using 50% EtOAc/hexane gave the desired product (304 mg).

¹H-NMR (CDCl₃, 200 MHz): δ0.06 (s, Me₃Si); 0.84 (s, Me₃C-Si); 1.23 (d, J=7, CH₃-C); 2.89 (d of d, J=5, J=2, C-3 H); 3.16 (d of d, J=4.5, J=2.5, CH₂-C=O); 3.48 (d of d, J=4.5, J=1, CH₂-C=O); 4.16 (m, C-4 H and CH₃-CH—); 6.15 (s, NH), 7.25–8.2 (m, ArH).

IR (neat, cm⁻¹) 3340 (NH), 1755 (β-lactam), 1718 and 1680 (ketones).

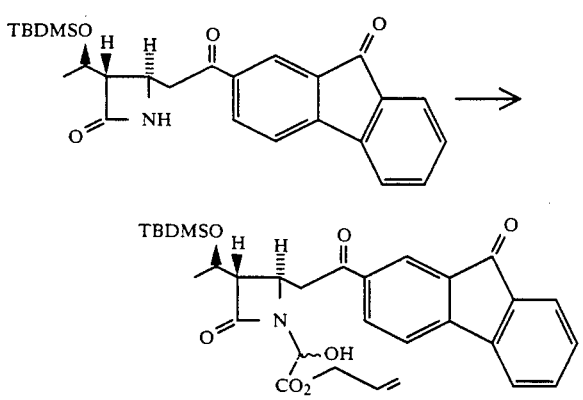

Step B: Preparation of (3S,4R)-1-(Allyloxycarbonyl)hydroxymethyl-3-(1R-t-butyldimethylsilyloxyethyl)-4-[2-(9-fluorenon-2-yl)-2-oxo]ethylazetidin-2-one The product from the previous reaction (304 mg) was dissolved in methylene chloride (12 ml) and treated with allyl glyoxalate hydrate (154 mg) and triethylamine (188 ml), MgSO₄ (3 g) was added and the mixture was allowed to stir overnight at room temperature. The MgSO₄ was filtered off and the filtrate was evaporated and chromatographed on silica gel gave the product (98 mg).

IR (neat, cm⁻¹) 3400 (NH and OH), 1755 (β-lactam), 1718 and 1680.

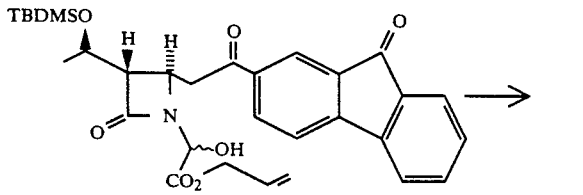

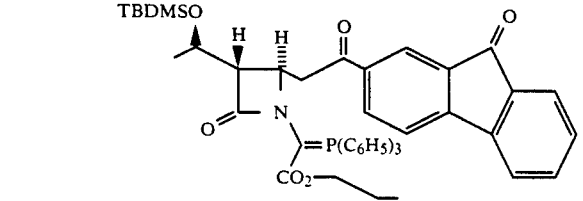

Step C: Preparation of (3S,4R)-1-(Allyloxycarbonyl)triphenylphosphoranylidene-methyl-3-(1R-t-butyldimethylsilyloxyethyl)-4-[2-(9-fluorenon-2-yl)-2-oxo]ethylazetidin-2-one The product from the previous reaction (8 mg) was dissolved in 1 ml THF and cooled to −10° under nitrogen. 2,6-Lutidine (25 ml) was added followed by $SOCl_2$ (15.5 ml). The reaction mixture was stirred for 1.5 hours during which the temperature reached 0° C. The solution was filtered and the filtrate was evaporated to dryness, the residue was taken up in DMF (1 ml) under nitrogen and treated with triphenylphosphine (54.7 mg). The reaction mixture was allowed to stir at room temperature for 3 hours. The reaction was diluted with EtOAc and washed with 10% $NaHCO_3$ solution, dried and evaporated and the residual DMF was evaporated off by flushing with toluene twice. The residue was purifed by preparative tlc and gave the product (56 mg).

IR (neat, $cm^{-1}$) 1740 (β-lactam), 1718 and 1678, 1610.

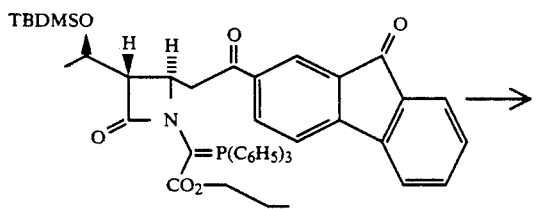

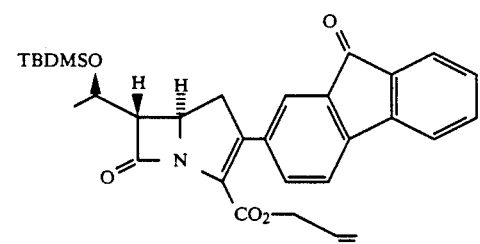

Step D: Preparation of Allyl (5R,6S)-2-(9-fluorenon-2-yl)-6-(1R-t-butyldimethyl-silyloxyethyl)carbapen-2-em-3-carboxylate The product from the previous reaction (56 mg) was dissolved in xylenes (5 ml) and degassed by bubbling nitrogen for 5 minutes, the solution was heated under nitrogen for 1.5 hours at 130°. The solvent was removed under reduced pressure and the residue was purified by preparative tlc and gave the product (33 mg).

$^1$H-NMR (CDCl$_3$, 200 MHz): δ0.13 (s, Me$_3$Si); 0.93 (s, Me$_3$C-Si): 1.31 (d, J=7, CH$_3$-C); 3.25 (m, C-6 H and C-1 H); 4.25 (m, C-5 H and CH$_3$-CH—); 4.5-6.0 (m, allyl H); 7.25-7.8 (m, ArH).

IR (neat, cm$^{-1}$) 1775 (β-lactam), 1718.

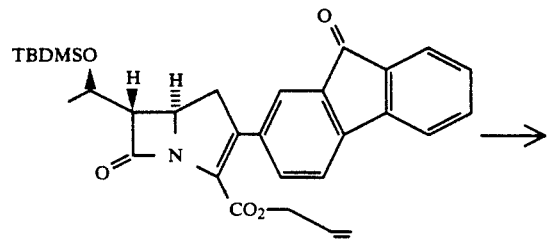

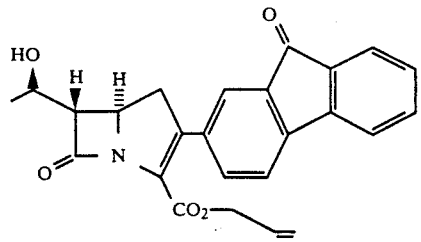

Step E: Preparation of Allyl (5R,6S)-2-(9-fluorenon-2-yl)-6-(1R-hydroxyethyl)-carbapen-2-em-3-carboxylate The product from the previous reaction (33 mg) was dissolved in THF (1 ml) and treated with acetic acid (47.6 μl) and n-Bu$_4$N$^+$F$^-$ (265 μl of a 1M solution in THF). The reaction mixture was stirred at room temperature overnight. The reaction mixture was diluted with EtOAc and washed with ice water, 10% NaHCO$_3$ solution and sat'd NaCl solution, dried and evaporated gave the crude product. Purification by preparative tlc gave the product (4 mg).

$^1$H-NMR (CDCl$_3$, 300 MHz): δ1.38 (d, J=7, CH$_3$-C); 3.28 (m, C-6 H and C-1 H); 4.25 (m, C-5 H and CH$_3$-CH—); 4.5-6.0 (m, allyl H); 7.25-7.7 (m, ArH).

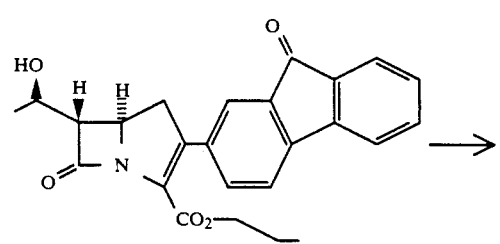

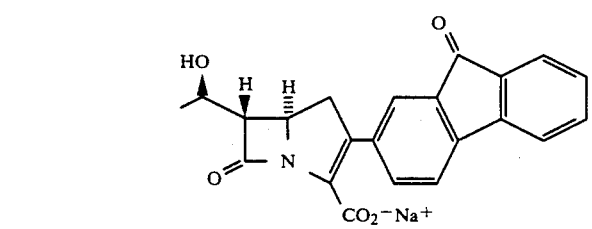

Step F: Preparation of Sodium (5R,6S)-2-(9-fluorenon-2-yl)-6-(1R-hydroxyethyl)-carbapen-2-em-3-carboxylate The product from the above reaction (4 mg) was dissolved in EtOAc (0.25 ml) and CH$_2$Cl$_2$ (0.25 ml). Sodium 2-ethylhexanoate (2.0 mg) was added followed by triphenylphosphine (1 mg) and tetrakis(triphenylphosphine)palladium(O) (1 mg). The reaction mixture was allowed to stir 15 minutes at room temperature then diluted with EtOAc (2 ml) and water (2 ml). After vigorous shaking, the layers are separated. The organic phase was extracted with water (2 ml) and the combined aqueous phase was evaporated to 1 ml and the product purified by reverse phase HPLC using CH$_3$CN/H$_2$O gradient elution, gave 2.3 mg of desired product.

$^1$H-NMR (H$_2$O, 300 MHz): δ1.42 (d, J=7, CH$_3$—C); 3.17 (d of d, J=16, J=9, C-1 Ha); 3.52 (d of d, J=16,

J=8, C-1 Hb); 3.62 (d of d, J=6, J=2.5, C-6 H); 4.4 (m, C-5 H and CH$_3$—CH—); 7.3-7.6 (m, ArH).
UV (H$_2$O, λmax): 255, 300, 340(s).

What is claimed is:
1. A compound of formula

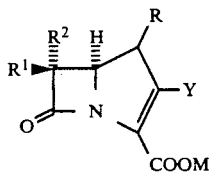

wherein:
Y is

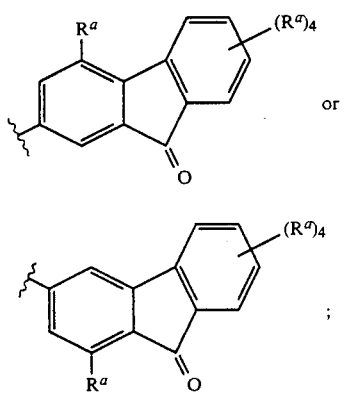

R is H or CH$_3$;

R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

R$^a$ are independently selected from the radicals set out below, provided that no more than four R$^a$ substituents are other than hydrogen:
  (a) hydrogen;
  (b) a trifluoromethyl group; —CF$_3$;
  (c) a halogen atom: —Br, —Cl, —F, or —I;
  (d) C$_1$-C$_4$ alkoxy radical: —OC$_{1-4}$ alkyl, wherein the alkyl is optionally mono-substituted by R$^q$, where
      R$^q$ is a member selected from the group consisting of: —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl or phenyl), tetrazolyl (where the point of attachment is the carbon atom of the tetrazole ring and one of the nitrogen atoms is mono-substituted by M$^a$ as defined above) and —SO$_3$M$^b$ (where M$^b$ is hydrogen or an alkali metal);
  (e) a hydroxy group: —OH;
  (f) a carbonyloxy radical of formula —O(C=O)R$^s$, where
      Rs is C$_{1-4}$ alkyl or phenyl, each of which is optionally mono-substituted by R$^q$ as defined above;
  (g) a carbamoyloxy radical of formula —O(C=O)N(R$^y$)R$^z$ where
      R$^y$ and R$^z$ are independently: H, C$_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)— or —S-(O)$_2$—, to form a ring (where the ring is optionally mono-substituted with R$^q$ as defined above);
  (h) a sulfur radical: —S(O)$_n$—R$^s$ where n=0-2, and R$^s$ is defined above;
  (i) a sulfamoyl group: —SO$_2$N(R$^y$)R$^z$ where R$^y$ and R$^z$ are as defined above;
  (j) azido: N$_3$
  (k) a formamido group: —N(R$^t$)(C=O)H, where R$^t$ is H or C$_{1-4}$ alkyl, and the alkyl thereof is optionally mono-substituted by R$^q$ as defined above;
  (l) a (C$_1$-C$_4$ alkyl)carbonylamino radical: —N(R$^t$)(C=O)C$_{1-4}$ alkyl, where
      R$^t$ is as defined above, and the alkyl group is also optionally mono-substituted by R$^q$ as defined above;
  (m) a (C$_1$-C$_4$ alkoxy)carbonylamino radical: —N(R$^t$)(C=O)OC$_{1-4}$ alkyl, where
      R$^t$ is as defined above, and the alkyl group is also optionally mono-substituted by R$^q$ as defined above;
  (n) a ureido group: —N(R$^t$)(C=O)N(R$^y$)R$^z$ where R$^t$, R$^y$ and R$^z$ are as defined above;
  (o) a sulfonamido group: —N(R$^t$)SO$_2$R$^s$, where R$^s$ and R$^t$ are as defined above;
  (p) a cyano group: —CN;
  (q) a formyl or acetalized formyl radical: —(C=O)H or —CH(OCH$_3$)$_2$;
  (r) (C$_1$-C$_4$ alkyl)carbonyl radical where the carbonyl is acetalized: —C(OCH$_3$)$_2$C$_{1-4}$ alkyl, where the alkyl is optionally mono-substituted by R$^q$ as define above;
  (s) carbonyl radical: —(C=O)R$^s$, where R$^s$ is as defined above;
  (t) a hydroximinomethyl radical in which the oxygen or carbon atom is optionally substituted by a C$_1$-C$_4$ alkyl group: —(C=NOR$^z$)R$^y$, where R$^y$ and R$^z$ are as defined above, with the previse that they are not to be joined together to form a ring;
  (u) a (C$_1$-C$_4$ alkoxy)carbonyl radical: —(C=O)OC$_{1-4}$ alkyl, where the alkyl is optionally mono-substituted by R$^q$ as defined above;
  (v) a carbamoyl radical: —(C=O)N(R$^y$)R$^z$ where R$^y$ and R$^z$ are as defined above;
  (w) an N-hydroxycarbamoyl or N(C$_1$-C$_4$ alkoxy)carbamoyl radical in which the nitrogen atom may be additionally substituted by a C$_1$-C$_4$ alkyl group: —(C=O)—N(OR$^y$)R$^z$ where R$^y$ and R$^z$ are as defined above, except they may not be joined together to form a ring;
  (x) a thiocarbamoyl group: —(C=S)N(R$^y$)R$^z$ where R$^y$ and R$^z$ are as defined above;
  (y) carboxyl: —COOM$^b$, where M$^b$ is as defined above;
  (z) thiocyanate: SCN;
  (aa) trifluoromethylthio: —SCF$_3$;
  (ab) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;

(ac) an anionic function selected from the group consisting of: phosphono: [P=O(OM$^b$)$_2$]; alkylphosphono: {P=O(OM$^b$)—[O($C_1$-$C_4$ alkyl)]}; alkylphosphinyl: [P=O(OM$^b$)—($C_1$-$C_4$ alkyl)]; phosphoramido: [P=O(OM$^b$)N(R$^y$)R$^z$ and P=O(OM$^b$)NHR$^x$]; sulfino: (SO$_2$NM$^b$); sulfo: (SO$_3$M$^b$); acylsulfonamides: selected from the structures CONM$^b$SO$_2$R$^x$, CONM$^b$SO$_2$N-(R$^y$)R$^z$, SO$_2$M$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally monosubstituted by R$^q$, as defined above; M$^b$ is as defined above; and R$^y$ and R$^z$ are as defined above;

(ad) $C_5$-$C_7$ cycloalkyl group in which one of the carbon atoms in the ring is replaced by a heteroatom selected from O, S, NH, or N($C_1$-$C_4$ alkyl) and in which one additional carbon may be replaced by the NH or N($C_1$-$C_4$ alkyl), and in which at least one carbon atom adjacent to each heteroatom has both of its attached hydrogen atoms replaced by one oxygen thus forming a carbonyl moiety and there are one or two carbonyl moieties present in the ring;

(ae) $C_2$-$C_4$ alkenyl radical, optionally mono-substituted by one of the substituents (b) to (ad) above and phenyl which is optionally substituted by R$^q$ as defined above;

(af) $C_2$-$C_4$ alkynyl radical, optionally mono-substituted by one of the substitutents (b) to (ad) above;

(ag) $C_1$-$C_4$ alkyl radical;

(ah) $C_1$-$C_4$ alkyl mono-substituted by one of the substituents (b) to (ad) above;

(ai) a 2-oxazolidinonyl moiey in which the point of attachment is the nitrogen atom of the oxazolidinone ring, the ring oxygen atom is optionally replaced by a heteroatom selected from S and NR$^t$ (where R$^t$ is as defined above) and one of the saturated carbon atoms of the oxazolidinone ring is optionally mono-substituted by one of the substituents (b) to (ah) above;

M is selected from:
(i) hydrogen;
(ii) a pharmaceutically acceptable esterifying group or removable carboxyl protecting group; or
(iii) an alkali metal or other pharmaceutically acceptable cation.

2. The compound of claim 1, wherein R$^1$ is hydrogen and R$^2$ is (R)—CH$_3$CH(OH)— or (R)—CH$_3$CH(F)—.

3. The compound of claim 2, wherein Y is:

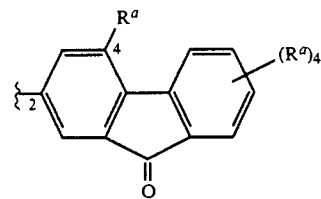

4. The compound of claim 2, wherein Y is:

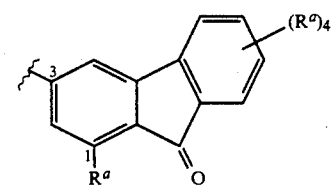

5. The compound of claim 2 wherein one to four R$^a$ substituents are selected from:

| | |
|---|---|
| —OCH$_3$ | |
| —OCH$_2$CH$_2$OH | —OCH$_2$CO$_2$Na |
| —F | —CF$_3$ |
| —Br | —Cl |
| —OH | —I |
| —OCONH$_2$ | —OCOCH$_3$ |
| —SOCH$_3$ | —SCH$_3$ |
| —SCH$_2$CH$_2$OH | —SO$_2$CH$_3$ |
| —SO$_2$NH$_2$ | —SOCH$_2$CH$_2$OH |
| —NHCHO | —SO$_2$N(CH$_3$)$_2$ |
| —NHCO$_2$CH$_3$ | —NHCOCH$_3$ |
| —CN | —NHSO$_2$CH$_3$ |
| —COCH$_3$ | —CHO |
| —CH=NOH | —COCH$_2$OH |
| —CH=NOCH$_2$CO$_2$H | —CH=NOCH$_3$ |
| —SO$_2$CH$_2$CH$_2$OH | —CH=NOCMe$_2$CO$_2$H |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$H |
| —CONHOH | —CONHCH$_3$ |
| -tetrazolyl | —CO$_2$Na |
| —SCF$_3$ | —PO$_3$NaH |
| —CONHSO$_2$Ph | —CONHSO$_2$NH$_2$ |
| —SO$_3$Na | —SO$_2$NHCN |
| —SO$_2$NHCONH$_2$ | —CH=CHCN |
| —CH=CHCONH$_2$ | —CH=CHCO$_2$Na |
| —C≡C—CONH$_2$ | —C≡C—CN |
| —CH$_2$OH | —CH$_2$N$_3$ |
| —CH$_2$CO$_2$Na and | —CH$_2$I. |

6. The compound of claim 3, in which, in total, up to two R$^a$ substituents in the 4-, 6-, 7- or 8-positions of the fluoren-9-one are other than hydrogen.

7. The compound of claim 4, in which, in total, up to two R$^a$ substituents in the 1-, 6-, 7 or 8-positions of the fluoren-9-one are other than hydrogen.

8. The compound of claim 4, wherein the structural formula is:

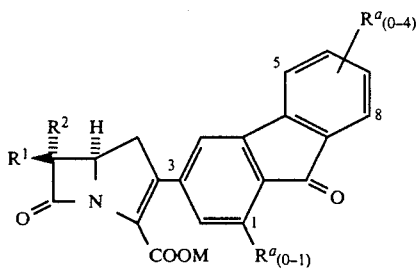

and the substituents $R^a$ when it is not hydrogen, R, $R^1$, $R^2$ and M are as defined in Table I below and when $R^2$ is 1-fluoroethyl or 1-hydroxyethyl the stereochemistry is (R):

TABLE I

| # | R | $R^1$ | $R^2$ | M | $R^a$ | $R^a$ position |
|---|---|---|---|---|---|---|
| 1 | —H | —H | —CH(OH)CH₃ | K⁺ | —OCH₃ | 1 |
| 2 | —H | —H | —CH(OH)CH₃ | Na⁺ | —OCH₂CO₂Na | 1 |
| 3 | —H | —H | —CH(OH)CH₃ | K⁺ | —OCH₂CH₂OH | 1 |
| 4 | —H | —H | —CH(OH)CH₃ | K⁺ | —CF₃ | 1 |
| 5 | —H | —H | —CH(OH)CH₃ | Na⁺ | —F | 1 |
| 6 | —H | —H | —CH(OH)CH₃ | Na⁺ | —Cl | 1 |
| 7 | —H | —H | —CH(OH)CH₃ | K⁺ | —Br | 7 |
| 8 | —H | —H | —CH₂OH | K⁺ | —I | 1,6 |
| 9 | —H | —H | —CH(OH)CH₃ | K⁺ | —OH | 1,6,7 |
| 10 | —H | —H | —CH(OH)CH₃ | Na⁺ | —OCOCH₃ | 6 |
| 11 | —H | —H | —CH(OH)CH₃ | Na⁺ | —OCONH₂ | 6 |
| 12 | —H | —H | —CH(OH)CH₃ | Na⁺ | —SCH₃ | 7 |
| 13 | —H | —H | —CH(F)CH₃ | K⁺ | —SOCH₃ | 6 |
| 14 | —CH₃ | —H | —CH(OH)CH₃ | Na⁺ | —SO₂CH₃ | 7 |
| 15 | —H | —H | —CH(OH)CH₃ | Na⁺ | —SCH₂CH₂OH | 7 |
| 16 | —H | —H | —CH(OH)CH₃ | Na⁺ | —SOCH₂CH₂OH | 7 |
| 17 | —H | —H | —CH(OH)CH₃ | K⁺ | —SO₂CH₂CH₂OH | 7 |
| 18 | —H | —H | —CH(OH)CH₃ | Na⁺ | —SO₂NH₂ | 1,7 |
| 19 | —H | —H | —CH(OH)CH₃ | K⁺ | —SO₂N(CH₃)₂ | 1,6 |
| 20 | —H | —H | —CF₂CH₃ | K⁺ | —NHCHO | 1,6 |
| 21 | —CH₃ | —H | —CH(OH)CH₃ | K⁺ | —NHCOCH₃ | 1,7 |
| 22 | —H | —H | —CH(OH)CH₃ | K⁺ | —NHCO₂CH₃ | 1,6 |
| 23 | —H | —H | —CH(OH)CH₃ | Na⁺ | —NHSO₂CH₃ | 1,7 |
| 24 | —H | —H | —CH(OH)CH₃ | Na⁺ | —CN | 6 |
| 25 | —H | —H | —CH(OH)CH₃ | Na⁺ | —CHO | 7 |
| 26 | —H | —H | —CH(OH)CH₃ | K⁺ | —COCH₃ | 6 |
| 27 | —H | —H | —CH(OH)CH₃ | K⁺ | —COCH₂OH | 7 |
| 28 | —H | —H | —CH(OH)CH₃ | K⁺ | —CH=NOH | 6 |
| 29 | —H | —H | —CH(OH)CH₃ | Na⁺ | —CH=NOCH₃ | 7 |
| 30 | —CH₃ | —H | —CH(OH)CH₃ | K⁺ | —CH=NOCH₂CO₂K | 1 |
| 31 | —H | —H | —CH(OH)CH₃ | Na⁺ | —CH=NOCMe₂CO₂Na | 6 |
| 32 | —H | —H | —CH(OH)CH₃ | Na⁺ | —CH=NOCMe₂CO₂Me | 7 |
| 33 | —H | —H | —CH(OH)CH₃ | K⁺ | —CO₂CH₂CH₂OH | 1 |
| 34 | —H | —H | —CH(OH)CH₃ | Na⁺ | —CONH₂ | 1 |
| 35 | —H | —H | —CH(OH)CH₃ | K⁺ | —CONHCH₃ | 7 |
| 36 | —H | —H | —CH(OH)CH₃ | K⁺ | —CON(CH₃)₂ | 6 |
| 37 | —H | —H | —CH(OH)CH₃ | K⁺ | —CONHCH₂CN | 7 |
| 38 | —CH₃ | —H | —CF₂CH₃ | Na⁺ | —CONHCH₂CONH₂ | 1 |
| 39 | —H | —H | —CH(OH)CH₃ | K⁺ | —CONHCH₂CO₂K | 6 |
| 40 | —H | —H | —CH(OH)CH₃ | Na⁺ | —CONHOH | 7 |
| 41 | —H | —H | —CH(OH)CH₃ | Na⁺ | —CONHOCH₃ | 1 |
| 42 | —H | —H | —CH(OH)CH₃ | Na⁺ | -tetrazolyl | 6 |
| 43 | —H | —H | —CH(OH)CH₃ | Na⁺ | —CO₂Na | 1 |
| 44 | —H | —H | —CH(OH)CH₃ | Na⁺ | —SCF₃ | 6 |
| 45 | —H | —H | —CH(OH)CH₃ | Na⁺ | —PO₃NaH | 7 |
| 46 | —H | —H | —CH(OH)CH₃ | Na⁺ | —CONHSO₂Ph | 1 |
| 47 | —CH₃ | —H | —CH(OH)CH₃ | Na⁺ | —CONHSO₂NH₂ | 6 |
| 48 | —H | —H | —CH(OH)CH₃ | Na⁺ | —SO₃Na | 6 |
| 49 | —H | —H | —CH(OH)CH₃ | Na⁺ | —SO₂NHCN | 7 |
| 50 | —CH₃ | —H | —CH(F)CH₃ | Na⁺ | —SO₂NHCONH₂ | 6 |
| 51 | —H | —H | —CH(OH)CH₃ | K⁺ | —CH=CHCN | 1 |
| 52 | —H | —H | —CH(OH)CH₃ | K⁺ | —CH=CHCONH₂ | 6 |
| 53 | —H | —H | —CH(OH)CH₃ | Na⁺ | —CH=CHCO₂Na | 7 |
| 54 | —H | —H | —CH(OH)CH₃ | Na⁺ | —C≡C—CONH₂ | 1 |
| 55 | —CH₃ | —H | —CH(OH)CH₃ | Na⁺ | —C≡C—CN | 6 |
| 56 | —H | —H | —CH(OH)CH₃ | Na⁺ | —CH₂OH | 1 |
| 57 | —H | —H | —CH(OH)CH₃ | Na⁺ | —CH₂OH | 6 |
| 58 | —H | —H | —CH(OH)CH₃ | Na⁺ | —CH₂OH | 7 |
| 59 | —H | —H | —CH(OH)CH₃ | K⁺ | —CH₂N₃ | 6 |
| 60 | —H | —H | —CH(OH)CH₃ | Na⁺ | —CH₂CO₂Na | 7 |
| 61 | —H | —H | —CH(OH)CH₃ | Na⁺ | —CH₂CO₂Na | 1 |
| 62 | —CH₃ | —H | —CH(OH)CH₃ | Na⁺ | —CN | 1 |
| 63 | —H | —H | —CH(OH)CH₃ | Na⁺ | —CH₂OH | 8 |
| 64 | —H | —H | —CH(OH)CH₃ | Na⁺ | —CH₂OH | 5 |

TABLE I-continued

| # | R | R¹ | R² | M | $R^a$ | $R^a$ position |
|---|---|----|----|---|-------|----------------|
| 65 | —H | —H | —CH(OH)CH₃ | Na⁺ | —CHO | 1 |
| 66 | —H | —H | —CH(OH)CH₃ | Na⁺ | —CHO | 8 |
| 67 | —H | —H | —CH(OH)CH₃ | Na⁺ | —CO₂CH₃ | 1 |
| 68 | —H | —H | —CH(F)CH₃ | Na⁺ | —CO₂Na | 8 |
| 69 | —CH₃ | —H | —CH(OH)CH₃ | Na⁺ | —CH₂CO₂Na | 5 |
| 70 | —H | —H | —CH(OH)CH₃ | Na⁺ | —SCH₃ | 5 |
| 71 | —H | —H | —CH(F)CH₃ | Na⁺ | —SOCH₃ | 8 |
| 72 | —CH₃ | —H | —CH(OH)CH₃ | Na⁺ | —SO₂CH₃ | 5 |
| 73 | —H | —H | —CH(OH)CH₃ | Na⁺ | —CH=CHCN | 6 |
| 74 | —H | —H | —CH(OH)CH₃ | Na⁺ | —CH=CHCN | 7 |
| 75 | —H | —H | —CH(OH)CH₃ | Na⁺ | —CN | 7 |
| 76 | —H | —H | —CH(OH)CH₃ | Na⁺ | —CH=NOCH₃ | 1 |
| 77 | —H | —H | —CH(OH)CH₃ | Na⁺ | —CH=NOCH₃ | 6 |
| 78 | —H | —H | —CH(OH)CH₃ | Na⁺ | —CO₂CH₃ | 6 |
| 79 | —H | —H | —CH(OH)CH₃ | Na⁺ | —CO₂CH₃ | 7 |
| 80 | —H | —H | —CH(OH)CH₃ | Na⁺ | —CO₂Na | 1 |
| 81 | —H | —H | —CH(OH)CH₃ | Na⁺ | —CO₂Na | 6 |
| 82 | —H | —H | —CH(OH)CH₃ | Na⁺ | —CO₂Na | 7 |
| 83 | —H | —H | —CH(OH)CH₃ | Na⁺ | —CONH₂ | 6 |
| 84 | —H | —H | —CH(OH)CH₃ | Na⁺ | —CONH₂ | 7 |
| 85 | —H | —H | —CH(OH)CH₃ | Na⁺ | —CONHCH₃ | 1 |
| 86 | —H | —H | —CH(OH)CH₃ | Na⁺ | —CONHCH₃ | 6 |
| 87 | —H | —H | —CH(OH)CH₃ | Na⁺ | —CONH(CH₃)₂ | 1 |
| 88 | —H | —H | —CH(OH)CH₃ | Na⁺ | —CONH(CH₃)₂ | 7 |
| 89 | —H | —H | —CH(OH)CH₃ | Na⁺ | —SCH₃ | 1 |
| 90 | —H | —H | —CH(OH)CH₃ | Na⁺ | —SCH₃ | 6 |
| 91 | —H | —H | —CH(OH)CH₃ | Na⁺ | —SOCH₃ | 7 |
| 92 | —H | —H | —CH(OH)CH₃ | Na⁺ | —SO₂CH₃ | 1 |
| 93 | —H | —H | —CH(OH)CH₃ | Na⁺ | —SO₂CH₃ | 6 |
| 94 | —H | —H | —CH(OH)CH₃ | Na⁺ | —SO₂CH₃ | 7. |

9. The compound of claim 3, wherein the structural formula is:

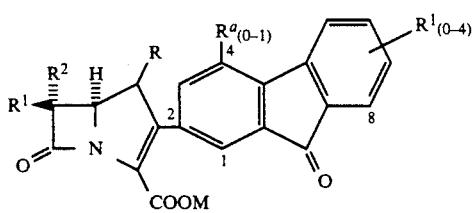

and the substituents $R^a$ when it is not hydrogen, R, R¹, R² and M are as defined in Table II below, and when R² is 1-fluoroethyl or 1-hydroxyethyl the stereochemistry is (R):

TABLE II

| # | R | R¹ | R² | M | $R^a$ | $R^a$ position |
|---|---|----|----|---|-------|----------------|
| 1 | —H | —H | —CH(F)CH₃ | K⁺ | —OCH₃ | 4 |
| 2 | —H | —H | —CH(OH)CH₃ | Na⁺ | —OCH₂CO₂Na | 4 |
| 3 | —H | —H | —CH(OH)CH₃ | K⁺ | —OCH₂CH₂OH | 4 |
| 4 | —H | —H | —CH(OH)CH₃ | K⁺ | —CF₃ | 4 |
| 5 | —H | —H | —CH(OH)CH₃ | Na⁺ | —F | 4 |
| 6 | —H | —H | —CH(OH)CH₃ | Na⁺ | —Cl | 6 |
| 7 | —H | —H | —CH(OH)CH₃ | K⁺ | —Br | 7 |
| 8 | —H | —H | —CH(OH)CH₃ | K⁺ | —I | 4,6 |
| 9 | —H | —H | —CH(OH)CH₃ | K⁺ | —OH | 4,6,7 |
| 10 | —H | —H | —CH(OH)CH₃ | Na⁺ | —OCOCH₃ | 6 |
| 11 | —H | —H | —CH(OH)CH₃ | Na⁺ | —OCONH₂ | 6 |
| 12 | —H | —H | —CH(OH)CH₃ | K⁺ | —SCH₃ | 6 |
| 13 | —H | —H | —CH(F)CH₃ | K⁺ | —SOCH₃ | 7 |
| 14 | —CH₃ | —H | —CH(OH)CH₃ | Na⁺ | —SO₂CH₃ | 7 |
| 15 | —H | —H | —CH(OH)CH₃ | Na⁺ | —SCH₂CH₂OH | 7 |
| 16 | —H | —H | —CH(OH)CH₃ | Na⁺ | —SOCH₂CH₂OH | 7 |
| 17 | —H | —H | —CH(OH)CH₃ | K⁺ | —SO₂CH₂CH₂OH | 7 |
| 18 | —H | —H | —CH(OH)CH₃ | Na⁺ | —SO₂NH₂ | 4,7 |
| 19 | —H | —H | —CH(OH)CH₃ | K⁺ | —SO₂N(CH₃)₂ | 4,6 |
| 20 | —H | —H | —CF₂CH₃ | K⁺ | —NHCHO | 4,6 |
| 21 | —CH₃ | —H | —CH(OH)CH₃ | K⁺ | —NHCOCH₃ | 4,7 |
| 22 | —H | —H | —CH(OH)CH₃ | K⁺ | —NHCO₂CH₃ | 4,6 |
| 23 | —H | —H | —CH(OH)CH₃ | Na⁺ | —NHSO₂CH₃ | 4,7 |
| 24 | —H | —H | —CH(OH)CH₃ | Na⁺ | —CN | 6 |
| 25 | —H | —H | —CH(OH)CH₃ | K⁺ | —CHO | 7 |
| 26 | —H | —H | —CH₂OH | K⁺ | —COCH₃ | 6 |
| 27 | —H | —H | —CH(OH)CH₃ | K⁺ | —COCH₂OH | 7 |

TABLE II-continued

| # | R | $R^1$ | $R^2$ | M | $R^a$ | $R^a$ position |
|---|---|---|---|---|---|---|
| 28 | —H | —H | —CH(OH)CH$_3$ | K$^+$ | —CH=NOH | 6 |
| 29 | —H | —H | —CH(OH)CH$_3$ | Na$^+$ | —CH=NOCH$_3$ | 7 |
| 30 | —CH$_3$ | —H | —CH(OH)CH$_3$ | K$^+$ | —CH=NOCH$_2$CO$_2$K | 4 |
| 31 | —H | —H | —CH(OH)CH$_3$ | Na$^+$ | —CH=NOCMe$_2$CO$_2$Na | 6 |
| 32 | —H | —H | —CH(OH)CH$_3$ | —H | —CH=NOCMe$_2$CO$_2$Me | 7 |
| 33 | —H | —H | —CH(OH)CH$_3$ | K$^+$ | —CO$_2$CH$_2$CH$_2$OH | 4 |
| 34 | —H | —H | —CH(OH)CH$_3$ | Na$^+$ | —CONH$_2$ | 6 |
| 35 | —H | —H | —CH(OH)CH$_3$ | Na$^+$ | —CONHCH$_3$ | 7 |
| 36 | —H | —H | —CH(OH)CH$_3$ | Na$^+$ | —CON(CH$_3$)$_2$ | 6 |
| 37 | —H | —H | —CH(OH)CH$_3$ | K$^+$ | —CONHCH$_2$CN | 7 |
| 38 | —CH$_3$ | —H | —CF$_2$CH$_3$ | Na$^+$ | —CONHCH$_2$CONH$_2$ | 4 |
| 39 | —H | —H | —CH(OH)CH$_3$ | K$^+$ | —CONHCH$_2$CO$_2$H | 6 |
| 40 | —H | —H | —CH(OH)CH$_3$ | Na$^+$ | —CONHOH | 7 |
| 41 | —H | —H | —CH(OH)CH$_3$ | Na$^+$ | —CONHOCH$_3$ | 4 |
| 42 | —H | —H | —CH(OH)CH$_3$ | Na$^+$ | -tetrazolyl | 6 |
| 43 | —H | —H | —CH(OH)CH$_3$ | Na$^+$ | —CO$_2$Na | 4 |
| 44 | —H | —H | —CH(OH)CF$_3$ | Na$^+$ | —SCF$_3$ | 6 |
| 45 | —H | —H | —CH(OH)CH$_3$ | Na$^+$ | —PO$_3$NaH | 7 |
| 46 | —H | —H | —CH(OH)CH$_3$ | Na$^+$ | —CONHSO$_2$Ph | 4 |
| 47 | —CH$_3$ | —H | —CH(OH)CH$_3$ | Na$^+$ | —CONHSO$_2$NH$_2$ | 6 |
| 48 | —H | —H | —CH(OH)CH$_3$ | Na$^+$ | —SO$_3$Na | 6 |
| 49 | —H | —H | —CH(OH)CH$_3$ | Na$^+$ | —SO$_2$NHCN | 7 |
| 50 | —CH$_3$ | —H | —CH(F)CH$_3$ | Na$^+$ | —SO$_2$NHCONH$_2$ | 6 |
| 51 | —H | —H | —CH(OH)CH$_3$ | K$^+$ | —CH=CHCN | 4 |
| 52 | —H | —H | —CH(OH)CH$_3$ | K$^+$ | —CH=CHCONH$_2$ | 6 |
| 53 | —H | —H | —CH(OH)CH$_3$ | Na$^+$ | —CH=CHCO$_2$Na | 7 |
| 54 | —H | —H | —CH(OH)CH$_3$ | Na$^+$ | —C≡C—CONH$_2$ | 4 |
| 55 | —CH$_3$ | —H | —CH(OH)CH$_3$ | Na$^+$ | —C≡C—CN | 6 |
| 56 | —H | —H | —CH(OH)CH$_3$ | Na$^+$ | —CH$_2$OH | 4 |
| 57 | —H | —H | —CH(OH)CH$_3$ | Na$^+$ | —CH$_2$OH | 6 |
| 58 | —H | —H | —CH(OH)CH$_3$ | Na$^+$ | —CH$_2$OH | 7 |
| 59 | —H | —H | —CH$_2$CH$_3$ | K$^+$ | —CH$_2$N$_3$ | 6 |
| 60 | —H | —H | —CH(OH)CH$_3$ | Na$^+$ | —CH$_2$CO$_2$Na | 7 |
| 61 | —H | —H | —CH(OH)CH$_3$ | Na$^+$ | —CH$_2$CO$_2$Na | 4 |
| 62 | —CH$_3$ | —H | —CH(OH)CH$_3$ | Na$^+$ | —CN | 5 |
| 63 | —H | —H | —CH(OH)CH$_3$ | Na$^+$ | —CH$_2$OH | 8 |
| 64 | —H | —H | —CH(OH)CH$_3$ | Na$^+$ | —CH$_2$OH | 5 |
| 65 | —H | —H | —CH(OH)CH$_3$ | Na$^+$ | —CHO | 5 |
| 66 | —H | —H | —CH(OH)CH$_3$ | Na$^+$ | —CHO | 8 |
| 67 | —H | —H | —CH(OH)CH$_3$ | Na$^+$ | —CO$_2$CH$_3$ | 5 |
| 68 | —H | —H | —CH(F)CH$_3$ | Na$^+$ | —CO$_2$Na | 8 |
| 69 | —CH$_3$ | —H | —CH(OH)CH$_3$ | Na$^+$ | —CH$_2$CO$_2$Na | 5 |
| 70 | —H | —H | —CH(OH)CH$_3$ | Na$^+$ | —SCH$_3$ | 5 |
| 71 | —H | —H | —CH(F)CH$_3$ | Na$^+$ | —SOCH$_3$ | 8 |
| 72 | —CH$_3$ | —H | —CH(OH)CH$_3$ | Na$^+$ | —SO$_2$CH$_3$ | 5 |
| 73 | —H | —H | —CH(OH)CH$_3$ | Na$^+$ | —CH=CHCN | 6 |
| 74 | —H | —H | —CH(OH)CH$_3$ | Na$^+$ | —CH=CHCN | 7 |
| 75 | —H | —H | —CH(OH)CH$_3$ | Na$^+$ | —CN | 7 |
| 76 | —H | —H | —CH(OH)CH$_3$ | Na$^+$ | —CH=NOCH$_3$ | 4 |
| 77 | —H | —H | —CH(OH)CH$_3$ | Na$^+$ | —CH=NOCH$_3$ | 6 |
| 78 | —H | —H | —CH(OH)CH$_3$ | Na$^+$ | —CO$_2$CH$_3$ | 6 |
| 79 | —H | —H | —CH(OH)CH$_3$ | Na$^+$ | —CO$_2$CH$_3$ | 7 |
| 80 | —H | —H | —CH(OH)CH$_3$ | Na$^+$ | —CO$_2$Na | 4 |
| 81 | —H | —H | —CH(OH)CH$_3$ | Na$^+$ | —CO$_2$Na | 6 |
| 82 | —H | —H | —CH(OH)CH$_3$ | Na$^+$ | —CO$_2$Na | 7 |
| 83 | —H | —H | —CH(OH)CH$_3$ | Na$^+$ | —CONH$_2$ | 6 |
| 84 | —H | —H | —CH(OH)CH$_3$ | Na$^+$ | —CONH$_2$ | 7 |
| 85 | —H | —H | —CH(OH)CH$_3$ | Na$^+$ | —CONHCH$_3$ | 4 |
| 86 | —H | —H | —CH(OH)CH$_3$ | Na$^+$ | —CONHCH$_3$ | 6 |
| 87 | —H | —H | —CH(OH)CH$_3$ | Na$^+$ | —CONH(CH$_3$)$_2$ | 4 |
| 88 | —H | —H | —CH(OH)CH$_3$ | Na$^+$ | —CONH(CH$_3$)$_2$ | 7 |
| 89 | —H | —H | —CH(OH)CH$_3$ | Na$^+$ | —SCH$_3$ | 4 |
| 90 | —H | —H | —CH(OH)CH$_3$ | Na$^+$ | —SCH$_3$ | 6 |
| 91 | —H | —H | —CH(OH)CH$_3$ | Na$^+$ | —SOCH$_3$ | 7 |
| 92 | —H | —H | —CH(OH)CH$_3$ | Na$^+$ | —SO$_2$CH$_3$ | 4 |
| 93 | —H | —H | —CH(OH)CH$_3$ | Na$^+$ | —SO$_2$CH$_3$ | 6 |
| 94 | —H | —H | —CH(OH)CH$_3$ | Na$^+$ | —SO$_2$CH$_3$ | 7. |

10. A compound wherein the structural formula is:

and the substituents are as defined in Table IV below, and R² is defined as (R)-1-fluoroethyl or (R)-1-hydroxyethyl:

TABLE IV

| # | R | R¹ | R² | M | Rᵃ | Rᵃ |
|---|---|----|----|---|-----|-----|
| 1 | —H | —H | —CH(OH)CH₃ | Na⁺ | 4-CH₂OH | 7-CHO |
| 2 | —H | —H | —CH(OH)CH₃ | Na⁺ | 4-CHO | 7-CH₂OH |
| 3 | —H | —H | —CH(OH)CH₃ | Na⁺ | 4-COCH₃ | 7-CHO |
| 4 | —H | —H | —CH(OH)CH₃ | Na⁺ | 4-CO₂CH₃ | 6-CHO |
| 5 | —H | —H | —CH(OH)CH₃ | Na⁺ | 4-CH₂OH | 6-CO₂CH₃ |
| 6 | —H | —H | —CH(OH)CH₃ | Na⁺ | 4-CO₂CH₃ | 7-CN |
| 7 | —H | —H | —CH(OH)CH₃ | K⁺ | 4-CO₂CH₃ | 7-CH₂OH |
| 8 | —H | —H | —CH(OH)CH₃ | K⁺ | 4-CH₂OH | 6-SOCH₃ |
| 9 | —H | —H | —CH(F)CH₃ | Na⁺ | 4-CO₂Na | 7-CHO |
| 10 | —H | —H | —CH(OH)CH₃ | Na⁺ | 4-CO₂Na | 6-CHO |
| 11 | —H | —H | —CH(OH)CH₃ | K⁺ | 4-CONH₂ | 7-CN |
| 12 | —H | —H | —CH(OH)CH₃ | K⁺ | 4-CONHOH | 6-CN |
| 13 | —H | —H | —CH(OH)CH₃ | Na⁺ | 4-CH=NOH | 7-CHO |
| 14 | —H | —H | —CH(OH)CH₃ | Na⁺ | 4-CH=NOCHCO₂Na | 6-CHO |
| 15 | —H | —H | —CH(OH)CH₃ | Na⁺ | 4-CN | 8-CHO |
| 16 | —H | —H | —CH(OH)CH₃ | K⁺ | 4-CH₂OH | 8-CN |
| 17 | —H | —H | —CH(OH)CH₃ | K⁺ | 4-COCH₃ | 8-CHO |
| 18 | —H | —H | —CH(OH)CH₃ | Na⁺ | 4-CO₂CH₃ | 8-SOCH₃ |
| 19 | —H | —H | —CH(OH)CH₃ | Na⁺ | 4-CO₂Na | 8-CHO |
| 20 | —H | —H | —CH(OH)CH₃ | K⁺ | 4-CH=NOH | 8-CN |

12. A compound wherein the structural formula is:

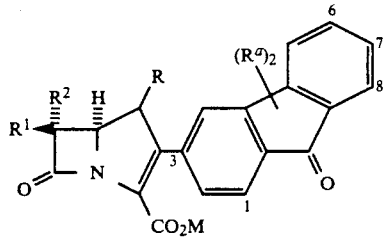

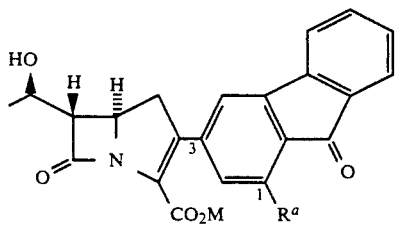

and the substituents are as defined in Table III below, and R² is defined as (R)-1-fluoroethyl or (R)-1-hydroxyethyl:

TABLE III

| # | R | R¹ | R² | M | Rᵃ | Rᵃ |
|---|---|----|----|---|-----|-----|
| 1 | —H | —H | —CH(OH)CH₃ | Na⁺ | 1-CH₂OH | 7-CHO |
| 2 | —H | —H | —CH(OH)CH₃ | Na⁺ | 1-CHO | 7-CH₂OH |
| 3 | —H | —H | —CH(OH)CH₃ | Na⁺ | 1-COCH₃ | 7-CHO |
| 4 | —H | —H | —CH(OH)CH₃ | Na⁺ | 1-CO₂CH₃ | 6-CHO |
| 5 | —H | —H | —CH(OH)CH₃ | Na⁺ | 1-CH₂OH | 6-CO₂CH₃ |
| 6 | —H | —H | —CH(OH)CH₃ | Na⁺ | 1-CO₂CH₃ | 7-CN |
| 7 | —H | —H | —CH(OH)CH₃ | K⁺ | 1-CO₂CH₃ | 7-CH₂OH |
| 8 | —H | —H | —CH(OH)CH₃ | K⁺ | 1-CH₂OH | 6-SOCH₃ |
| 9 | —H | —H | —CH(F)CH₃ | Na⁺ | 1-CO₂Na | 7-CHO |
| 10 | —H | —H | —CH(OH)CH₃ | Na⁺ | 1-CO₂Na | 6-CHO |
| 11 | —H | —H | —CH(OH)CH₃ | K⁺ | 1-CONH₂ | 7-CN |
| 12 | —H | —H | —CH(OH)CH₃ | K⁺ | 1-CONHOH | 6-CN |
| 13 | —H | —H | —CH(OH)CH₃ | Na⁺ | 1-CH=NOH | 7-CHO |
| 14 | —H | —H | —CH(OH)CH₃ | Na⁺ | 1-CH=NOCHCO₂Na | 6-CHO |
| 15 | —H | —H | —CH(OH)CH₃ | Na⁺ | 1-CN | 8-CHO |
| 16 | —H | —H | —CH(OH)CH₃ | K⁺ | 1-CH₂OH | 8-CN |
| 17 | —H | —H | —CH(OH)CH₃ | K⁺ | 1-COCH₃ | 8-CHO |
| 18 | —H | —H | —CH(OH)CH₃ | Na⁺ | 1-CO₂CH₃ | 8-SOCH₃ |
| 19 | —H | —H | —CH(OH)CH₃ | Na⁺ | 1-CO₂Na | 8-CHO |
| 20 | —H | —H | —CH(OH)CH₃ | K⁺ | 1-CH=NOH | 8-CN |

11. A compound wherein the structural formula is:

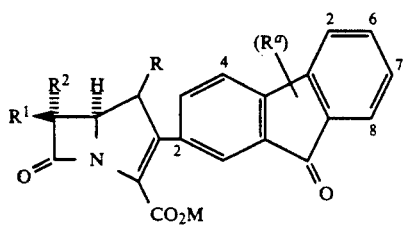

and M is Na⁺ or K⁺ and the Rᵃ substituents are CH₂OH, CO₂CH₃, CONH₂, Cl, CN, CHO, SCH₃, SOCH₃ and SO₂CH₃.

13. A compound wherein the structural formula is:

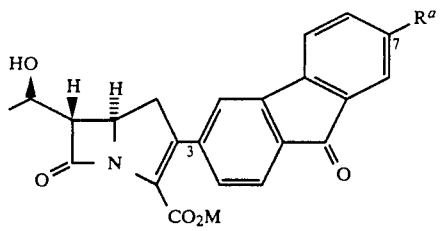

and M is Na+ or K+ and the $R^a$ substituents are $CH_2OH$, $SCH_3$ or CHO.

14. A pharmaceutical composition for antibacterial use comprising an antibacterially effective amount of a compound of claim 1 and a pharmaceutically acceptable carrier.

15. A method of treating bacterial infections in human or animal subjects in need of such treatment comprising administering to such subject an antibacterially effective amount of a compound of claim 1.

16. A pharmaceutical composition for antibacterial use comprising an antibacterially effective amount of a compound of claim 1, an inhibitorily effective amount of a dehydropeptidase (DHP) inhibitor, and optionally, a pharmaceutically acceptable carrier.

17. A pharmaceutical composition according to claim 16, wherein the DHP inhibitor is 7-(L-2-amino-2-carboxyethylthio)-2-(2,2-dimethylcyclopropanecarboxamide)-2-heptenoic acid.

18. A method of treating bacterial infections in human or animal subjects in need of such treatment comprising coadministering to such subject an antibacterially effective amount of a compound of claim 1 and an inhibitorily effective amount of a DHP inhibitor.

19. The method according to claim 18, wherein the DHP inhibitor is 7-(L-2-amino-2-carboxyethylthio)-2-(2,2-dimethylcyclopropanecarboxamide)-2-heptenoic acid.

* * * * *

UNITED STATES PATENT AND TRADEMARK OFFICE
CERTIFICATE OF CORRECTION

PATENT NO.  : 5,025,007
DATED       : June 18, 1991
INVENTOR(S) : Mark L. Greenlee, et al.

It is certified that error appears in the above-identified patent and that said Letters Patent is hereby corrected as shown below:

Column 93, claim 11, line 2, replace;

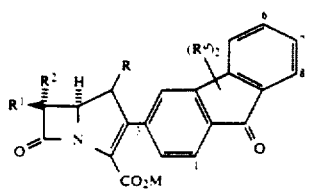

with

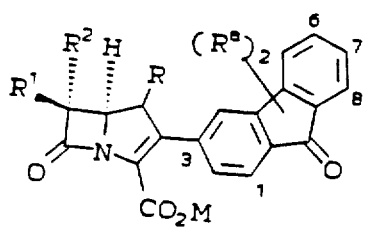

Signed and Sealed this

Thirteenth Day of April, 1993

Attest:

STEPHEN G. KUNIN

Attesting Officer	Acting Commissioner of Patents and Trademarks